(12) United States Patent
Buechler et al.

(10) Patent No.: US 7,713,703 B1
(45) Date of Patent: May 11, 2010

(54) METHODS FOR MONITORING THE STATUS OF ASSAYS AND IMMUNOASSAYS

(75) Inventors: Kenneth F. Buechler, San Diego, CA (US); Joseph M Anderberg, Encinitas, CA (US); Paul H. McPherson, Encinitas, CA (US)

(73) Assignee: Biosite, Inc., Waltham, MA (US)

( * ) Notice: Subject to any disclaimer, the term of this patent is extended or adjusted under 35 U.S.C. 154(b) by 828 days.

(21) Appl. No.: 09/712,615

(22) Filed: Nov. 13, 2000

(51) Int. Cl.
*G01N 33/53* (2006.01)

(52) U.S. Cl. .................. 435/7.1; 435/283.1; 436/43

(58) Field of Classification Search .............. 435/4, 435/7, 7.21, 69.2, 7.94, 25, 28, 805, 810, 435/967, 970, 971, 287.1, 287.2, 287.7, 287.9, 435/184, 518, 14; 436/65, 530, 541, 169, 436/510, 514, 518, 523, 525, 531, 534, 805, 436/810, 818, 162, 904, 166, 170; 422/56, 422/57, 58, 101; 250/208.1, 211 R; 357/301.1; 358/494, 497, 213.22
See application file for complete search history.

(56) References Cited

U.S. PATENT DOCUMENTS

| | | | |
|---|---|---|---|
| 3,966,897 A | 6/1976 | Renn et al. | |
| 4,094,647 A | 6/1978 | Deutsch et al. | 23/253 |
| 4,099,886 A | 7/1978 | Oliveira | 356/244 |
| 4,168,146 A | 9/1979 | Grubb et al. | 23/230 |
| 4,200,690 A | 4/1980 | Root et al. | 435/7 |
| 4,205,058 A | 5/1980 | Wagner et al. | 424/1 |
| 4,281,061 A * | 7/1981 | Zuk et al. | 435/7 |
| 4,298,688 A | 11/1981 | Kallies | 435/14 |
| 4,391,904 A | 7/1983 | Litman et al. | 435/7 |
| 4,435,504 A | 3/1984 | Zuk et al. | 435/7 |
| 4,444,879 A * | 4/1984 | Foster et al. | 435/7 |
| 4,472,353 A | 9/1984 | Moore | 422/58 |
| 4,533,629 A | 8/1985 | Litman et al. | 435/7 |
| 4,540,659 A | 9/1985 | Litman et al. | 435/7 |
| 4,541,987 A | 9/1985 | Guadagno | 422/56 |
| 4,549,121 A | 10/1985 | Gale | 436/14 |
| 4,558,013 A | 12/1985 | Marinkovich et al. | 436/513 |
| 4,837,168 A | 6/1989 | de Jaeger et al. | |
| 4,843,000 A | 6/1989 | Litman et al. | 435/7 |
| 4,849,338 A | 7/1989 | Litman et al. | 435/7 |
| 4,857,453 A | 8/1989 | Ullman et al. | 435/7 |
| 4,963,468 A | 10/1990 | Olson | 435/7 |
| 5,028,535 A | 7/1991 | Buechler et al. | 435/7.1 |
| 5,053,199 A | 10/1991 | Keiser et al. | 422/68.1 |
| 5,073,484 A | 12/1991 | Swanson et al. | 435/7.92 |
| 5,079,415 A * | 1/1992 | Hayashi et al. | 250/208.1 |
| 5,089,391 A | 2/1992 | Buechler et al. | 435/7.1 |
| 5,098,837 A | 3/1992 | Beckmann et al. | 436/514 |
| 5,132,097 A * | 7/1992 | Van Deusen et al. | 422/82.09 |
| 5,139,630 A | 8/1992 | Chen et al. | |
| 5,164,598 A | 11/1992 | Hillman et al. | |
| 5,209,904 A | 5/1993 | Forney et al. | |
| 5,242,837 A * | 9/1993 | Slovacek et al. | 436/536 |
| 5,331,109 A | 7/1994 | Buechler | 530/404 |
| 5,342,759 A | 8/1994 | Litman et al. | 435/7.92 |
| 5,356,785 A | 10/1994 | Mcmahon et al. | |
| 5,387,503 A | 2/1995 | Selmer et al. | |
| 5,447,689 A | 9/1995 | Gibboni et al. | 422/56 |
| 5,458,852 A * | 10/1995 | Buechler | 422/58 |
| 5,498,551 A | 3/1996 | de Jaeger et al. | |
| 5,569,608 A | 10/1996 | Sommer | |
| 5,635,364 A | 6/1997 | Clark et al. | 435/7.92 |
| 5,654,162 A | 8/1997 | Guire et al. | 435/7.92 |
| 5,679,526 A | 10/1997 | Buechler et al. | |
| 5,712,172 A | 1/1998 | Huang et al. | 436/518 |
| 5,719,034 A | 2/1998 | Kiser et al. | |
| 5,753,517 A | 5/1998 | Brooks et al. | |
| 5,885,527 A | 3/1999 | Buechler | |
| 5,922,615 A * | 7/1999 | Nowakowski et al. | 436/518 |
| 6,019,944 A | 2/2000 | Buechler | |
| 6,074,616 A | 6/2000 | Buechler et al. | |
| 6,106,779 A | 8/2000 | Buechler et al. | |
| 6,113,855 A | 9/2000 | Buechler | |
| 6,143,247 A * | 11/2000 | Sheppard et al. | 422/63 |
| 6,143,576 A | 11/2000 | Buechler | |
| 6,156,270 A | 12/2000 | Buechler | |
| 6,187,598 B1 * | 2/2001 | May et al. | 436/514 |
| 6,194,222 B1 * | 2/2001 | Buechler et al. | 436/518 |
| 6,238,931 B1 * | 5/2001 | Buechler et al. | 436/546 |
| 6,271,040 B1 | 8/2001 | Buechler | |

(Continued)

FOREIGN PATENT DOCUMENTS

EP    0153283 A1    8/1985

(Continued)

OTHER PUBLICATIONS

Litman et al., An internally referenced test strip immunoassay for morhpnie. Clinical Chemistry, 29(9): 1598-1603, 1983.

(Continued)

*Primary Examiner*—Lisa V Cook
(74) *Attorney, Agent, or Firm*—Wilson Sonsini Goodrich & Rosati

(57) ABSTRACT

The invention relates in part to the use of independent assay controls (IACs) for the optical communication between an assay device and an instrument in monitoring and performing assays, preferably immunoassays.

15 Claims, 19 Drawing Sheets

U.S. PATENT DOCUMENTS

| | | |
|---|---|---|
| 6,297,060 B1 | 10/2001 | Nowakowski et al. |
| 6,302,919 B1 | 10/2001 | Chambers et al. |
| 6,391,265 B1 | 5/2002 | Buechler et al. |
| 6,392,894 B1 | 5/2002 | Buechler et al. |
| 6,669,907 B1 | 12/2003 | Buechler |
| 6,767,510 B1 | 7/2004 | Buechler |
| 6,905,882 B2 | 6/2005 | Buechler |
| 7,175,992 B2 | 2/2007 | Fong |
| 7,445,941 B2 | 11/2008 | Buechler |
| 2002/0190356 A1 | 12/2002 | Buechler |
| 2003/0035758 A1 | 2/2003 | Buechler |
| 2004/0077103 A1 | 4/2004 | Buechler |
| 2005/0112782 A1 | 5/2005 | Buechler |
| 2005/0136552 A1 | 6/2005 | Buechler |
| 2005/0147531 A1 | 7/2005 | Buechler |
| 2007/0154970 A1 | 7/2007 | Buechler |

FOREIGN PATENT DOCUMENTS

| | | |
|---|---|---|
| EP | 0167340 A2 | 1/1986 |
| EP | 0253464 A1 | 1/1988 |
| EP | 0325449 A2 | 7/1989 |
| EP | 0462376 A2 | 12/1991 |
| EP | 0465266 A1 | 1/1992 |
| EP | 0462376 A3 | 8/1992 |
| EP | 0560411 A2 | 9/1993 |
| EP | 0560411 A3 | 10/1993 |
| EP | 0833157 A1 | 4/1998 |
| EP | 1046122 B1 | 11/2006 |
| GB | EP 0 810 436 A1 * | 12/1997 |
| JP | 61-501226 | 6/1986 |
| WO | WO 85/03355 | 8/1985 |
| WO | 95/08772 | 3/1995 |
| WO | 96/05476 | 2/1996 |
| WO | WO 96/10747 A1 | 4/1996 |
| WO | 97/09678 | 3/1997 |
| WO | WO 97/09620 A1 | 3/1997 |
| WO | WO 98/54567 | 12/1998 |

OTHER PUBLICATIONS

Buechler et al., Simultaneous detection of seven drugs of abuse by the Triage™ panel for drugs of abuse. Clinical Chemistry, 38(9): 1678-1684, 1992.

International Search Report dated May 26, 1999 from PCT Application No. US1999/00261.

RAMP Technology Product Literature. Response Biomedical Corporation Web site. 2008. Available at: http://www.responsebio.com/pdf/RAMP%20Technology.pdf. Accessed Jul. 7, 2008.

European Search Report for EPO Application 05076405.9, published Jul. 8, 2007.

Ellison et al., "Fluorescence-Based Mutation Detection: Single-Strand Conformation Polymorphism Analysis (F-SSCP)", Molecular Biotechnology, 5(1): 17-31, 1996.

Borrebaeck, "Antibody Engineering: A Practical Approach", Oxford University Press, 1995.

A.W. Oshi, "Matrixes and Tensors in Physics", $2^{nd}$ Edition, publication date 1984.

C.P. Tsokos, "Probability Distributors: An Introduction to Probability Theory with Applications", 1972.

Harlow et al., "Antibodies, A Laboratory Manual", Cold Spring Harbor Lab, 1988.

Huse et al., "Application of a Filamentons Phage pVIII Fusion Protein System Suitable for Efficient Production, Screening, and Mutagenesis of F(ab) Antibody Fragments", J. Immunol., 1469:3914-3920, 1992.

"Recommendation Absorption and covalent Coupling Procedures", Microparticle Reagent Optimization, Seradyn Inc., p. 91-97, published Feb. 1999.

Pierce Chemical Company Catalogue, p. Tileboard 1/92 Uniform Latex Particles. "Working with Particles", Seradyn Inc., pp. 31-40.

Buechler. U.S. Appl. No. 09/613,650, entitled "Diagnostic Devices for the Controlled Movement of Reagents without Membranes," filed Jul. 11, 2000.

* cited by examiner

METHODS FOR MONITORING THE STATUS OF ASSAYS AND IMMUNOASSAYS

RELATED APPLICATIONS

The present application is related to U.S. patent application Ser. No. 09/003,090 entitled "Immunoassay Fluorometer," Buechler et al., filed Jan. 5, 1998, now U.S. Pat. No. 6,830,731, and U.S. patent application Ser. No. 09/003,066 entitled "Media Carrier for an Assay Device," Buechler et al., filed Jan. 5, 1998, now U.S. Pat. No. 6,074,616, each of which are filed concurrently herewith and each of which are incorporated herein by reference in their entirety, including all figures, tables, and drawings.

FIELD OF THE INVENTION

This invention relates in part to the use of independent assay controls (IACs) for the optical communication between an assay device and an instrument in monitoring and performing assays, preferably immunoassays.

BACKGROUND OF THE INVENTION

The development of reliable methods for rapidly and simply measuring analytes in complex samples has become increasingly important. For example, the point of care testing in hospital emergency departments requires unskilled technicians to perform complex chemical and immunochemical assays to rapidly define the status of patients. The testing is usually performed by a nurse or an emergency room technician who are not trained as clinical chemists. The current practice of sending blood samples to the hospital laboratory is not feasible when the results are required within 30 min. The problem is thus that assay results are needed in a rapid time but the testing protocols, personnel and equipment available to the hospital emergency department are not compatible with this need. Other scenarios for obtaining rapid results through simple methods are in physicians offices, in patient homes and in field testing of pollutants and contaminants.

There is thus an unmet need for an immunoassay system that is simple, rapid and reliable.

Reliability in an immunoassay system is critical for the accurate measurement of the analyte. In an emergency room setting, the assay results can guide the physician in diagnosing and treating the patient. In a home setting, the assay result can, for example, help determine the amount and frequency of a therapeutic drug. In the field testing of pollutants and contaminants, the testing can define the extent of renovation or ground excavation needed to remove the contaminant.

Previous references regarding assay controls have not clearly defined parameters that require evaluation in assay devices. For instance, many publications simply provide examples of controls that determine the effect of non-specific binding. Some of these publications relate mainly to methods of controlling for non-specific binding and some references relate to devices that incorporate controls for non-specific binding. See, e.g., U.S. Pat. Nos. 4,533,629, 4,540,659, 4,843,000, 4,849,338, 5,342,759, 4,649,121, 4,558,013, 4,541,987, 4,472,353, and 4,099,886.

SUMMARY OF THE INVENTION

The disclosure provided herein teaches the novel use of independent assay controls (IACs) in assay devices. IAC results are not typically dependent upon assay results, however, results from one IAC may be dependent upon results from another IAC. For example, a change in a measurement in one IAC may be proportional to a change in a measurement in another IAC if the two IACs are dependent upon one another.

The term "IAC" as used herein can refer to any assay control measurement that is independent of an assay measurement. Some IACs may be independent with respect to one another and other IACs may be dependent with respect to one another. For example, a change in a first IAC measurement may occur while a change in a second IAC measurement may not occur when IACs are independent. In another example, a change in a first IAC measurement may correlate with a proportionate change in a third IAC measurement when IACs are dependent with respect to one another.

Once one or more IACs are measured, the IAC measurements can be utilized to correct assay measurements. These IACs can ensure that the results obtained from an assay detection system are accurate when assay conditions vary. Any of the IACs of the invention can be utilized to correct assay measurements. One IAC may be utilized to correct assay results, or multiple IACs may be utilized to correct assay results.

IAC for Determining the Rate of Flow

The term "rate of flow" as used herein can refer to the velocity at which a liquid solution travels through an assay apparatus. Rate of flow can be measured in terms of distance per unit time. Alternatively, rate of flow can be expressed in terms of an arbitrary unit or as a deviation from a mean value for rate of flow. A mean value for rate of flow can be determined in multiple experiments using different assay devices.

The term "assay device" as used herein can refer to any appropriate construction that allows the flow of fluids through chambers. For example, at least some chambers in an assay device may be tubes that can draw fluid by capillary action. Assay devices can be constructed from nearly any type of material, including propylene, polypropylene, and plastics, for example. An assay device may be placed in an apparatus described herein. The invention relates in part to any assay device capable of carrying out an IAC method defined herein. For example, if an IAC method requires that a second member of a binding pair (MBP) is associated with a solid phase of a diagnostic lane in an assay device, then one aspect of the invention features an assay device that comprises a second MBP associated with a solid phase in a diagnostic lane.

Thus in a first aspect, the invention features a method for determining a rate of flow of a solution through an assay device. The assay device comprises a reaction chamber and at least one diagnostic lane. The method comprises the following steps: Step (a): providing a first member of a binding pair (MBP) in the reaction chamber and a second MBP bound to a solid phase in the diagnostic lane. The first MBP comprises a label, and the first MBP and said second MBP do not appreciably bind to any IAC assay reagents in the assay device. However, the first MBP and the second MBP have specific binding affinity for one another. Step (b): detecting a signal in the diagnostic lane, where the signal is generated from the label. Step (c): determining the rate of flow of liquid through the assay device from the reaction chamber through the diagnostic lane from the amount of the signal in the diagnostic lane.

The term "reaction chamber" as used herein can refer to a portion of an assay device that contacts fluid before fluid reaches a diagnostic lane or diagnostic zone. A reaction chamber can be coextensively formed with an assay device, or alternatively, a reaction chamber can be a separate component with respect to an assay device. For example, samples and exogenously added reagents can be mixed in a test tube, which can serve as a reaction chamber. A portion or the entire contents of this test tube can then be introduced to an assay device. Fluids, biological samples, and reagents may be directly added to a reaction chamber.

The term "diagnostic lane" as used herein can refer to a portion of an assay device that harbors components comprising an IAC and an assay. A diagnostic lane may be as simple as a region allowing optical measurement of a signal. Alternatively, a diagnostic lane may comprise components that have specific binding affinity for molecules that comprise labels and molecules that comprise labels as a result of the assay process, such that binding events can be detected. In an example of an apparatus that includes capillary tubes, diagnostic lanes can embody capillary tubes aligned in parallel with respect to one dimension, or capillary tubes aligned in series with respect to one dimension.

The term "member of a binding pair (MBP)" as used herein can refer to any molecule or conglomerate of molecules that forms a complex with another molecule or conglomerate of molecules through specific binding events. Examples of MBPs are antibodies and their corresponding MBPs, as well as receptors and their corresponding MBPs. MBPs may be comprised of proteins, polypeptides, and/or small molecules, for example.

The term "do not appreciably bind" as used herein can refer to a phenomenon where interactions and/or lack of interactions between MBPs and other assay reagents do not significantly interfere with detection of a signal.

The term "assay reagents" as used herein can refer to any molecules located in an assay device or molecules exogenously added to a fluid introduced to an assay device used for measuring the presence or amount of an analyte. For example, one or more assay reagents may be incorporated into an assay device at a specific location of the assay device during the manufacture of the assay device. Such an assay reagent may serve a function of forming a complex with one or more components in a biological fluid to provide an assay result. In another example, an assay reagent may be exogenously added to a biological fluid to form a complex with one or more molecules in the fluid. Examples of analytes are cyclosporin hCG, CKMG, troponin and myoglobin.

The term "providing" or "provided" as used herein can refer to placing an assay reagent, test sample, or any other type of mixture of molecules into an assay device. An assay reagent can be provided to a reaction chamber of an assay device by delivering a solution comprising the assay reagent into the reaction chamber via a pipet, for example. In another example, an assay reagent or any other type of molecules may be provided in a diagnostic lane of an assay device by linking the molecules to a solid phase of the diagnostic lane. Methods for linking molecules to a solid support are well known to a person of ordinary skill in the art and are described further herein.

The term "test sample" as used herein can refer to any solution placed in an assay device. The solution can be extracted from a biological organism or specimen, for example. In another example, a test sample may be created in vitro and then be placed in an assay device. A test sample may also exist as a combination of these aforementioned examples.

The term "specific binding affinity" as used herein can refer to a phenomenon where a first molecule can form a complex with a second molecule with a higher probability as compared to a complex formed between the first molecule and a third molecule. In this example, the first molecule has specific binding affinity for the second molecule.

The term "label" as used herein can refer to any molecule that may be linked directly or indirectly to an MBP or reagent. A label may be linked to an MBP or reagent by covalent bonds or attractive forces such as hydrophobic, ionic, and hydrogen bond forces. A label may emit a signal, which is described hereafter.

The term "signal" as used herein can refer to any detectable parameter. Examples of these parameters include optical, electrical, or magnetic parameter current, fluorescent emissions, infrared emissions, chemiluminescent emissions, ultraviolet emissions, light emissions, and absorbance of any of the foregoing. A signal, for instance, may be expressed in terms of intensity versus distance along a diagnostic lane of an assay device. In addition, a signal may expressed in terms of intensity versus time. The term "signal" can also refer to the lack of a detectable physical parameter. The invention teaches methods, apparatus, and kits that can simultaneously measure multiple signals and multiple types of signals.

The term "amount" as used herein can refer to an increase, decrease, and/or maintenance of the intensity of physical parameter within a specific level of sensitivity. An amount of a signal can be expressed in terms of arbitrary units. For example, an increase in the amount of a signal can be detected if a signal increases by ten units and the sensitivity for measuring the signal is within one unit.

In preferred embodiments, the first MBP, second MBP, and other reagents are selected from the group consisting of binding protein, antibody, antibody fragment, protein, peptide, and organic molecule.

The term "binding protein" as used herein can refer to any protein that has specific binding affinity for one or more molecules. A binding protein can embody a protein extracted from a cell or may embody a portion of such a protein, for example. A binding protein may also be synthesized in vitro using methods well known to a person of ordinary skill in the art. A binding protein may also be a molecule that comprises multiple binding regions and/or multiple binding proteins. Binding proteins can have specific binding affinity to proteins, polypeptides, and organic molecules, for example. Examples of binding proteins are membrane receptors, non-membrane receptors, and antibodies.

The term "antibody" as used herein can refer to any molecule having amino acid similarity and/or structural similarity to the immunoglobulin class of biological molecules. An antibody may exist as an immunoglobulin extracted from a patient or animal. Alternatively, an antibody may exist as a portion of an immunoglobulin. One of these portions can be referred to as an "antibody fragment." Preferably, an antibody fragment harbors all of the hypervariable region of an immunoglobulin or a portion of the hypervariable region of an immunoglobulin. Antibodies can be extracted from properly immunized animals and can be synthesized by recombinant expression techniques in bacteria, for example.

The term "organic molecule" as used herein can refer to any molecule that comprises a covalent bond between carbon, nitrogen, oxygen, and/or sulfur. An organic molecule can range in size from carbon monoxide to large complex polymers. Organic molecules can relate to glycoside molecules. Examples of antibodies and binding proteins having specific binding affinity for organic molecules are well known in the art.

Any IAC and assay reagents and/or MBPs can be dissolved or exist in suspension in fluids and fluid analogs. Alternatively, IAC and assay reagents and/or MBPs can be linked to a solid support or a solid phase.

The term "solid support" and the term "solid phase" as used herein can refer to a non-liquid substance. A solid support may be coextensively formed with an assay device (e.g., a solid support can be a membrane or a portion of a capillary tube in an assay device), or alternatively, a solid support may be small diameter beads that flow through an assay device. Reagents may be associated with a solid support or a solid phase by covalent bonds and/or via non-covalent attractive forces such as hydrogen bond interactions, hydrophobic attractive forces, and ionic forces, for example.

In preferred embodiments, the label is selected from the group of molecules consisting of dye, fluorescence emitting dye, a chemiluminescence emitting dye, infrared emitting dye, colloidal sol, molecule that generates an electrical and/or magnetic signal, and enzyme.

The term "dye" as used herein can refer to any molecule that detectably emits or absorbs visible light, ultraviolet light, infrared light, fluorescently-derived light, chemiluminescently-derived light, and/or any other type of optically detectable parameter.

The term "colloidal sol" as used herein can refer to a partially dispersed conglomerate of molecules existing as a solid, gel, or liquid.

In another aspect, the invention features an apparatus for determining a rate of flow of a solution. An apparatus can comprise: (a) an assay device comprising a reaction chamber and at least one diagnostic lane; (b) an optical component; and (c) a signal processor. The rate of flow can be determined by providing a first member of a binding pair (MBP) in the reaction chamber, and a second MBP bound to a solid phase in the diagnostic lane. The first MBP comprises a label. Although the first MBP and the second MBP do not appreciably bind to any assay reagents in the assay device, the first MBP and the second MBP have specific binding affinity for one another. The optical component can detect a signal, where the signal is generated from the label. The signal processor can determine the rate of flow of liquid through the assay device from the reaction chamber through the diagnostic lane from the amount of the signal in the diagnostic lane.

The term "optical component" as used herein can refer to any component of an apparatus through which an assay signal passes. For example, an optical component may in part convert a fluorescent signal into an electrical signal by allowing the fluorescent signal to pass through it and into a signal processor. An optical component may be synthesized from glass, plastic, or crystalline materials. An optical component may operate in conjunction with other devices in an apparatus to convert an assay signal into another signal. An optical component may also exist as an independent device that is not fused to an apparatus of the invention, or may be coextensively formed with an assay device of the invention.

The term "signal processor" as used herein can refer to a component of an apparatus that in part modifies an assay signal. For example, a signal processor may operate in conjunction with an optical component of an apparatus to convert a fluorescent signal into an electrical signal. In another example, a signal processor may smooth an assay signal, as described hereafter. In yet another example, a signal processor may correct an assay measurement by utilizing one or more IAC measurements in an assay device. Signal processors may also be referred to as co-processors for the purposes of this invention. Processors and co-processors can operate in conjunction with a media carrier, described hereafter.

In yet another aspect, the invention features a kit for determining a rate of flow of a solution. A kit can comprise: (a) at least one of a Food and Drug Administration label and a set of instructions; and (b) an apparatus comprising: (i) an assay device comprising a reaction chamber and at least one diagnostic lane; (ii) an optical component; and (iii) a signal processor. The rate of flow can be determined by providing a first member of a binding pair (MBP) in the reaction chamber, and a second MBP bound to a solid phase in the diagnostic lane. The first MBP comprises a label. Although the first MBP and the second MBP do not appreciably bind to any assay reagents in the assay device, the first MBP and the second MBP have specific binding affinity for one another. The optical component can detect a signal, where the signal is generated from the label. The signal processor can determine the rate of flow of liquid through the assay device from the reaction chamber through the diagnostic lane from the amount of the signal in the diagnostic lane.

The term "Food and Drug Administration label" as used herein can refer to any label that has been approved by a Food and Drug Administration in the United States or any other similar administration in another country. In addition, the term may refer to a label that indicates that a certain compound or apparatus has been approved by a Food and Drug Administration in the United States or any other similar administration in another country.

The term "set of instructions" as used herein can refer to text and/or diagrams that can aid an operator of a method, apparatus, and/or kit of the invention. For example, a set of instructions may take the form of a step wise set of instructions or may exist as text on the outside of a box that contains an apparatus and/or assay device of the invention.

IAC for Determining Environmental Conditions

The term "environmental conditions" as used herein can refer to physical parameters within an assay device. For example, an IAC may determine the effect of diffusive properties of reagents that can govern the rate at which a molecule or molecules dissolve into a fluid and/or an oncoming fluid front. The proximity of IAC reagents in a reaction chamber and in an assay device, in general can define functions related to non-specific binding of label, flow mechanics, incubation time, homogeneity of the reaction mixture, and sample matrix including hematocrit of blood and the degree of heterophilic antibodies in blood of the assay. IACs of the invention can be utilized to correct assay measurements upon changing physical attributes of an assay device and/or fluids introduced to assay devices.

Hence, in another aspect, the invention features a method for determining environmental conditions in an assay device during an assay, where the assay device comprises a reaction chamber and at least one diagnostic lane. The reaction chamber comprises a first MBP and a second MBP arranged to form a solution with a test sample, where the first MBP comprises a label, and where the second MBP comprises an affinity tag. The diagnostic lane comprises an affinity tag partner (ATP), and the ATP has specific binding affinity to the affinity tag. The first MBP, the second MBP, the ATP, and the affinity tag do not appreciably bind to any IAC or assay reagents in the assay device. The first MBP and the second MBP have specific binding affinity for one another. The method comprises the steps of: (a) detecting a signal in the diagnostic lane, where the signal is generated from the label, and where the signal is detected at a location in a position where the ATP is located; and (b) determining the environmental conditions in the assay device during assay, where the environmental conditions are related to the amount of the signal in the diagnostic lane.

The term "affinity tag" as used herein can refer to a molecule linked to a reagent and/or MBP, which has specific binding affinity to an affinity tag partner. An affinity tag can be linked to a reagent and/or MBP by a covalent bond or by attractive forces described previously. An affinity tag can be linked to a reagent or MBP after the reagent or MBP is synthesized, or alternatively, an affinity tag may be linked to a reagent or MBP while the reagent or MBP is being synthesized. An affinity tag may be an organic molecule, a protein, a glycosyl moiety, or a polypeptide, for example.

The term "affinity tag partner" as used herein can refer to any molecule that has specific binding affinity to an affinity tag. An affinity tag partner may be associated with a solid phase or may exist as an unattached molecule that can freely diffuse in solution. An affinity tag partner may be an organic molecule, a polypeptide, a glycosyl moiety, or a protein, for example. Examples of affinity tag/affinity tag partner complexes that are well known in the art are hemagglutinin peptide/hemagglutinin peptide antibody complexes and avidin/biotin complexes.

In a preferred embodiment, the first MBP and the second MBP are associated with at least one of a lid and a base of the reaction chamber. In other preferred embodiments, the ATP is associated with a solid support in the diagnostic lane.

In another aspect, the method comprises the step of introducing the second MBP and the ATP to the reaction chamber, where the ATP comprises a second affinity tag, and where the diagnostic lane comprises a second ATP. The second ATP has specific binding affinity for the second affinity tag, and the second ATP and the second affinity tag do not appreciably bind to the assay reagents.

In a preferred embodiment, the first MBP, second MBP, and reagents are selected from the group consisting of binding protein, antibody, antibody fragment, protein, peptide, and organic molecule. In another embodiment, the label is selected from the group of molecules consisting of dye, fluorescence emitting dye, chemiluminescence emitting dye, infrared emitting dye, colloidal sol, molecule that generates an electrical and/or magnetic signal, and enzyme.

In another aspect, the invention features an apparatus for determining environmental conditions in an assay device during an assay. The kit can comprise: (a) the assay device; where the assay device comprises a reaction chamber and at least one diagnostic lane; (b) an optical component; and (c) a signal processor. The reaction chamber can comprise a first MBP and a second MBP arranged to form a solution with a test sample. The first MBP may comprise a label and the second MBP may comprise an affinity tag. The diagnostic lane can comprise an affinity tag partner (ATP) and the ATP may have specific binding affinity to the affinity tag. Although the first MBP, the second MBP, the ATP, and the affinity tag do not appreciably bind to any assay reagents in the assay device, the first MBP and the second MBP have specific binding affinity for one another. The optical component may detect a signal, where the signal is generated from the label. The signal processor can determine the environmental conditions in the assay device during assay, where the environmental conditions are related to an amount of the signal in the diagnostic lane.

In yet another aspect, the invention features a kit for determining environmental conditions in an assay device during an assay. A kit can comprise: (a) at least one of a Food and Drug Administration label and a set of instructions; (b) an apparatus, comprising: (i) the assay device; where the assay device comprises a reaction chamber and at least one diagnostic lane; (ii) an optical component; and (iii) a signal processor. The reaction chamber can comprise a first MBP and a second MBP arranged to form a solution with a test sample. The first MBP may comprise a label and the second MBP may comprise an affinity tag. The diagnostic lane can comprise an affinity tag partner (ATP) and the ATP may have specific binding affinity to the affinity tag. Although the first MBP, the second MBP, the ATP, and the affinity tag do not appreciably bind to any assay reagents in the assay device, the first MBP and the second MBP have specific binding affinity for one another. The optical component may detect a signal, where the signal is generated from the label. The signal processor can determine the environmental conditions in the assay device during assay, where the environmental conditions are related to an amount of the signal in the diagnostic lane.

IAC for Determining Assay Progress and Time of Completion

The term "progress" and "time of completion" as used herein can refer to monitoring the flow of molecules through an assay device. For example, a time of completion can be determined from a measure of signal intensity with respect to time and/or distance in a diagnostic lane. The rate of change of the amount of the signal at any point in the read-out or the absolute intensity of the signal at any point in the read-out can determine the progress and time of completion of the assay. These parameters are discussed in more detail hereafter.

Thus, in another aspect, the invention features a method for measuring the progress and time of completion for an assay in an assay device, where the assay device comprises a reaction chamber and at least one diagnostic lane. The method comprises the steps of: (a) providing a label in the reaction chamber; where the label does not appreciably bind to any IAC or assay reagents in the assay device; (b) detecting a signal in at least one discrete zone of the diagnostic lane, where the signal is generated from the label; and (c) determining the progress and time of completion of the assay in the assay device from at least one of: (i) a rate of change of the amount of the signal; and (ii) an absolute amount of the signal.

The term "discrete zone" as used herein can refer to a region of an assay device. For example, if a diagnostic lane exists as a capillary tube, the capillary tube can comprise multiple discrete zones. Signal intensity can be monitored independently in each zone. An assay measurement can be measured in one zone on one capillary tube, and an IAC measurement can be measured in another discrete zone in another capillary tube, or alternatively, in the same capillary tube. These examples are for illustrative purposes only and are not meant to be limiting.

The term "absolute amount of signal" as used herein can refer to a measure of signal in an assay device. The term can refer to a signal intensity measurement at any region of an assay device relating signal intensity versus time and/or distance. A region can represent one discrete measurement of signal intensity.

The term "rate of change of the amount of signal" as used herein can refer to a first derivative of signal intensity. A rate of change can be determined at one region of a measurement relating signal intensity versus distance along a diagnostic zone. In addition, a rate of change can be determined at one region of a measurement relating signal intensity versus time. These examples are not meant to be limiting and are for illustrative purposes only.

In a preferred embodiment, the derivative of the rate of change of the amount of the signal is determined. In another preferred embodiment, the absolute amount of the signal is averaged. In another preferred embodiments, the rate of change is a negative rate of change of the amount of the signal.

The term "negative rate of change" as used herein can refer to a decreasing rate of change of a signal.

In a preferred embodiment, the label is linked to an MBP. In another preferred embodiment, the MBP and reagents are selected from the group consisting of binding protein, antibody, antibody fragment, protein, peptide, and organic molecule. In other preferred embodiments, the label is selected from the group of molecules consisting of dye, fluorescence emitting dye, chemiluminescence emitting dye, infrared emitting dye, colloidal sol, molecule that generates an electrical and/or magnetic signal, and enzyme.

In another aspect, the invention features an apparatus for measuring progress and time of completion for an assay in an assay device, comprising: (a) the assay device, comprising a reaction chamber and at least one diagnostic lane; (b) an optical component; (c) a signal processor. A label can be provided in the reaction chamber and the label preferably does not appreciably bind to any assay reagents in the assay device. The optical component may detect a signal in at least one discrete zone of the diagnostic lane, where the signal is generated from the label. The signal processor can determine the progress and time of completion of the assay in the assay device from at least one of: (i) a rate of change of the amount of the signal; and (ii) an absolute amount of the signal.

In yet another aspect, the invention features a kit for measuring progress and time of completion for an assay in an assay device. The kit may comprise: (a) at least one of a Food and Drug Administration Label and a set of instructions; and (b) an apparatus, comprising: (i) the assay device, comprising a reaction chamber and at least one diagnostic lane; (ii) an optical component; (iii) a signal processor. A label may be provided in the reaction chamber and the label preferably does not appreciably bind to any assay reagents in the assay device. The optical component may detect a signal in at least one discrete zone of the diagnostic lane, where the signal is generated from the label. The signal processor can determine the progress and time of completion of the assay in the assay device from at least one of: (i) a rate of change of the amount of the signal; and (ii) an absolute amount of the signal.

IAC for Identifying Deviant Assay Results Based on Signal Intensity and/or Signal Shape The term "deviant assay results" as used herein can refer to deviance from an average shape of a signal for an IAC or an assay. A signal can be expressed as intensity versus distance in a diagnostic lane, for example. If a shape of such a signal substantially deviates from an average shape of such a signal, then the assay result may be deviant. An average shape of a signal can be determined from multiple measurements of signals in different assay devices. In addition, if a shape of an IAC signal differs from a measured signal, then the measured signal may be aberrant. Like all of the IACs of the invention, this IAC can be monitored in conjunction with any other IAC or assays of the invention.

Therefore, in one aspect, the invention features a method for determining deviant assay results in an assay device. The assay device comprises a reaction chamber and one or more diagnostic lanes. The method comprises the steps of: (a) providing a label in the reaction chamber; where the label does not appreciably bind to any assay reagents in the assay device; (b) detecting an assay signal (AS) and an independent assay control signal (IACs) in at least two discrete zones in one or more diagnostic lanes, where the signal is generated by the label; and (c) determining the deviant assay result in the assay device by comparing an intensity and/or a shape of the AS with an intensity and/or a shape of the IACs.

The assay signal and independent assay control signal can be measured in separate discrete zones. The discrete zones may exist in one capillary tube of an assay device, or may exist in different capillary tubes of an assay device.

In a preferred embodiment the label is linked to a MBP. In another preferred embodiment, the MBP and other reagents are selected from the group consisting of binding protein, antibody, antibody fragment, protein, peptide, and organic molecule. In other preferred embodiments, the label is selected from the group of molecules consisting of dye, fluorescence emitting dye, chemiluminescence emitting dye, infrared emitting dye, colloidal sol, molecule that generates an electrical and/or magnetic signal, and enzyme.

In another aspect, the invention features an apparatus for determining deviant assay results in an assay device. The apparatus can comprise: (a) the assay device, comprising a reaction chamber and at least one or more diagnostic lanes; (b) an optical component; and (c) a signal processor. A label may be provided in the reaction chamber. The label preferably does not appreciably bind to any assay reagents in the assay device. The optical component may detect an assay signal (AS) and an independent assay control signal (IACS) in at least two discrete zones in one or more diagnostic lanes, where the signal is generated by the label. The signal processor may determine the deviant assay result in the assay device by comparing a shape of the AS with a shape of the IACS.

In yet another aspect, the invention features a kit for determining deviant assay results in an assay device. The kit may comprise: (a) at least one of a Food and Drug Administration Label and a set of instructions; and (b) an apparatus, comprising: (i) the assay device, comprising a reaction chamber and at last one or more diagnostic lanes; (ii) an optical component; and (iii) a signal processor. A label may be provided in the reaction chamber. The label preferably does not appreciably bind to any assay reagents in the assay device. The optical component may detect an assay signal (AS) and an independent assay control signal (IACS) in at least two discrete zones in one or more diagnostic lanes, where the signal is generated by the label. The signal processor may determine the deviant assay result in the assay device by comparing a shape of the AS with a shape of the IACS.

Smoothing Signals

The term "smoothing" as used herein can refer to decreasing the variability in an assay signal. Smoothing is particularly useful for quantifying assay signals measured under assay conditions where the signal to noise ratio is low. A particular problem associated with such a condition is that signal processors that detect and/or quantify increases and decreases in signal intensity can be erroneously triggered. Methods of this invention that smooth signals measured in such conditions can enhance the reliability of signal processing. Smoothing can be utilized in conjunction with any other IACs of the invention. Methods for smoothing signals are well known in the art and are described hereafter.

The invention relates in part to any apparatus and computer programmable medium wholly capable or partially capable of performing a smoothing method of the invention.

Hence, in another aspect, the invention features a method for smoothing background, IAC, and assay signal determinations in an assay device, where the assay device comprises a reaction chamber and at least one diagnostic lane. The method comprises the steps of: (a) providing a label in the reaction chamber; where the label does not appreciably bind to any IAC and assay reagents in the assay device; (b) detecting the signal in the diagnostic lane, where the signal is generated from the label; and (c) smoothing the signal.

In a preferred embodiment, the label is linked to a first MBP. In another preferred embodiment, the first MBP and other reagents can be selected from the group consisting of binding protein, antibody, antibody fragment, protein, peptide, and organic molecule. In yet another preferred embodiment, the label is selected from the group of molecules consisting of dye, fluorescence emitting dye, chemiluminescence emitting dye, infrared emitting dye, colloidal sol, molecule that generates an electrical and/or magnetic signal, and enzyme.

In other preferred embodiments, the invention relates to a smoothing method comprising the step of providing a second MBP. The second MBP is located in the diagnostic lane and the first MBP and the second MBP have specific binding affinity for one another. The second MBP does not appreciably bind to any IAC and assay reagents in the assay device, except the first MBP.

In another preferred embodiment, the invention relates to a smoothing method comprising the step of providing a second MBP, where the second MBP is introduced to the reaction chamber. The first MBP and the second MBP have specific binding affinity for one another and the second MBP does not appreciably bind to any IAC and assay reagents in the assay device. The second MBP comprises an affinity tag, the diagnostic lane comprises an affinity tag partner (ATP), and the ATP has specific binding affinity to the affinity tag. The second MBP, the ATP, and the affinity tag do not appreciably bind to any IAC and assay reagents in the assay device, and the first MBP and the second MBP have specific binding affinity for one another.

In yet another preferred embodiment, the invention relates to a smoothing method comprising the step of providing a second MBP and a first affinity tag partner (ATP) to the reaction chamber. The first MBP and the second MBP have specific binding affinity for one another, and the second MBP does not appreciably bind to any IAC and assay reagents in the assay device. The second MBP comprises a first affinity tag, the first ATP has specific binding affinity to the first affinity tag, and the first ATP comprises a second affinity tag. The diagnostic lane comprises a second ATP, where the second ATP has specific binding affinity for the second affinity tag, and the second MBP, the first ATP, the second ATP, the first affinity tag, and the second affinity tag do not appreciably bind to any assay reagents in the assay device.

In other preferred embodiments, the smoothing comprises the step of averaging the signal.

In another aspect, the invention features an apparatus for smoothing assay signal determinations in an assay device. The kit may comprise: (a) the assay device, which comprises a reaction chamber and at least one diagnostic lane; (b) an optical component; and (c) a signal processor. A label may be provided in the reaction chamber, where the label does not appreciably bind to any assay reagents in the assay device. The optical component may detect the signal in the diagnostic lane, where the signal is generated from the label. The signal processor may smooth the signal.

In yet another aspect, the invention features a kit for smoothing assay signal determinations in an assay device. The kit may comprise: (a) at least one of a Food and Drug Administration Label and a set of instructions; and (b) an apparatus, comprising: (i) the assay device, comprising a reaction chamber and at least one diagnostic lane; (ii) an optical component; and (iii) a signal processor. A label may be provided in the reaction chamber, where the label does not appreciably bind to any assay reagents in the assay device. The optical component may detect the signal in the diagnostic lane, where the signal is generated from the label. The signal processor may smooth the signal.

IAC for Verifying the Location of a Detection Zone

The term "verifying a location of a detection zone" as used herein refers to an assay and/or an IAC that can indicate whether a signal detection apparatus is detecting a signal in an appropriate area of an assay device. For example, if an assay device is inappropriately positioned in a signal detection apparatus, this aspect of the invention can alert an operator of the deviant situation. Similarly, if an assay device has been manufactured inappropriately such that its detection zones are inaccurately positioned on the assay device, this aspect can alert an operator of the deviant situation. Other factors and methods for verifying the location of a detection zone are described hereafter.

The term "detection zone" as used herein can refer to any region of an assay device in which a signal can be detected. This signal can extend to IAC signals, signals that will be smoothed, and assay measurement signals, background signals, and any other type of detectable signal.

Another aspect of the invention features a method for verifying a location of a detection zone in an assay device, where the assay device comprises a reaction chamber and at least one diagnostic lane. The method comprises the steps of: (a) providing a label in the reaction chamber, where the label does not appreciably bind to any IAC and assay reagents in the assay device; (b) measuring for a signal in at least one discrete zone of the diagnostic lane, where the signal is generated by the label; and (c) verifying the location of the detection zone by a detection of the signal in the discrete zone of the diagnostic lane.

In a preferred embodiment, the label is linked to an MBP. In another preferred embodiment, the MBP and other reagents are selected from the group consisting of binding protein, antibody, antibody fragment, protein, peptide, and organic molecule. In yet another preferred embodiment the label is selected from the group of molecules consisting of dye, fluorescence emitting dye, chemiluminescence emitting dye, infrared emitting dye, colloidal sol, molecule that generates an electrical and/or magnetic signal, and enzyme.

In another aspect, the invention features an apparatus for verifying a location of a detection zone in an assay device. The apparatus may comprise: (a) the assay device, where the assay device comprises a reaction chamber and at least one diagnostic lane; (b) an optical component; and (c) a signal processor. A label can be provided in the reaction chamber; where the label does not appreciably bind to any assay reagents in the assay device. A signal may be measured by the optical component in at least one discrete zone of the diagnostic lane, where the signal is generated by the label. The location of the detection zone can be determined by the signal processor by a detection of the signal in the discrete zone of the diagnostic lane.

In yet another aspect, the invention features a kit for verifying a location of a detection zone in an assay device. The apparatus may comprise: (a) at least one of a Food and Drug Administration label and a set of instructions; and (b) an apparatus, comprising: (i) the assay device, where the assay device comprises a reaction chamber and at least one diagnostic lane; (ii) an optical component; and (iii) a signal processor. A label can be provided in the reaction chamber; where the label does not appreciably bind to any assay reagents in the assay device. A signal may be measured by the optical component in at least one discrete zone of the diagnostic lane, where the signal is generated by the label. The location of the detection zone can be determined by the signal processor by a detection of the signal in the discrete zone of the diagnostic lane.

Correction of Assay Measurements by Utilizing IACs

The invention teaches methods, computer programmable media, and apparatus useful for correcting assay measurements by utilizing IACs provided herein. As discussed previously, assay results can deviate due to variations in parameters that an assay operator cannot easily control, such as variations in assay temperature and variations in sample viscosity and chemical and biochemical composition.

Measurement of an IAC of the invention can be utilized to correct a measured assay result so that uniform assay results can be measured despite variations in conditions that are beyond an assay operator's control. Mathematical derivations for correcting measured assay results are described hereafter with respect to utilizing one, two, or multiple IACs in a single assay.

Different methods, computer programmable media, and apparatus can be utilized to correct assay measurements with one or more IAC measurements. The type of method, computer programmable medium, and apparatus used to correct an assay measurement can depend upon the relation of particular parameters of an assay. For example, the relationship between (i) a constant ($\beta$) that modifies deviations in IAC measurements and (ii) mean values for assay measurements, can determine which methods, computer programmable media, and apparatus are used to correct an assay measurement. Specifically, certain methods, computer programmable media, and apparatus may be utilized if these two parameters are related in non-linear manner, while other methods, computer programmable media, and apparatus may be utilized if these two parameters are related in a linear manner. These parameters are defined in more detail hereafter.

The term "constant" as used herein can refer to any constant that is multiplied by a measurement or determination of the invention. A measurement of the invention can be an IAC deviation or a mean value of multiple assay measurements, for example. As mentioned previously, IAC deviations can be multiplied by a constant in methods useful for correcting a measured assay result. Some constants utilized herein are referred to as $\beta$ and $\Gamma$. $\beta$ and $\Gamma$ can be functions of test values and IAC values. However, in the teachings that follow, $\beta$ and $\Gamma$ can be solved at specific values for test assay measurements and IAC measurements and therefore can be referred to as constants. $\beta$ can be determined, for example, (i) by guessing a value of the constant, (ii) by solving for a slope value of a linear regression relating assay measurement deviations and control measurement deviations, (iii) by solving a matrix function for a matrix consisting of assay measurement deviations and control measurement deviations, and (iv) by solving equations that maximize a coefficient of correlation and minimize the quotient of the standard deviation and the mean value of corrected assay measurements. Multiple examples of mathematical means for solving matrix functions and coefficients of correlations are well known to a person of ordinary skill in the art. See, e.g., *Matrixes and Tensors in Physics* ($2^{nd}$ edition), A. W. Joshi, and *Probability Distributions: An Introduction to Probability Theory with Applications,* 1972, C. P. Tsokos. Applications involving linear regression analysis and matrix function analysis are also described in more detail hereafter. $\Gamma$ can be determined, for example, from the slope of a linear regression analysis for a plot relating $\beta$ and mean value of assay measurements. Each $\beta$ may be determined from a set of assay devices. Each mean value of assay measurements can be determined from a set of assay devices. The subscript "i" is sometimes used herein to denote a discrete set of assay devices.

Utilization of IACs When a Constant That Modifies Deviations in IAC Measurements Varies Non-linearly with Mean Values of Assay Measurements The invention relates in part to methods, computer programmable media, and apparatus that are useful for determining corrected assay results from measured assay results under assay conditions where a constant ($\beta$) that modifies deviations in IAC results varies in a non-linear fashion with a mean value of multiple assay measurements. Mathematical equations depicting the relationship between corrected assay results, measured assay results, IAC results, and constants that modify IAC results are defined hereafter, with respect to these conditions.

When IACs are dependent upon one another, the constant can be determined by solving a matrix function comprising assay result measurements and IAC measurements. When IACs are not dependent upon one another, the constant can be determined by solving for the slope of a linear regression analysis of a plot relating deviations in IAC measurements and deviations in assay measurements. Deviations in assay and IAC measurements can be determined from measurements using multiple assay devices. Discrete mathematical equations and corresponding experimental methods can be determined for assay devices that employ multiple IACs, two IACs, or one IAC for the correction of an assay result. These mathematical equations are defined hereafter.

The mathematical operations described herein, including determinations of sums, differences, products, and quotients are well known to person of ordinary skill in the art. Additionally, linear regression analysis, solving matrix algebra functions, and the creation of plots, are techniques well known to a person of ordinary skill in the art.

The term "difference" and "differences" as used herein can refer to mathematical functions in which one quantity is subtracted from another. The quantity that is subtracted from another is independent of the manner in which the difference is expressed herein. For example, the description "the difference between A and B" can be expressed as "A subtracted from B" and "B subtracted from A." The latter interpretation is preferred for the purposes of the invention.

The term "quotient" as used herein can refer to mathematical functions in which one quantity is divided by another quantity. The quantity that is divided by another quantity is independent of the manner in which the quotient is expressed herein. For example, the description "the quotient between A and B" can be expressed as "A divided by B" and "B divided by A." The former interpretation is preferred for the purposes of the invention.

The term "multiple measurements" as used herein can refer to a number of assay and/or IAC measurements that may be utilized to correct an assay measurement. The subscript "i" can be utilized to denote each assay device. The number of assay devices can be variable with respect to a particular type of assay measurement as well as a particular IAC. Although the mathematical relations provided by the invention relate to an infinite number of assay devices, the number of assay devices preferably span from two to one million. For example, if one type of assay measurement is determined in ten assay devices, the measurement in the fifth device can be referred to as $T_i$ where i is equal to five. As another example, and as described hereafter, assay measurements can be determined in multiple assay devices, a mean value of assay measurements can be determined, a range of assay deviations can be calculated by subtracting the calculated mean value from each assay measurement, and constants can be determined from plots of these assay deviations. The subscript "i" can reflect each assay device as well as each IAC utilized to generate multiple assay measurements as well as IAC measurements.

A discrete IAC can be defined by the subscript "j." The mathematical operations provided herein allow for an infinite number of discrete IACs to be utilized for the correction of an assay signal. However, less than ten IACs are preferably measured in an assay device for the correction of an assay result. In an example, if ten IACs are measured in one assay device, the fifth IAC measured in each assay device can be referred to as $IAC_j$, where j is equal to 5. Each IAC deviation for each discrete IAC can be modified by a constant to correct a measured assay result.

The terms "IAC deviation" and "$\delta IAC$" as used herein can refer to a mathematical difference between a mean value of multiple IAC measurements for each discrete IAC in an assay device and the multiple IAC measurements themselves. Multiple IAC measurements can be determined in multiple assay devices. The multiple IAC measurements can be performed previous to the assay measurement that may be corrected.

The terms "assay measurement deviations" and "$\delta T$" as used herein can refer to a mathematical difference between a mean value of multiple assay measurements and the multiple assay measurements themselves. The multiple assay measurements can be determined in multiple assay devices. The multiple assay measurements can be performed previous to the assay measurement that may be corrected.

The term "matrix function" as used herein can refer to a mathematical matrix function or an inverse matrix function. Matrix functions and inverse matrix functions are described in more detail hereafter.

Thus in one aspect, the invention features a method for determining a corrected assay result ($T_c$) from a measured assay result ($T_m$) and multiple (j) measured control assay results ($IAC_j$). The method comprises the steps of: (a) measuring the $T_m$ and each $IAC_j$ in an assay device; (b) determining a difference between each $IAC_j$ and a mean value ($IAC_{jave}$) of multiple $IAC_j$ measurements ($IAC_{ji}$); (c) determining a product by multiplying each difference of step (b) by a constant ($\beta_j$); (d) determining a sum of every $j^{th}$ product; and (e) subtracting the sum from $T_m$.

In a preferred embodiment, each $\beta_j$ is determined by a matrix function comprising each $\delta T$ and each $\delta IAC_j$. In another preferred embodiment, each $\beta_j$ is determined from a slope of a linear regression of a plot, where the plot is differences ($\delta T_i$) between multiple assay result measurements ($T_i$) and a mean value of $T_i$ ($T_{ave}$) versus differences between $IAC_{ji}$ and $IAC_{jave}$.

In yet another preferred embodiment, the method is performed when one IAC is utilized to correct an assay result. In other preferred embodiments, two IACs are utilized to correct an assay result. A person of ordinary skill in the art can readily adapt the methods, computer programmable media, apparatus, and mathematical relations taught herein to effect these preferred embodiments.

In another aspect, the invention features a computer programmable medium embodying a program of instructions for causing a processor to perform a method for determining a corrected assay result ($T_c$) from a measured assay result ($T_m$) and multiple (j) measured control assay results ($IAC_j$). The method comprises the steps of: (a) measuring said $T_m$ and each $IAC_j$ in an assay device; (b) determining a difference between each $IAC_j$ and a mean value ($IAC_{jave}$) of multiple $IAC_j$ measurements ($IAC_{ji}$); (c) determining a product by multiplying each difference of step (b) by a constant ($\beta_j$); (d) determining a sum of every $j^{th}$ product; and (e) subtracting the sum from $T_m$.

In yet another aspect, the invention features an apparatus useful for performing the method defined in the previous paragraph.

Preferred embodiments of the invention relate to utilizing any signal measurements and IAC measurements described herein for use in methods, computer programmable media, and apparatus useful for correcting a measured assay result.

Utilization of IACs When a Constant That Modifies Deviations in IAC Measurements Varies Linearly with Mean Values of Assay Measurements The invention relates in part to methods, computer programmable media, and apparatus that are useful for determining corrected assay results from measured assay results under assay conditions where a constant ($\beta$) that modifies deviations in IAC results varies in a linear fashion with a mean value of multiple assay measurements. Mathematical equations depicting the relationship between corrected assay results, measured assay results, IAC results, and constants that modify IAC results are defined hereafter, with respect to these conditions.

As described previously, when IACs are dependent upon one another, the constant can be determined by solving a matrix function comprising assay result measurements and IAC measurements. When IACs are not dependent upon one another, the constant can be determined by solving for the slope of a linear regression analysis of a plot relating deviations in IAC measurements and deviations in assay measurements. Deviations in assay and IAC measurements can be determined from measurements using multiple assay devices. Discrete mathematical equations and corresponding experimental methods can be determined for assay devices that employ multiple IACs, two IACs, or one IAC for the correction of an assay result. These mathematical equations are defined hereafter.

Hence, in one aspect, the invention features a method for determining a corrected assay result ($T_c$) from a measured assay result ($T_m$) and multiple (j) measured control assay results ($IAC_j$). The method comprises the steps of: (a) measuring the $T_m$ and each $IAC_j$ in an assay device; (b) determining a difference ($\delta IAC_j$) between each $IAC_j$ and a mean value ($IAC_{jave}$) of multiple $IAC_j$ measurements ($IAC_{ji}$); (c) determining a product by multiplying each difference of step (b) by a constant ($\Gamma_j$); (d) determining a sum of the integer 1 and every $j^{th}$ product; (e) determining a quotient between the sum and the $T_m$.

In a preferred embodiment each $\Gamma_j$ is a slope of a linear regression of a plot, where the plot is multiple $\beta_j$ determinations versus mean values ($T_{ave}$) of multiple assay result measurements ($T_i$). In another preferred embodiment, each $\beta_j$ is determined by a matrix function comprising each $\delta T$ and each $\delta IAC_j$. In other preferred embodiments, each $\beta_j$ is determined from a slope of a linear regression of a plot, where the plot is differences ($\delta T$) between multiple assay result measurements ($T_i$) and a mean value of $T_i$ ($T_{ave}$) versus differences between $IAC_{ji}$ and $IAC_{jave}$.

In a preferred embodiment, the method is performed when one IAC is utilized to correct an assay result. In another preferred embodiment, two IACs are utilized to correct an assay result. A person of ordinary skill in the art can readily adapt the methods and mathematical relations taught herein to effect these preferred embodiments.

In another aspect, the invention features a computer programmable medium embodying a program of instructions for causing a processor to perform a method for determining a corrected assay result ($T_c$) from a measured assay result ($T_m$) and multiple (j) measured control assay results ($IAC_j$). The method comprises the steps of: (a) measuring the $T_m$ and each $IAC_j$ in an assay device; (b) determining a difference ($\delta IAC_j$) between each $IAC_j$ and a mean value ($IAC_{jave}$) of multiple $IAC_j$ measurements ($IAC_{ji}$); (c) determining a product by multiplying each difference of step (b) by a constant ($\Gamma_j$); (d) determining a sum of the integer 1 and every $j^{th}$ product; (e) determining a quotient between the sum of multiple entities and the $T_m$.

In yet another aspect, the invention features an apparatus useful for performing the method described in the previous paragraph.

Other methods exist for correcting an assay result when a constant that modifies deviations in IAC results varies in a linear fashion with a mean value of multiple assay measurements. Hence, in another aspect, the invention features a method for determining a corrected assay result ($T_c$) from a measured assay result ($T_m$) and multiple (j) measured control assay results ($IAC_j$). The method comprises the steps of: (a) measuring the $T_m$ and each $IAC_j$ in an assay device; (b) determining a function of each $IAC_j$; (c) determining a sum of the integer 1 and each function; and (d) determining a quotient between $T_m$ and the sum.

The term "function" as used herein can refer to a mathematical operation that can be expressed in terms of a power series expansion of differences ($\delta IAC_j$) between each $IAC_j$ and a mean value ($IAC_{jave}$) of multiple $IAC_j$ measurements ($IAC_{ji}$). A power series expansion is well known to a person of ordinary skill in the art.

In a preferred embodiment, the method is performed when one IAC is utilized to correct an assay result. In another preferred embodiment, two IACs are utilized to correct an assay result. A person of ordinary skill in the art can readily adapt the methods and mathematical relations taught herein to effect these preferred embodiments.

In another aspect, the invention features a computer programmable medium embodying a program of instructions for causing a processor to perform a method for determining a corrected assay result ($T_c$) from a measured assay result ($T_m$) and multiple (j) measured control assay results ($IAC_j$). The method comprises the steps of: (a) measuring the $T_m$ and each $IAC_j$ in an assay device; (b) determining a function of each $IAC_j$; (c) determining a sum of the integer 1 and each function; and (d) determining a quotient between $T_m$ and the sum.

In yet another aspect, the invention features an apparatus that is useful for performing the method defined in the previous paragraph.

When one IAC is measured, another method can be utilized to correct an assay measurement when IAC measurements vary proportionately with assay measurements.

Hence, in another aspect, the invention features a method for determining a corrected assay result ($T_c$) from a measured assay result ($T_m$) and a measured independent assay control result (IAC). The method comprises the steps of: (a) measuring the $T_m$ and the IAC in an assay device; (b) determining a quotient between a mean value ($IAC_{ave}$) of multiple IAC measurements ($IAC_i$) and the IAC; and (c) determining a product by multiplying the quotient of step (b) by said $T_m$.

In another aspect, the invention features a computer programmable medium embodying a program of instructions for causing a processor to perform a method for determining a corrected assay result ($T_c$) from a measured assay result ($T_m$) and a measured independent assay control result (IAC). The method is identical to that defined in the previous paragraph.

In yet another aspect, the invention features an apparatus useful for determining a corrected assay result ($T_c$) from a measured assay result ($T_m$) and a measured independent assay control result (IAC). The apparatus is useful for performing the method defined in the previous paragraph.

As determined previously, preferred embodiments of the invention can relate to utilizing any signal measurements and IAC measurements described herein for use in methods, computer programmable media, and apparatus useful for correcting a measured assay result.

Correcting Assay Measurements by Utilizing Apparatus

The invention relates in part to methods for correcting assay measurements by measuring IACs in apparatus. Any of the IAC and smoothing methods, apparatus, and kits defined herein can be utilized for the correction of assay measurements. Any combination of IACs and smoothing methods, apparatus, and kits can be combined or utilized individually. For example, an apparatus useful for smoothing signals and an apparatus useful for correcting an assay measurement by monitoring the rate of flow can exist as one apparatus or can be combined into one apparatus useful for correcting assay measurements.

Embodiments of the invention relate to apparatus that can measure assay signals and/or IAC signals by an optical device within the apparatus. Optical apparatus are defined in U.S. patent application Ser. No. 09/003,090, entitled "Immunoassay Fluorometer," Buechler et al., filed Jan. 5, 1998, now U.S. Pat. No. 6,830,731.

In a preferred embodiment, an apparatus of the invention comprises a media carrier. The term "media carrier" is fully defined in U.S. patent application Ser. No. 09/003,066, entitled "Media Carrier for an Assay Device," Buechler et al., filed Jan. 5, 1998, now U.S. Pat. No. 6,074,616. A media carrier may comprise computer programmable media defined herein.

Hence, the invention relates in part to apparatus that are capable of: (i) measuring an assay signal in an assay device, and (ii) measuring one or more IAC signals defined herein, (iii) smoothing the signals, and (iv) correcting the assay result by utilizing the IAC signal or signals. The assay signal and IAC signal or signals can be measured using an optical component of the apparatus and the signals can be smoothed by a processor or co-processor component of the apparatus. The processor or any co-processor can correct the assay measurement according to the IAC signal or signals. The processors or co-processors of the apparatus can operate in conjunction with one or more media carriers.

The summary of the invention described above is not limiting and other features and advantages of the invention will be apparent from the following detailed description of the preferred embodiments, as well as from the claims.

BRIEF DESCRIPTION OF THE FIGURES

Certain figures illustrate signal measurement for particular embodiments of the invention.

Other figures illustrate particular embodiments of IACs of the invention.

Figure 1:
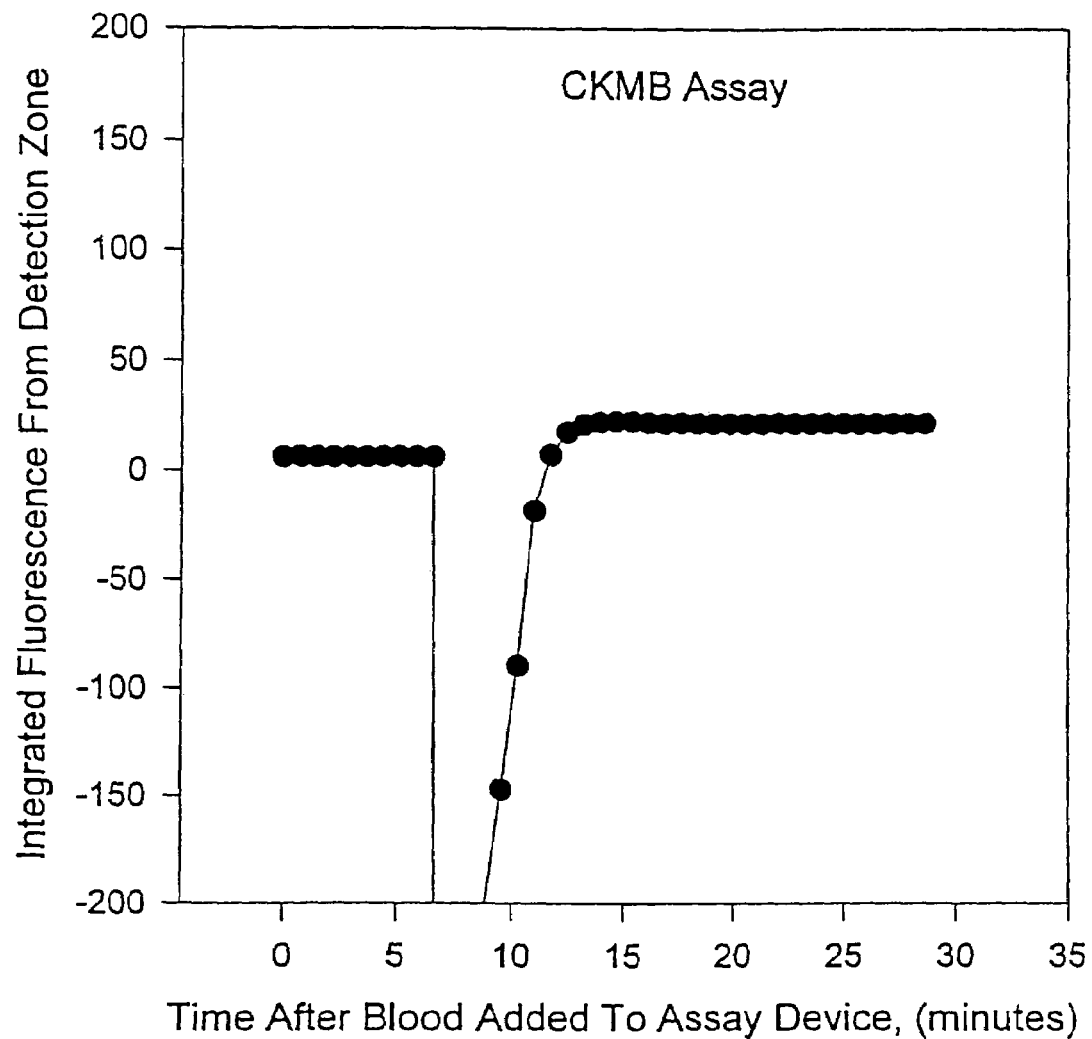
FIG. 1 is a time dependent profile of an integrated CKMB assay signal.
Figure 2:
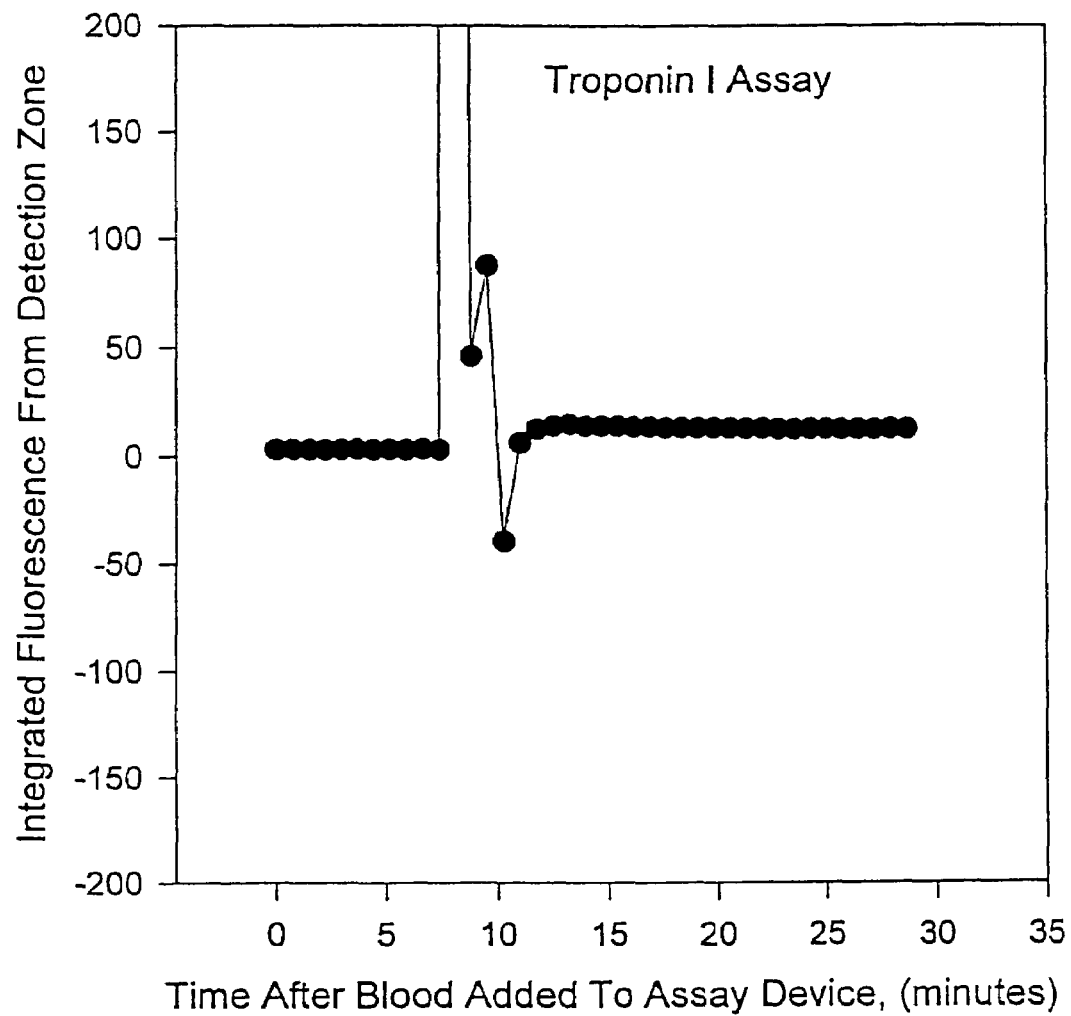
FIG. 2 is a time dependent profile of an integrated troponin I assay signal.
Figure 3:
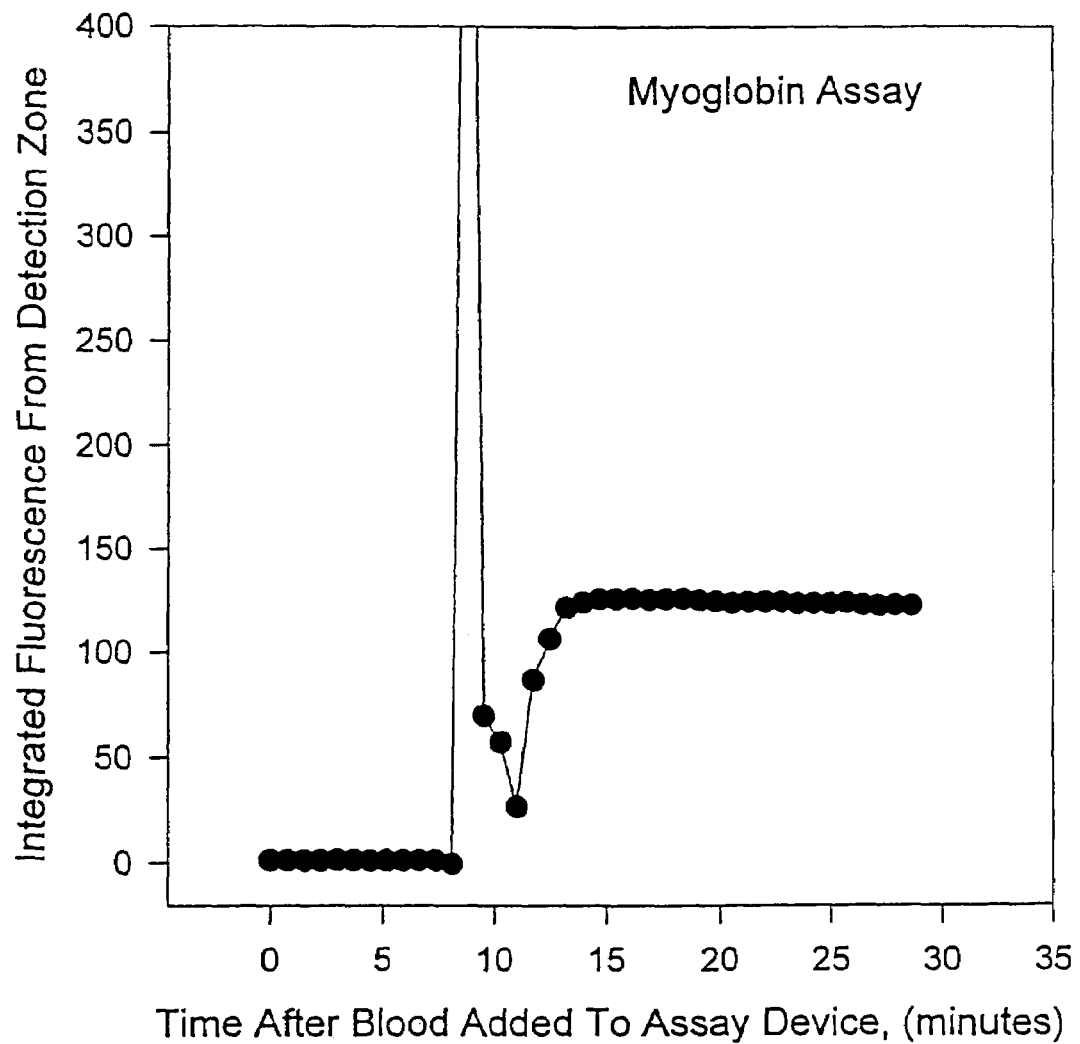
FIG. 3 is a time dependent profile of an integrated myoglobin assay signal.
Figure 4:
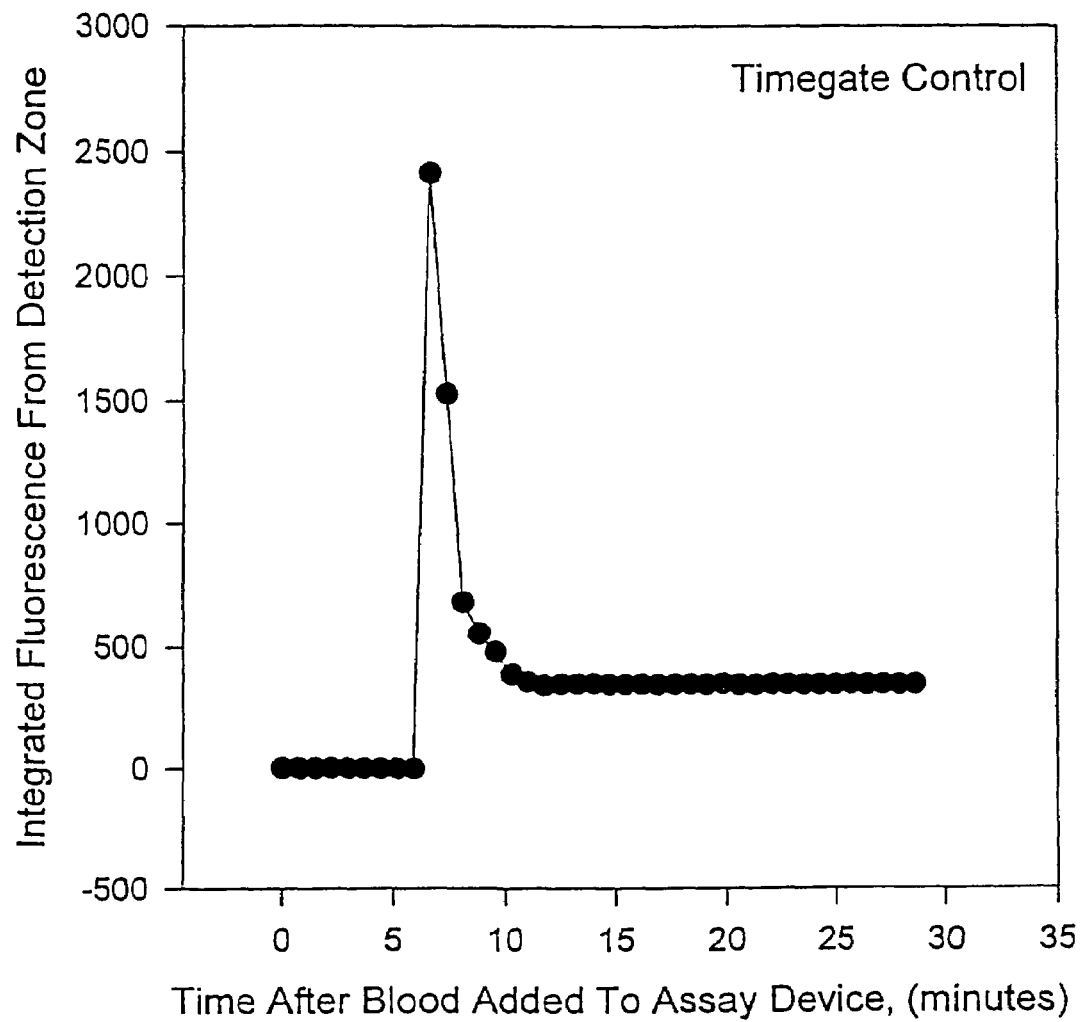

FIG. 4 is a time dependent profile of the integrated timegate IAC signal.

Figure 5:
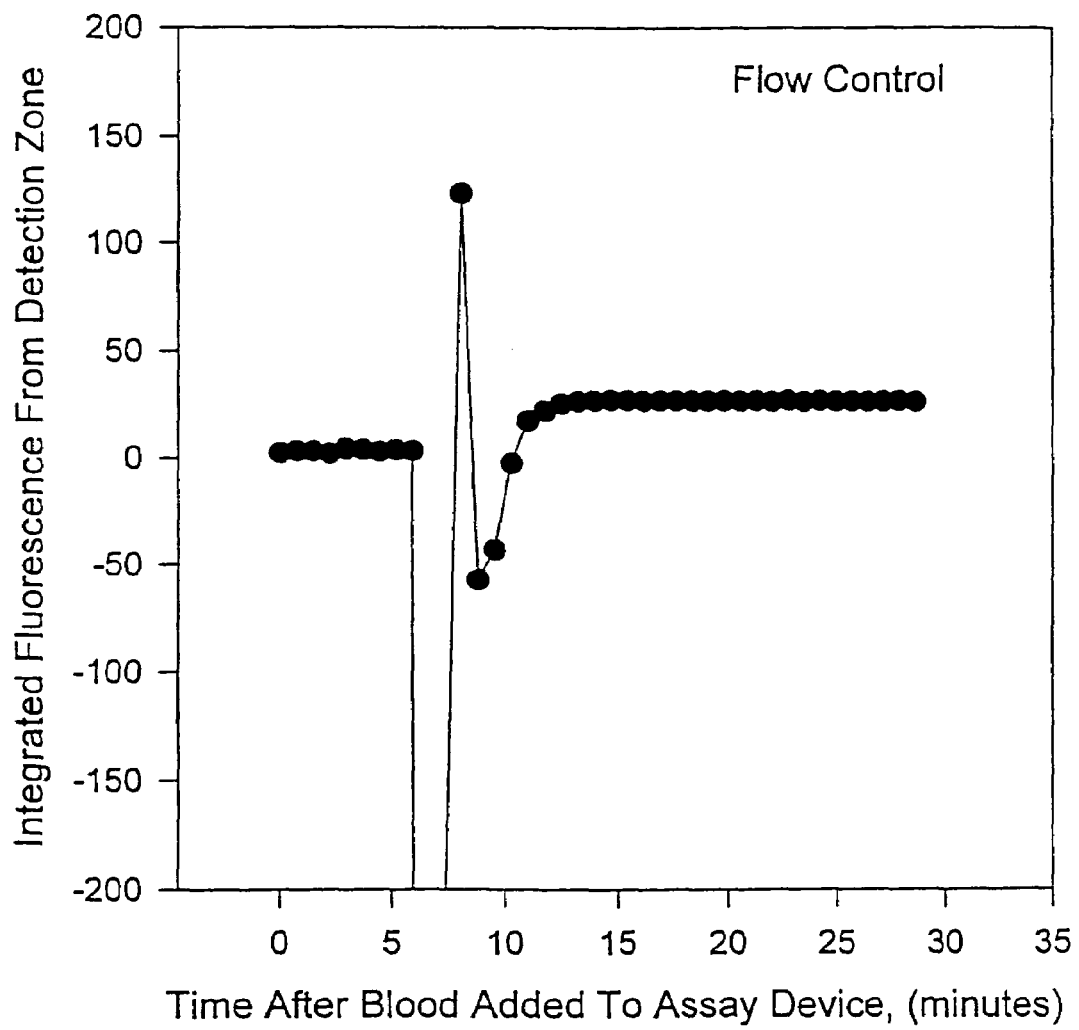

FIG. 5 is a time dependent profile of an integrated flow IAC signal.

Figure 6:
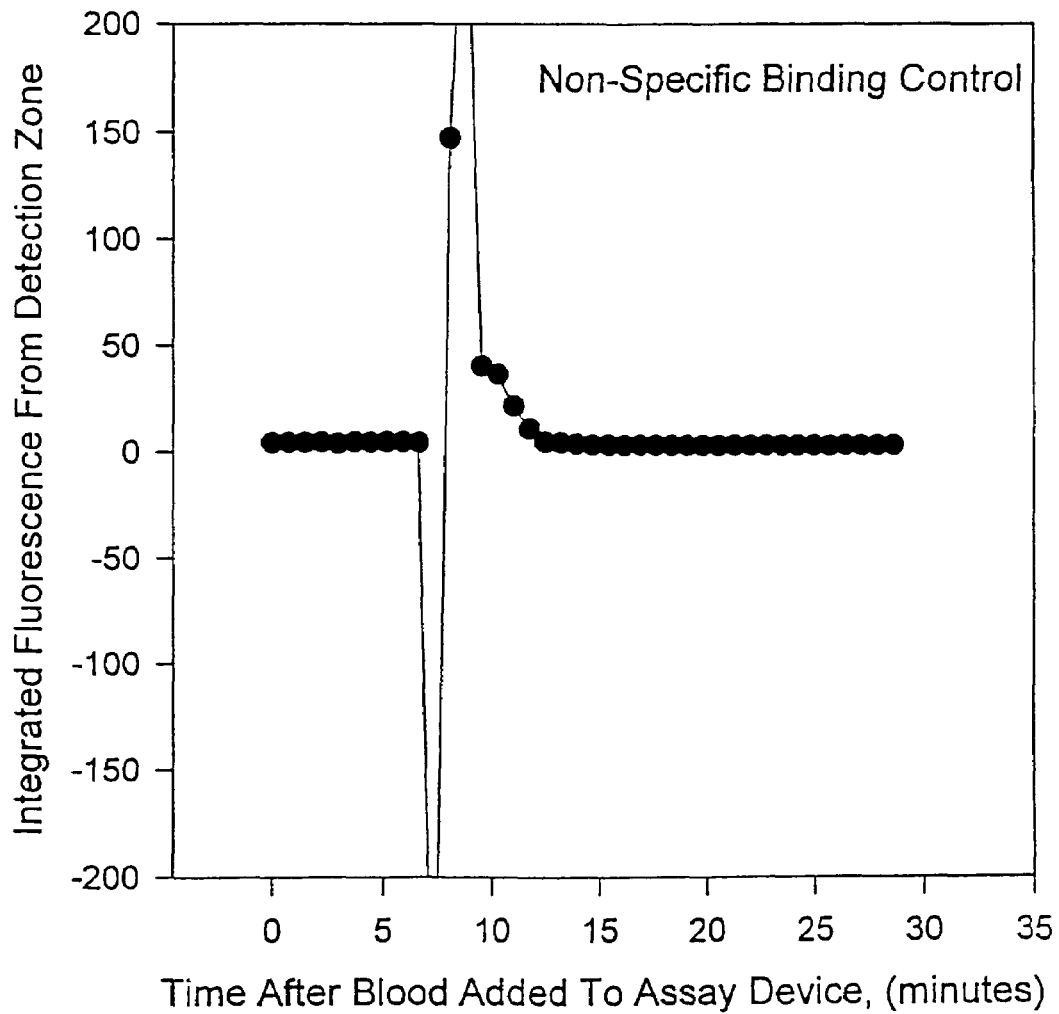

FIG. 6 is a time dependent profile of an integrated non-specific binding IAC signal.

Figure 7:
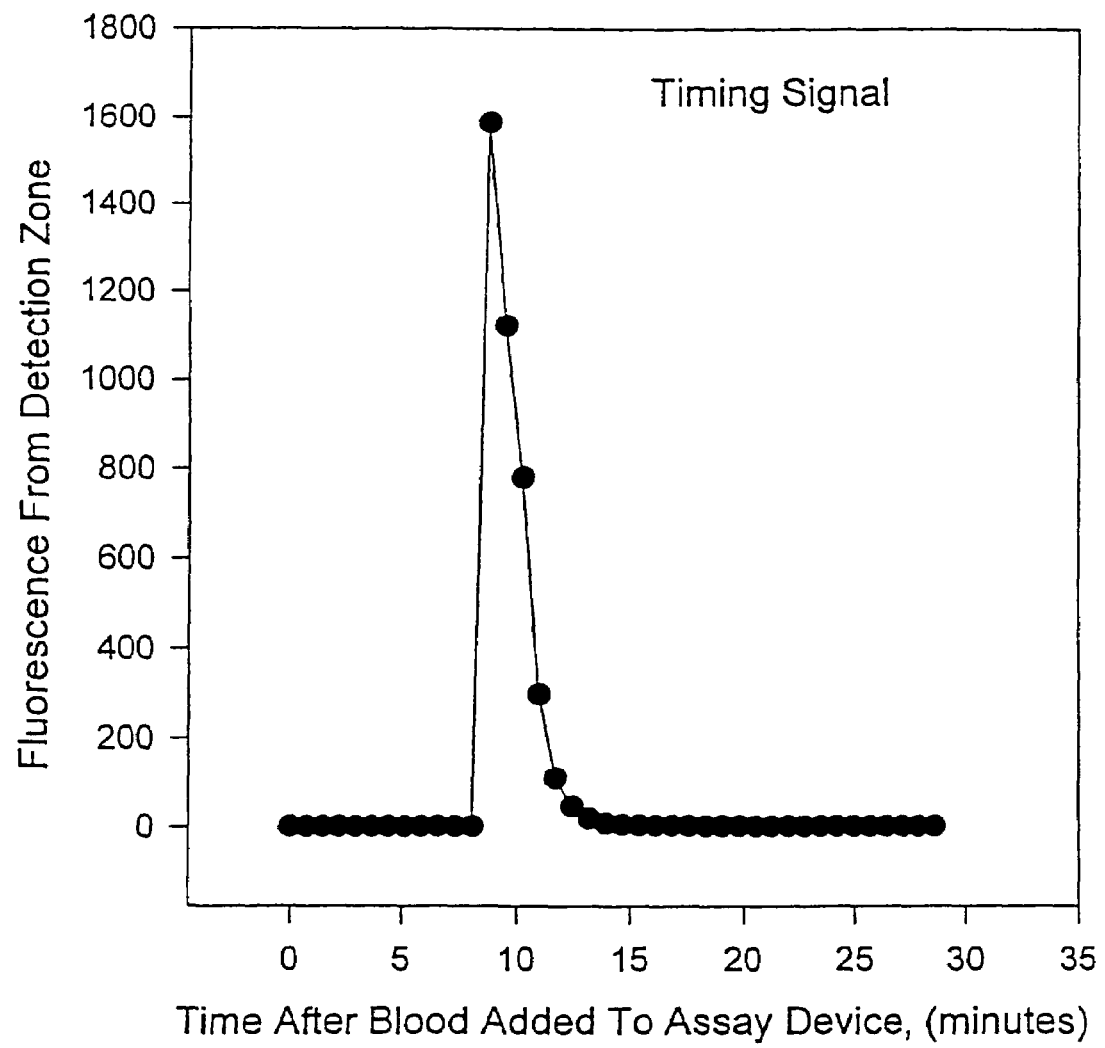

FIG. 7 is a time dependent profile of a timing IAC signal.

Figure 8:
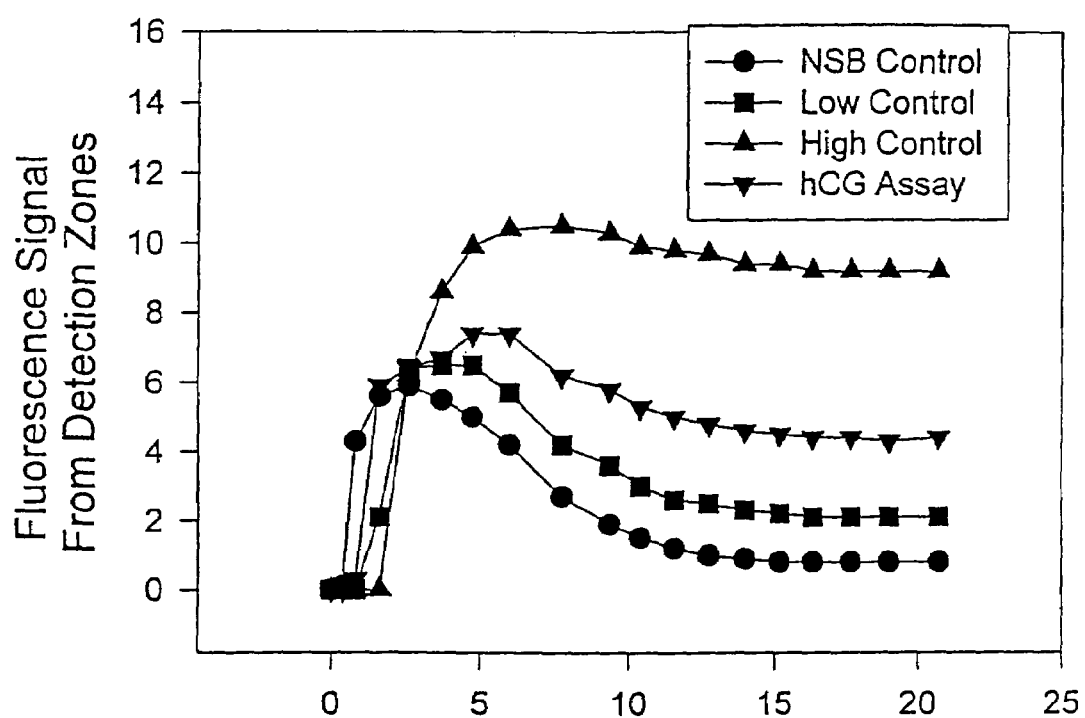

FIG. 8 is a time dependent profile of an IAC concerning human chorionic gonadotrophin (hCG) signals.

Figure 9:
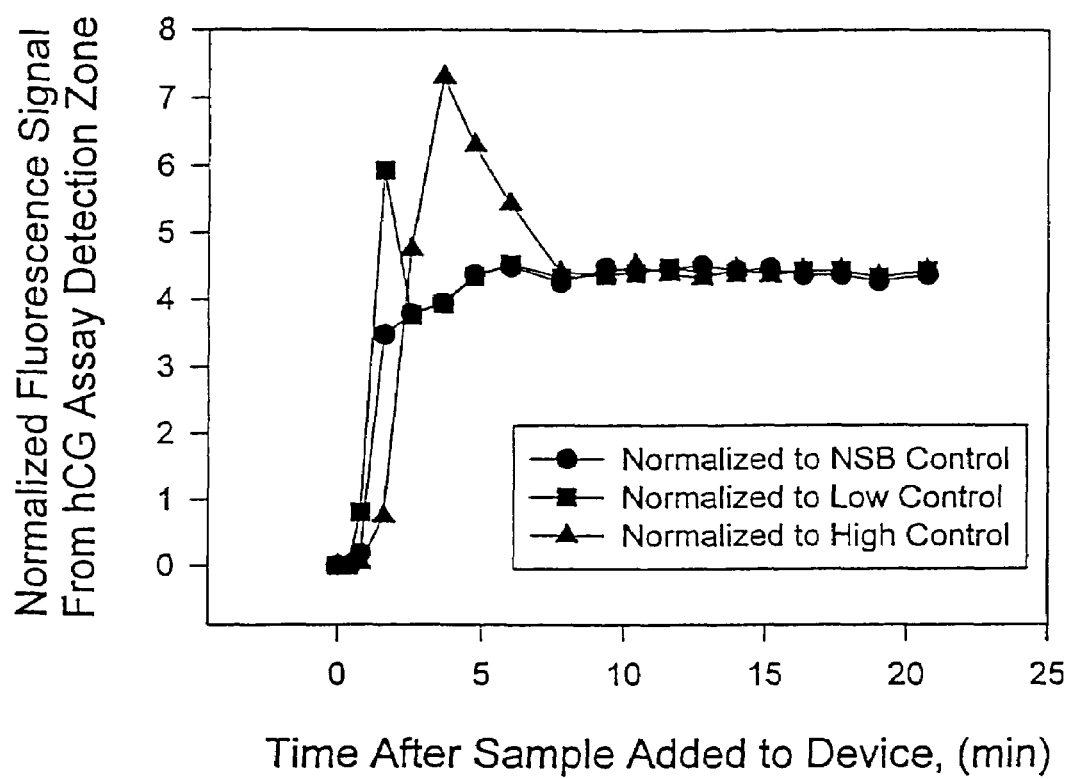

FIG. 9 is a time-dependent profile of normalized hCG assay signals.

Some figures illustrate embodiments of signal processing IACs of the invention.

Figure 10:
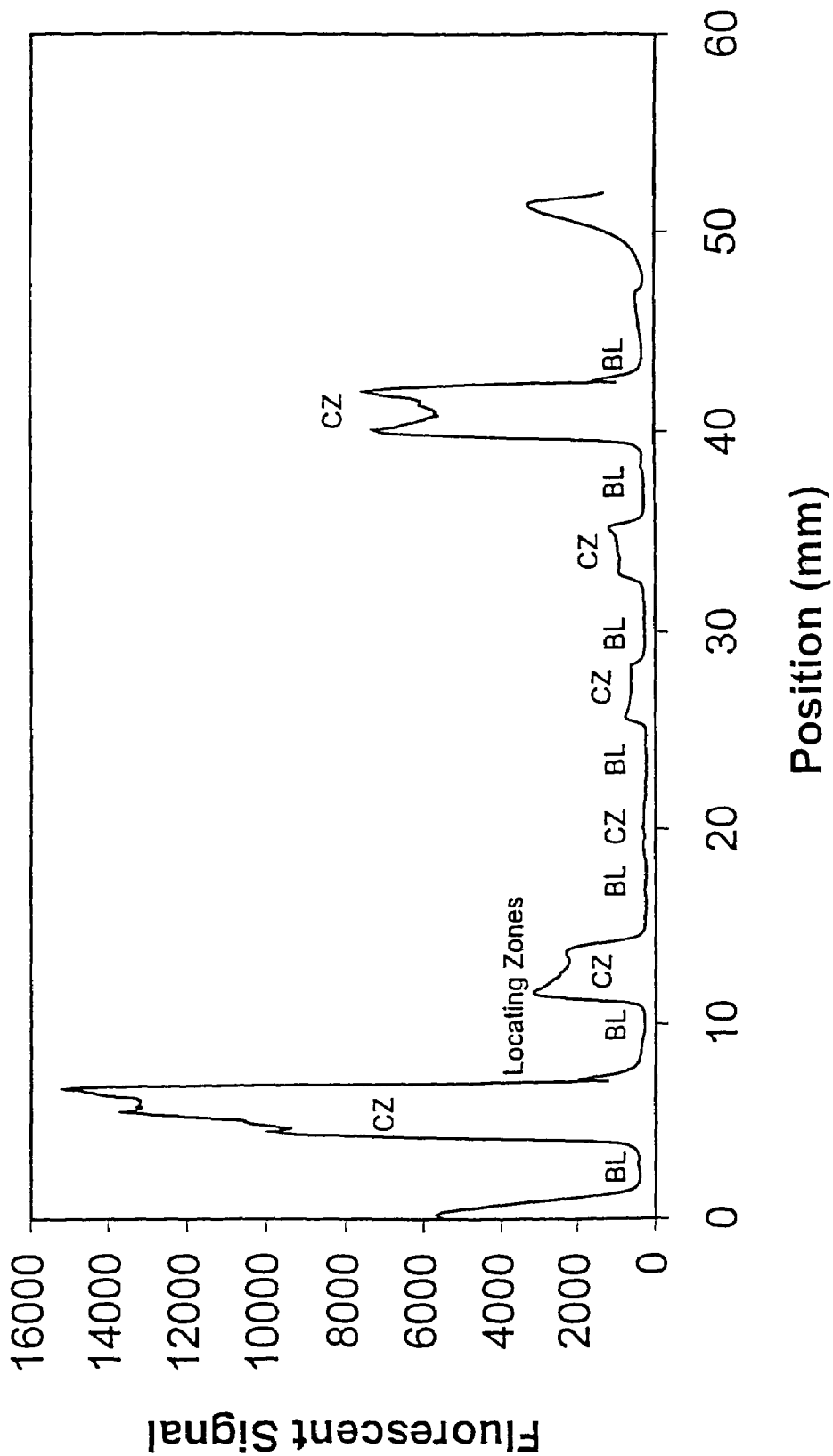

FIG. 10 depicts specific time zones in an assay device diagnostic lane.

Figure 11:
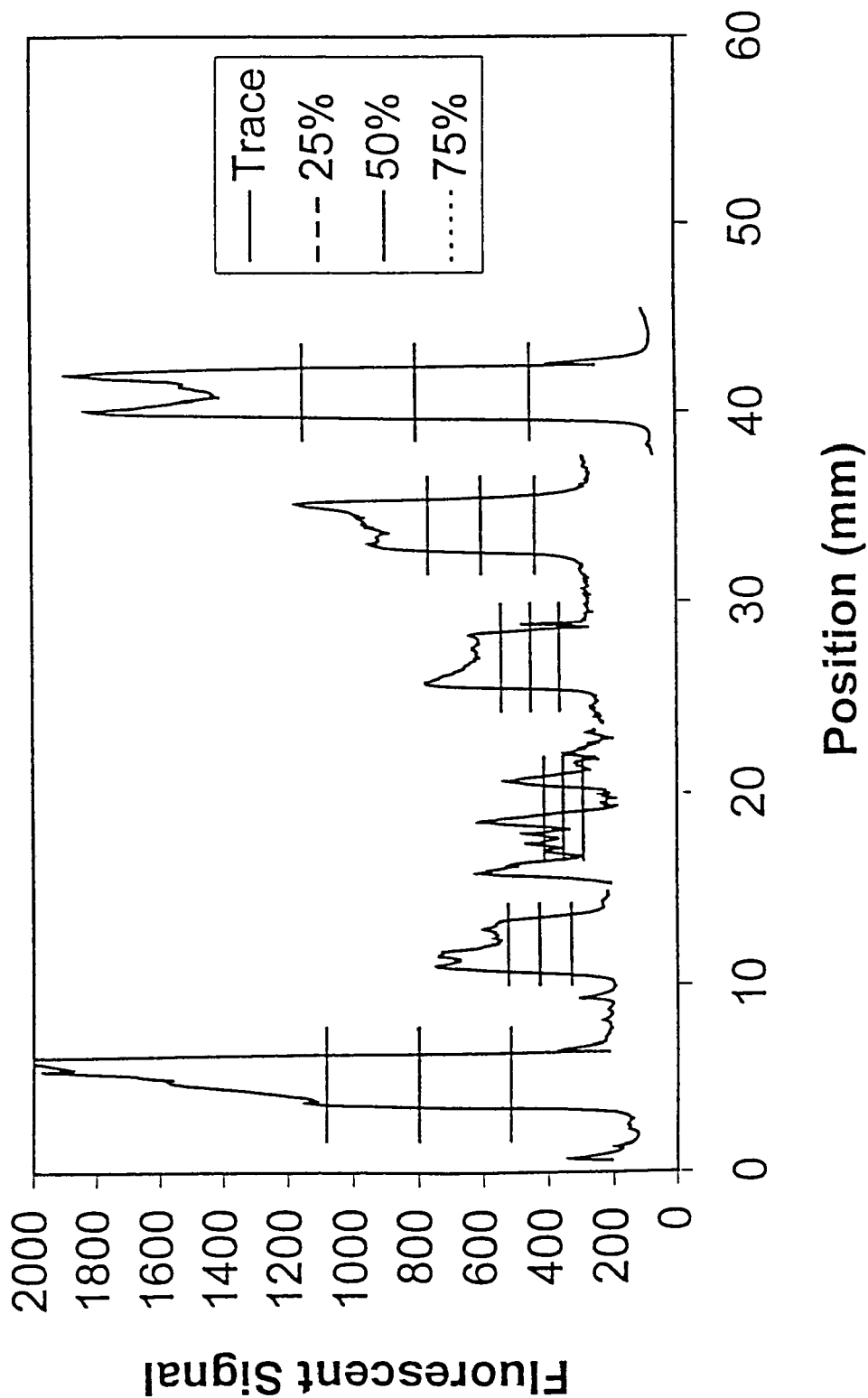

FIG. 11 illustrates zone determination and identification in a diagnostic lane of an assay device.

Figure 12:
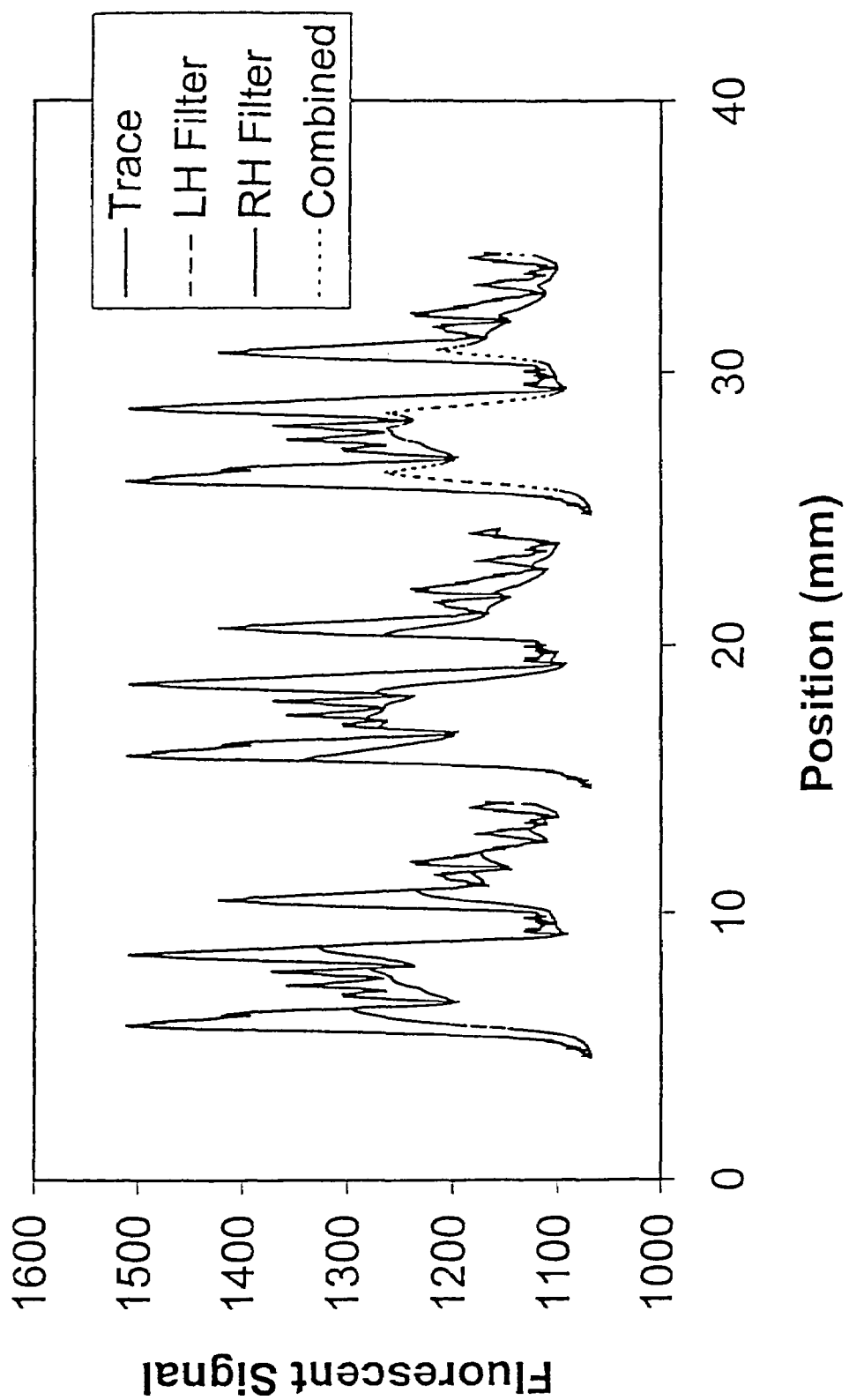

FIG. 12 depicts the effects of bidirectional filtering functions.

Figure 13:
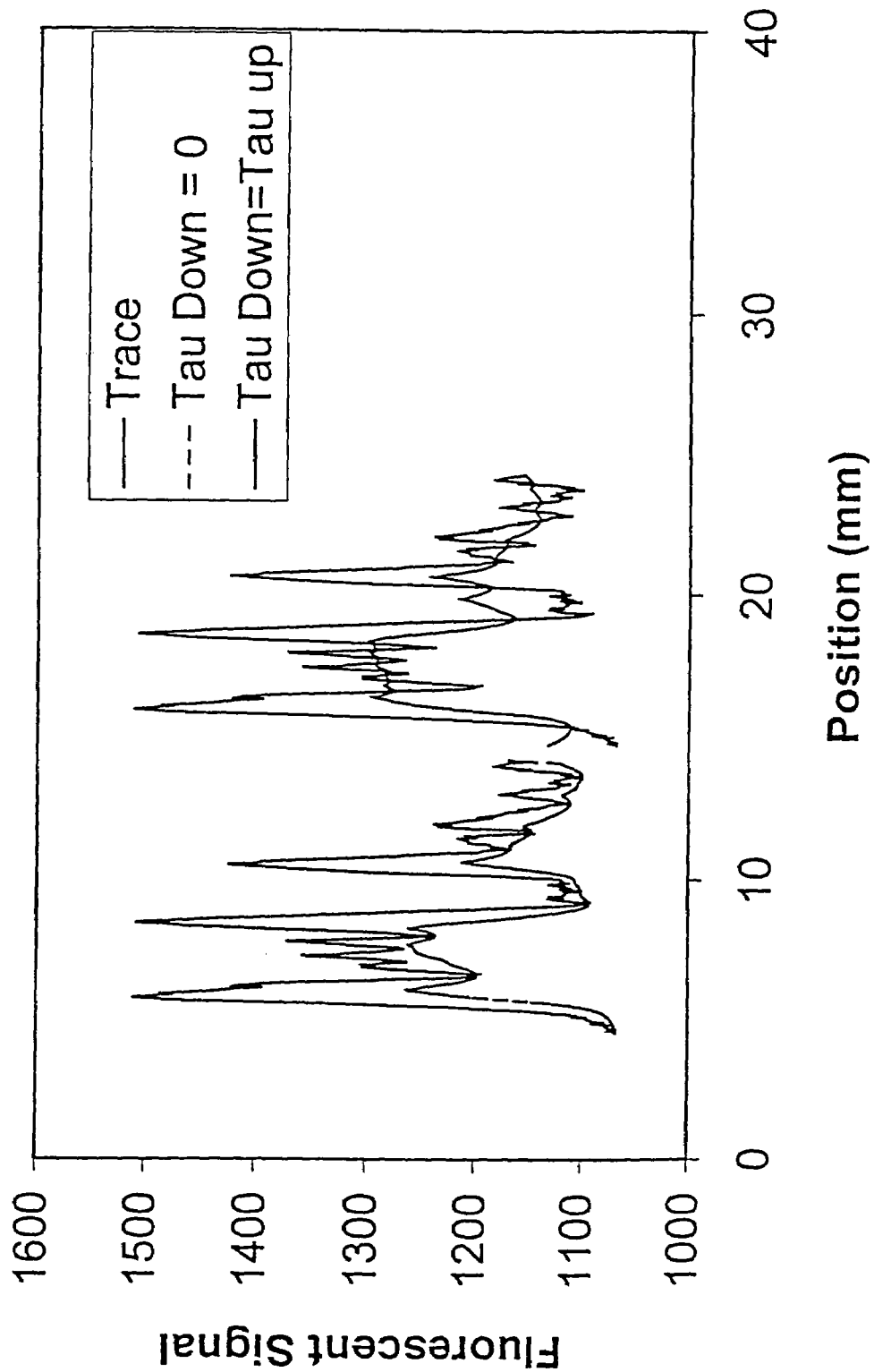

FIG. 13 illustrates filtering effects as a function of time constants.

Figure 14:
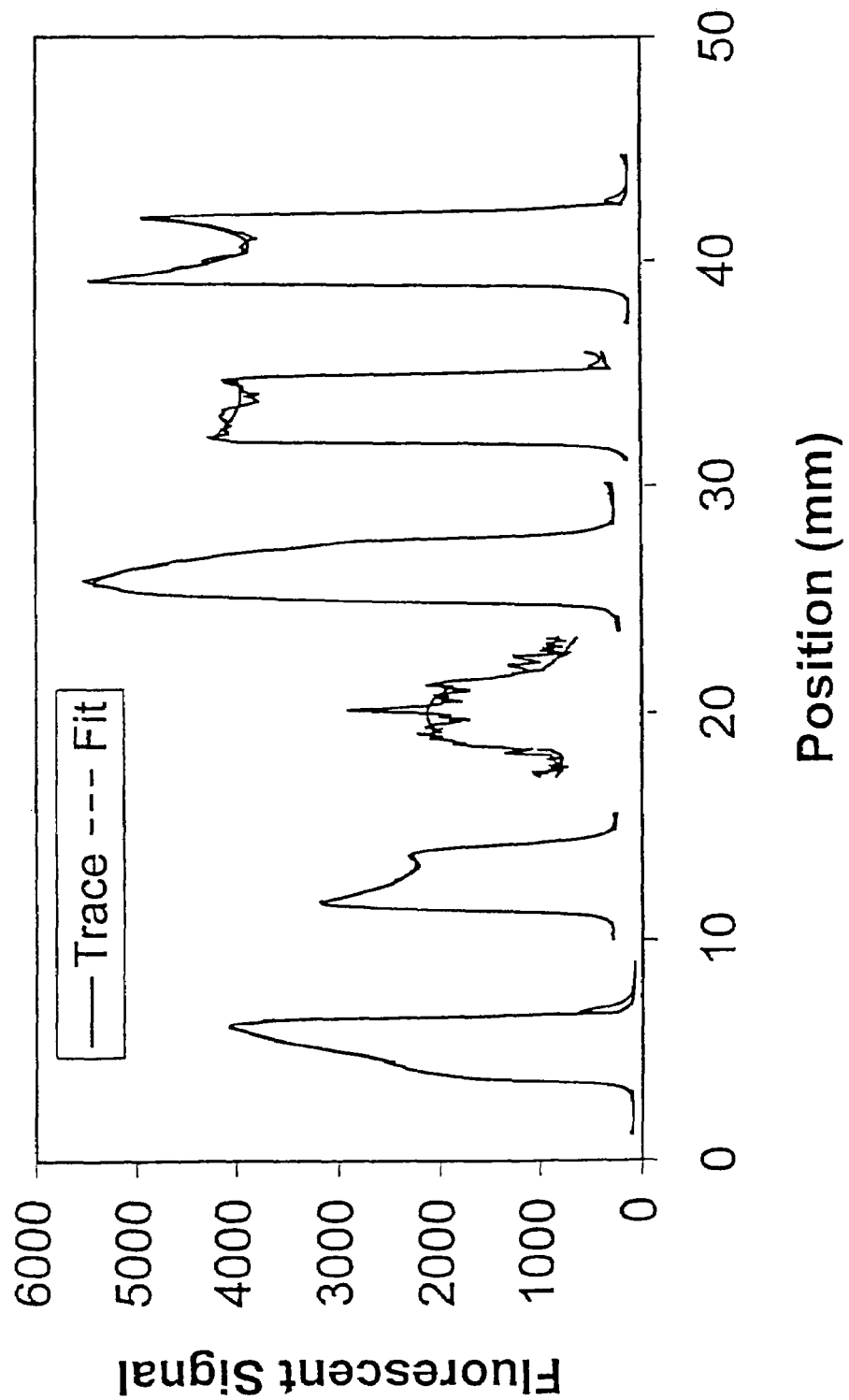

FIG. 14 depicts filtering effects as a function of parabolic fit functions.

Figure 15:
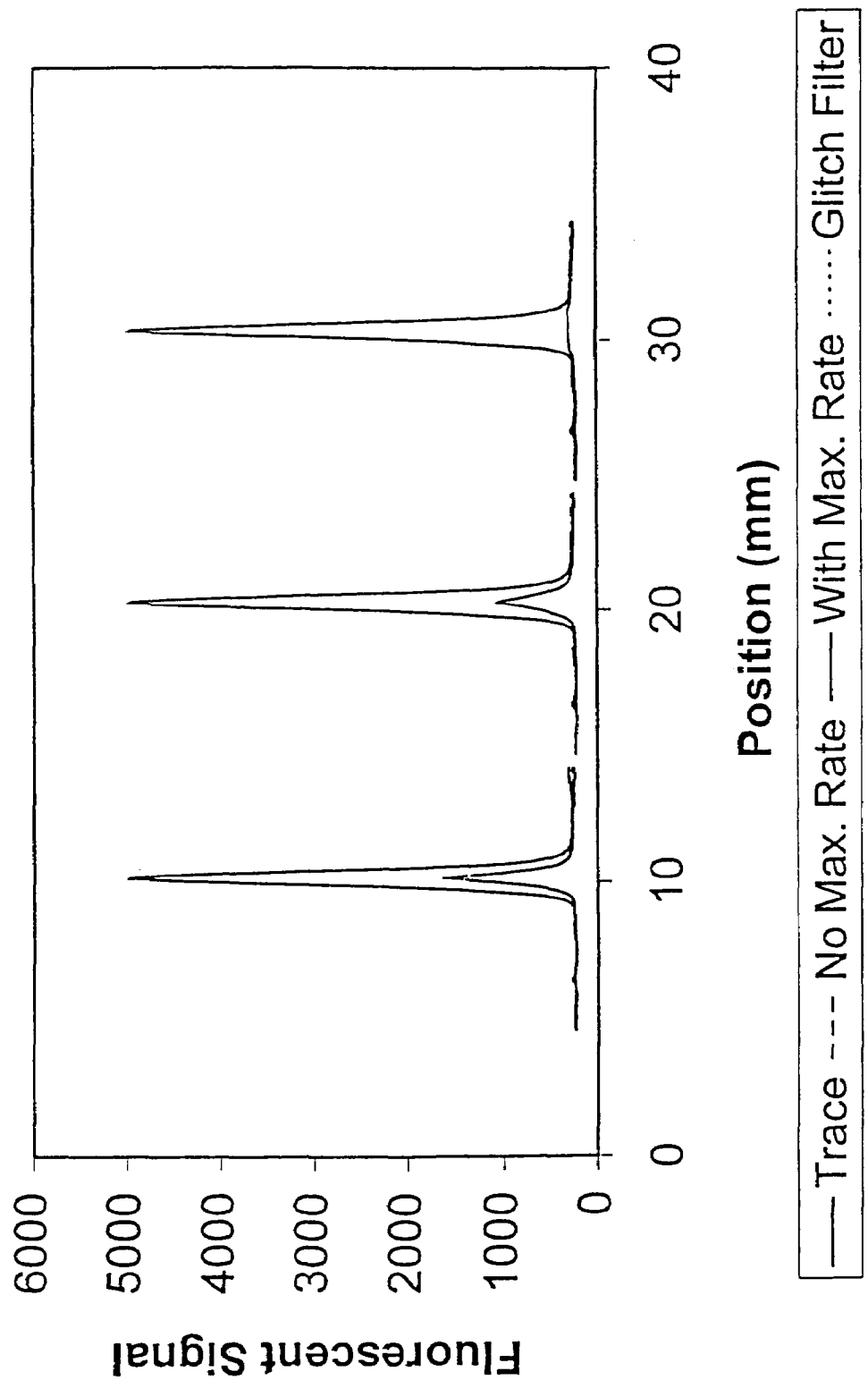

FIG. 15 illustrates filtering effects with respect to maximum allowed rate of change functions.

Figure 16:
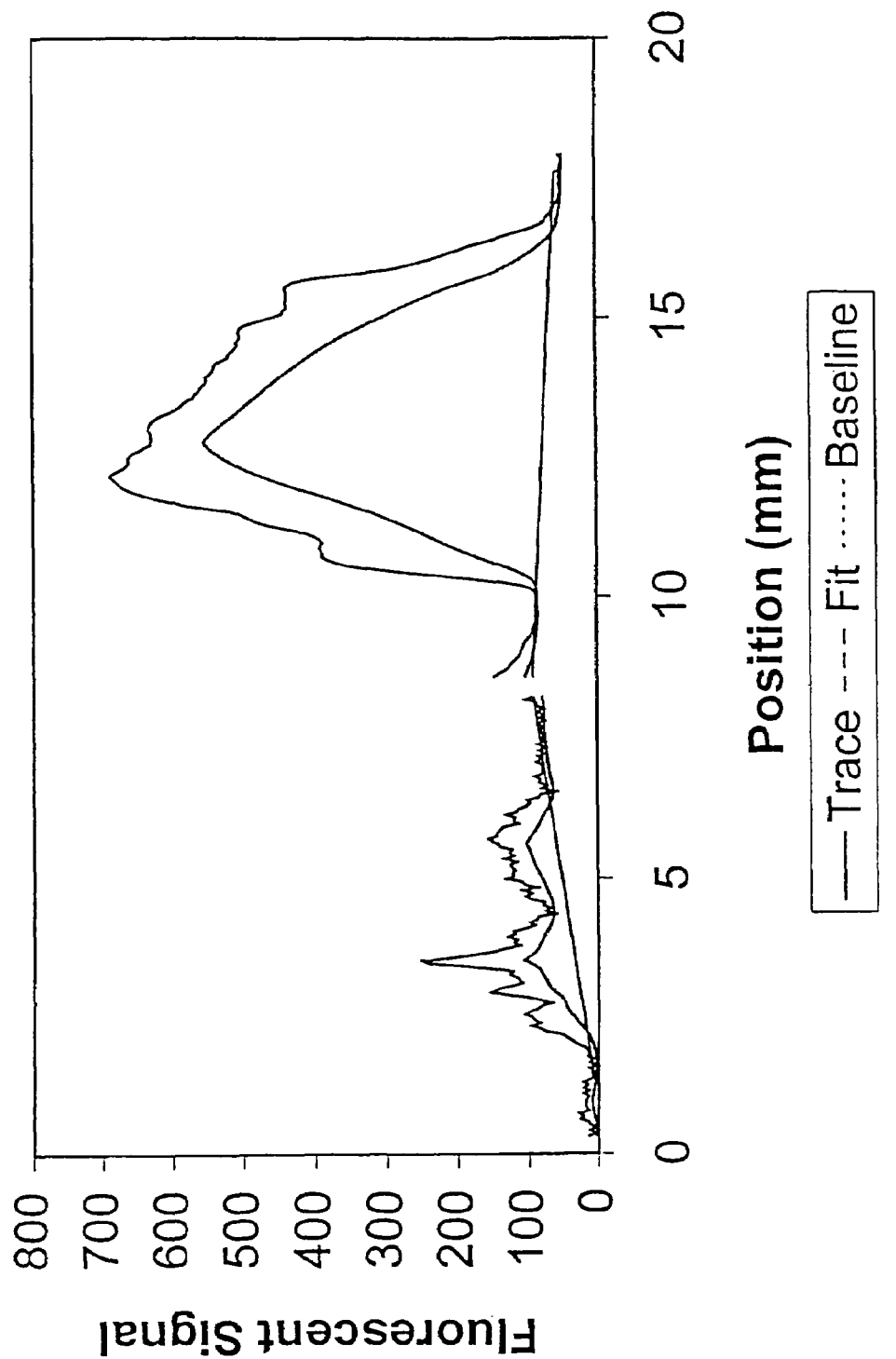

FIG. 16 depicts filtering effects with respect to rejection zones.

Figure 17:
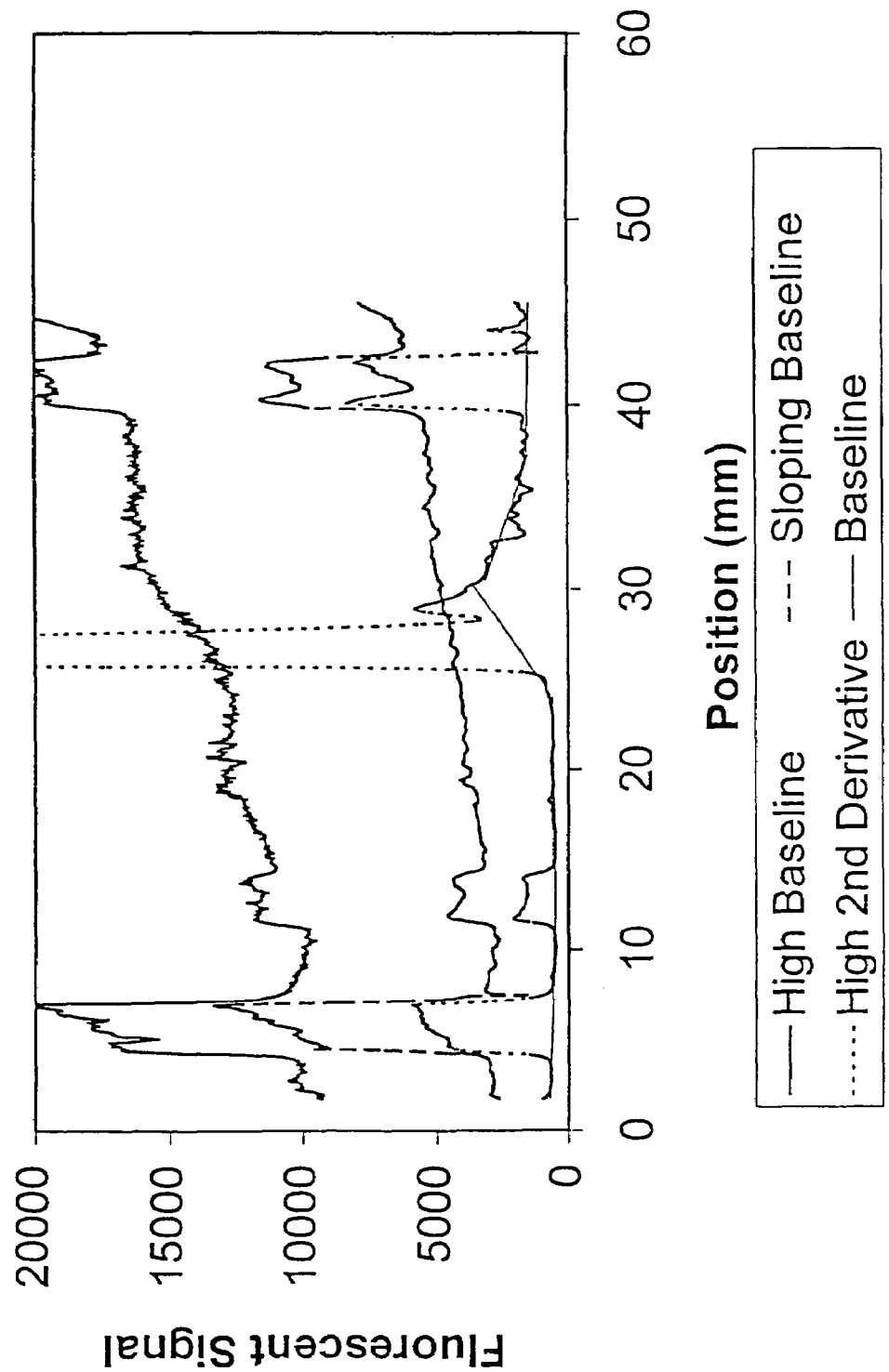

FIG. 17 illustrates filtering effects with respect to second derivative analysis.

All of these embodiments are discussed in detail hereafter.

Figure 18:
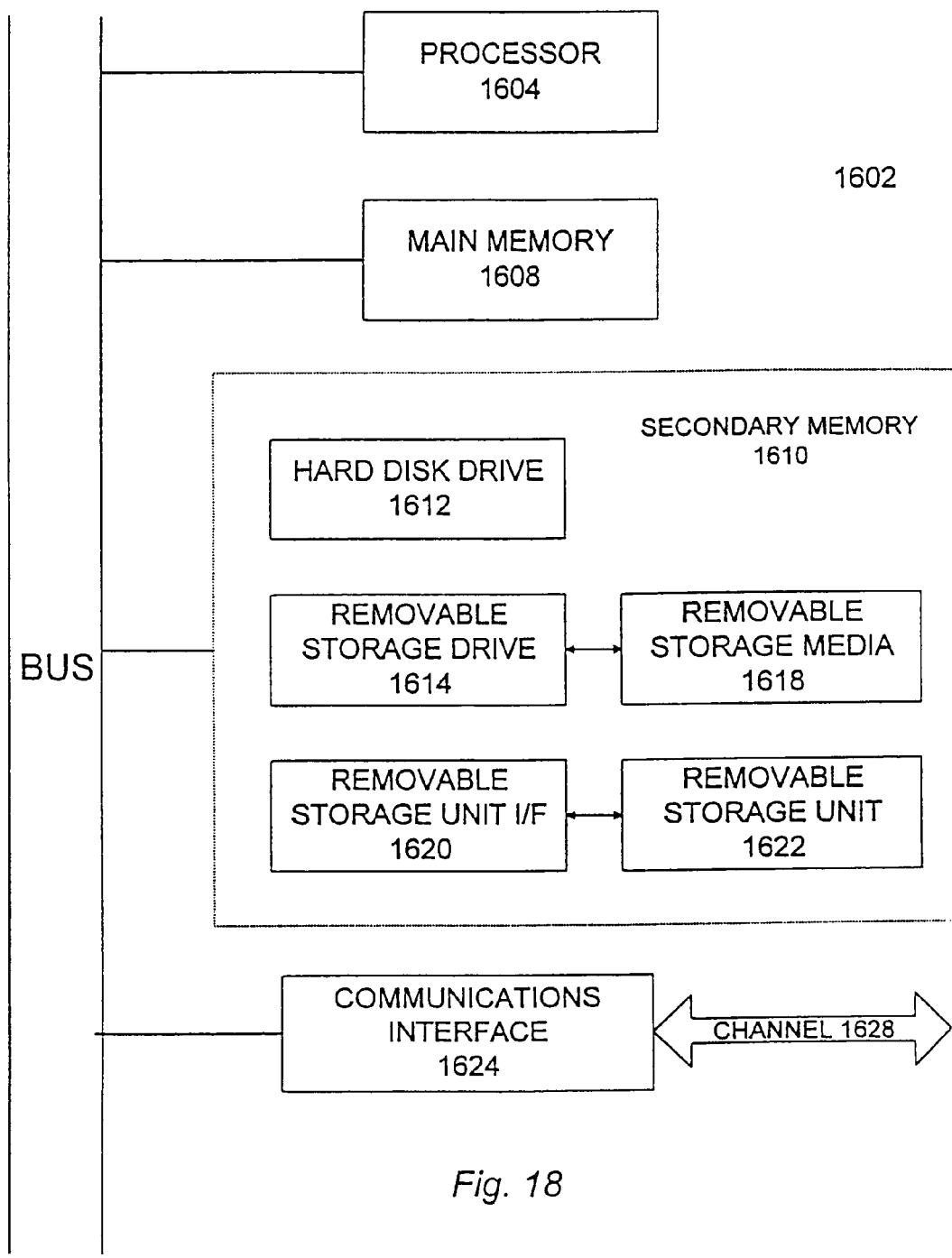
Figure 19:
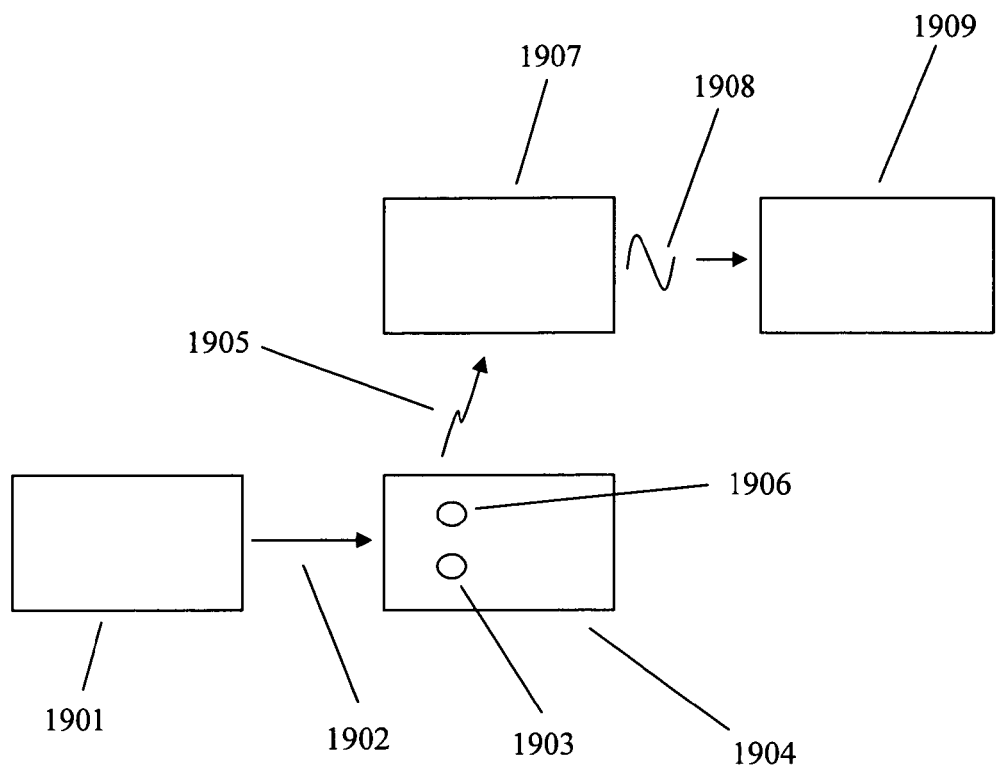

Various embodiments of the invention may be implemented using computer hardware, software or a combination thereof and may be implemented in a computer system or other processing system. An example computer system is illustrated in FIG. 18.

DETAILED DESCRIPTION OF THE INVENTION

This invention is related to novel methods that utilize independent assay controls (IAC). The IAC communicate optically with an instrument for the definition of the status of an immunoassay in an assay device. The IAC are related to the visualization and interpretation of immunoassays in an assay device that are specific, independent binding events and they can be related to the visualization and interpretation of total assay device fluorescence which can be related to non-specific binding events. In one embodiment, the IAC are used for defining the status and the time of completion of an immunoassay in an assay device. In another embodiment, the IAC define zones and profiles of assay signals. In yet another embodiment, the IAC redefine assay signals for purposes of correction of the assay signals as a function of sample matrix differences and sample flow rates in assay devices.

The IAC are immunoassays that are performed by the assay device. The magnitudes of the IAC signals are predictable within a range, set by the manufacturer, unlike the magnitudes of the analyte signals which are unpredictable. The novel features of the IAC are that they are independent of the presence or amount of analyte but dependent on the matrix of the sample and the progress of the immunoassay process in the assay device. The independent nature of the IAC from the analyte assays allows the design of their use to calibrate analyte assay signals that can be dependent on sample matrix and to define the shape and magnitude of the fluorescent signal to verify that the immunoassay process has taken place without error.

This invention relates to the use of IAC for an accurate and reliable measurement of analyte concentrations. In general, analytes are measured using methods related to immunoassays. One skilled in the art will recognize that immunoassays can be performed in non-competitive and competitive formats and the inventive teachings described herein are applicable to these formats but are not limited solely to these formats. For example, U.S. Pat. Nos. 5,028,535 and 5,089,391 teach a form of immunoassay that incorporates a threshold response with respect to the generation of signal as a function of analyte concentration and this methodology can be utilized with the IAC methodology. The methods utilize, for example, assay devices incorporating lateral flow of reagents and sequential binding of reagents to a solid surface, as well as instruments, which are described in U.S. Pat. No. 5,458,852 and co-pending U.S. patent application Ser. No. 08/458,276, Nowakowski et al., "Devices for Ligand Receptors Methods," filed Jan. 27, 1995; U.S. patent application Ser. No. 08/065,528, Buechler, "Diagnostic Devices and Apparatus for the Controlled Movement of Reagents Without Membranes," filed May 21, 1992; U.S. patent application Ser. No. 08/447,895, Buechler, "Diagnostic Devices and Apparatus for the Controlled Movement of Reagents Without Membranes," filed May 23, 1995; U.S. patent application Ser. No. 08/447,981, Buechler, "Diagnostic Devices and Apparatus for the Controlled Movement of Reagents Without Membranes," filed May 23, 1995; U.S. patent application Ser. No. 08/810,569, Buechler, "Diagnostic Devices and Apparatus for the Controlled Movement of Reagents Without Membranes," filed Feb. 28, 1997; U.S. patent application Ser. No. 08/828,041, Buechler, "Diagnostic Devices and Apparatus for the Controlled Movement of Reagents Without Membranes," filed Mar. 27, 1997; all of which are incorporated by reference in their entirety including all figures, tables, and drawings. One skilled in the art will recognize that with the inventive teachings described herein, other assay devices and instruments can also utilize these novel methods.

The reagents comprising the IAC are designed to provide information regarding the status of an immunoassay in an immunoassay device. The reagents are paired to result in a binding reaction as a result of the immunoassay, as one skilled in the art will recognize as an antibody/antigen binding reaction. The reagents comprising the IAC can be binding proteins, for example, antibodies and binding fragments that bind specifically to proteins, peptides, ligands and ligand analogues. The reagents can be in solution or attached to a solid phase. The reagents can be modified so that an antibody can bind to a ligand attached to another antibody or protein. As a result of the assay process, at least two reagents bind, either in solution or on a solid phase or both. At least one of the reagents of the IAC is attached to a label, directly or indirectly as a result of the assay process. Attachment can be made through the use of covalent bonds, electrostatic interactions, hydrophobic interactions and one skilled in the art is familiar with these techniques. A label can be dyes, fluorescent dyes, colloidal sols, molecule that generates an electrical and/or magnetic signal(s), and enzymes that convert molecules into dyes or reagents that become charged as a result of the assay process. In a preferred embodiment, the label is comprised of fluorescent dyes. In a particularly preferred embodiment, the fluorescent dyes are imbibed into or attached to particles, and they excite at about 670 nm and emit at about 760 nm. See, e.g., European Patent Application 94931287.0, Buechler et al., "Fluorescence Energy Transfer and Intramolecular energy transfer in particles using novel compounds," filed Sep. 23, 1994; U.S. patent application Ser. No. 08/601,492, Buechler, "Fluorescence Energy Transfer in Particles," filed Feb. 14, 1996; U.S. patent application Ser. No. 08/274,534, Buechler et al., "Fluorescence Energy Transfer in Particles," filed Jul. 12, 1994; and U.S. patent application Ser. No. 08/311,098, Buechler et al., "Fluorescence Energy Transfer and Intramolecular Energy Transfer in Particles Using Novel Compounds," filed Sep. 23, 1994; all of which are incorporated herein by reference in their entirety including all figures, tables, and drawings. The sizes of particles useful for this invention vary between about 2 nm to 4000 nm, and preferably between about 50 nm and 300 nm. In the case of utilizing enzymes to convert molecules into a label, one skilled in the art recognizes that conjugates of enzymes and, for example, antibodies, can be made using heterophilic cross linking reagents.

An important aspect of the invention is that the IAC reagents reside on separate or independent conjugates from each other and from the reagents used in performing the analyte assays. This critical function allows the IAC reagents to be independent of the analyte assay reagents so that the concentration of the analyte in the assay does not affect the perceived outcome of the assay as defined by the IAC. In addition, separating the IAC conjugates allows a novel approach to developing controls that have a variety of functions, each independent of each other, for defining the status of an immunoassay in a device, particularly in a device where the reagents move in a lateral fashion and the binding of the labeled conjugates to the solid phase occurs in a sequential manner. For example, the IAC conjugates and the assay conjugates are uncoupled because one may need different dynamic ranges for the analyte assays. For example, assay dynamic ranges in an assay device for myoglobin would be 0 to 1000 ng/ml, creatine kinase would be 0 to 150 ng/ml and troponin, which requires high sensitivity, would be 0 to 10 ng/ml. The substantially different dynamic ranges of each of these assays would require that, for example, different particle sizes of the label be used. Large dynamic range assays, such as myoglobin, would use small but many particles, whereas shorter dynamic range assays that require high sensitivity, such as troponin, would use larger and fewer particles. One skilled in the art recognizes this approach to design of immunoassays and furthermore, the use of enzyme conjugates with varying specific activities also creates assays with different dynamic ranges. Thus, due to the constraints of immunoassay design for the analytes, the IAC and assay conjugates must be uncoupled to prevent interferences. In another example of the versatility of the IAC and the necessity for uncoupling the binding events of the IAC and the assay reagents, analyte immunoassays and IAC that function in devices by the lateral movement of the assay reagents can potentially interfere with each other. For example, the binding of a label to a solid phase zone up stream from the binding of the same label to a down stream solid phase in a diagnostic lane can affect the signal of the down stream binding because the upstream binding event will remove all or a fraction of the reagent. Thus, the upstream binding event will affect the down stream binding event resulting in analyte assays or IAC results that cannot be predictable. The novel methods described herein provide that the IAC and analyte assay reagents be both separate and independent of the binding of each other and the assay reagents to solid phases, which in turn, allow reproducible and predictable signals to be generated for both the analyte assays and the IAC in lateral flow devices.

The IAC function in an assay device and communicate with an instrument. In a preferred embodiment, the instrument is a portable, battery powered fluorometer that incorporates a means for measuring an optical signal from an assay device and transforms the optical signal into an electrical signal. In a preferred embodiment, the instrument utilizes a laser diode emitting light at about 670 nm and a silicon photodiode as the excitation source and detector, respectively. The instrument also incorporates a means for storage of a variety of routines that allow it to measure and calculate the presence or concentration of one or more analytes, either utilizing information from the IAC or not, and to interface with outside data systems. A preferred instrument is described in U.S. patent application Ser. No. 09/003,090 entitled "Immunoassay Fluorometer," Buechler et al., filed Jan. 5, 1998, now U.S. Pat. No. 6,830,731, and U.S. patent application Ser. No. 09/003,066 entitled "Media Carrier for an Assay Device," Buechler et al., filed Jan. 5, 1998, now U.S. Pat. No. 6,074,616, both of which are incorporated by reference herein. One skilled in the art will recognize that instruments incorporating means for measuring the reflectance or absorbance of a light absorbing compound, that is, a label, can also be used in the practice of the inventive teachings described herein.

In a preferred embodiment, the assay device performs binding events, specific and non-specific for the IAC and one or more immunoassays for the measurement of the presence or concentration of one or more analytes. The immunoassay device comprises reagents for the IAC and for the measurement of analytes. The immunoassay device is generally a one-step device where a user applies one or more samples to one or a plurality of devices and the immunoassay process is performed within the device. The sample flows through the device in a lateral fashion without user interface utilizing capillarity as the driving force for fluid movement. In this preferred embodiment, the assay device generally binds a fluorescent label to a non-bibulous surface of the device as a result of the assay process. One skilled in the art will recognize that the binding of the variety of labels as a result of the assay process can also take place on bibulous supports, for example, in membranes and in paper. In a preferred embodiment, the binding of the label to a surface as a result of the immunoassay process can take place in one or a plurality of zones on the diagnostic lane of the assay device.

The immunoassay device generally has a compartment or chamber and a diagnostic lane in which and onto which reagents of the assay process are placed. In a preferred embodiment, a reaction chamber, which defines the volume of the reaction mixture, contains the reagents of the IAC and of the analyte specific assay, for example, fluorescent antibody conjugates. In assay devices that do not comprise bibulous supports, the capillary driving force is defined by the texture of the surfaces and the proximity of two surfaces, a base and a lid, that create a capillary space. A reaction chamber therefore has two surfaces onto which reagents of the IAC and analyte assays can be placed. In assay devices that comprise bibulous supports, such as membranes, the capillary driving force for fluid flow is generally defined by the pore size of the membrane. The diagnostic lane is the means in the assay device that binds the label in one or more discrete zones as a result of the assay process.

In a preferred embodiment the immunoassay process comprises adding a sample to an assay device, where the sample flows through a filter or a mesh for purposes of filtering cells from plasma or filtering out debris, or for lysing cells, respectively. A portion of the sample flows into a reaction chamber and combines with the assay reagents to form a reaction mixture. The reaction mixture is usually allowed to incubate for a period of time, generally about 30 seconds to about 5 min, to allow the reactions to reach substantial equilibrium binding. The reaction mixture then continues to flow in a lateral fashion, past one or more discrete zones on a solid phase of the diagnostic lane, whereby the label in the reaction mixture binds to one or more of the zones as a result of the assay process. Excess sample flowing behind the reaction mixture acts as a wash to remove label that has not bound to the solid phase. The extent and degree of label from the analyte conjugates and from the conjugates of the IAC binding to the solid phase in the zone or zones can be indicative of the concentration of analyte in the sample and the flow mechanics, incubation time, reaction mixture homogeneity and sample matrix, respectively. The concentrations of the analytes and the intensities of the IAC are quantified by the instrument by placing the assay device into the instrument and measuring the light energy resulting from the binding of the labels to the solid phase.

The proximity of the IAC reagents in the reaction chamber can define and monitor functions related to the non-specific binding of label, flow mechanics, incubation time, homogeneity of the reaction mixture and sample matrix of the assay.

In a preferred embodiment, a non-specific binding control IAC is incorporated in the device. This function is termed the non-specific binding control. The non-specific binding control is comprised of the entire repertoire of label in the device and a zone or zones on the diagnostic lane. The zone or zones of the diagnostic lane can comprise an antibody or the surface of the device or both that does not specifically bind the label but binds the label through non-specific binding events. One skilled in the art is familiar with non-specific binding events. Thus, the non-specific binding control IAC monitors the degree of non-specific binding of the label to the solid phase and identifies problems with sample matrices. For example, the presence of heterophilic antibodies in samples can crosslink label antibody conjugates to other antibodies and this non-specific binding event can result in an increase in label binding to the solid phase zones of the assay device.

In a preferred embodiment, a flow control IAC is incorporated in the device and this function is termed a flow control. The flow control IAC is comprised of a label onto which is attached proteins, antibodies, ligands, peptides, or ligand analogues and can be placed on the base or lid of the reaction chamber with the assay reagents. The flow control IAC reagents are reconstituted in the reaction chamber by the sample and ultimately bind to the solid phase of the diagnostic lane. The solid phase reagent is complementary with the reagent on the flow control label such that the binding can take place. For example, a ligand analogue is attached to the label and an antibody to the ligand analogue is attached to the solid phase. The flow control IAC ultimately documents the flow rate of the reaction mixture in the capillary of the diagnostic lane. Preferred reagents for the flow control are fluorescent particles about 50 nm to 300 nm in diameter and have attached an antibody, a ligand or a ligand analogue. The solid phase reagent is preferably a ligand, ligand analogue or an antibody, respectively. One skilled in the art will recognize that various combinations of binding events with reagents can result to define the flow control.

In another preferred embodiment, the incubation time of the reaction mixture in the reaction chamber is monitored by the IAC and is termed a time gate control. For example, in this embodiment, a label with a ligand or a ligand analogue covalently attached, is placed on the base of the reaction chamber and an antibody with a tag covalently attached that binds the ligand or ligand analogue of the label is placed on the lid of the reaction chamber. The labeled ligand conjugate is termed a time gate control label and the antibody tag conjugate is termed a time gate control antibody. When sample flows into the reaction chamber as a result of the assay, the lid and base reagents are reconstituted by the sample and the lid antibody and the label begin to bind to each other. The binding of these two reagents of the IAC is a function of time, their relative dissolution rates and their relative diffusion coefficients. The time element of the binding can therefore monitor the incubation time of the reaction mixture. Thus, what is formed in this reaction mixture is a label bound with an antibody tag. The tag of the antibody ultimately binds to an antibody on the solid phase of the diagnostic lane and the intensity of the signal from the label is related to the incubation conditions of the reagents in the reaction chamber. Preferred labels for the time gate control are fluorescent particles about 50 nm to 300 nm in diameter and have attached an antibody or a ligand or a ligand analogue. Preferred complementary reagents that bind to the label during the incubation are proteins, such as bovine serum albumin that have a ligand complementary to the antibody or an antibody complementary to the ligand or the ligand analogue, respectively. Preferred tags are ligands, ligand analogues, peptides and the like. One skilled in the art will recognize that various combinations of ligands, ligand analogues, antibodies and peptides, both in solution and on the solid phase, can be configured to provide a time gate control. One skilled in the art will also recognize that the time gate control label and time gate control antibody can be placed in a number of different locations in the device. For example, the time gate control antibody can be added to the sample or placed in the device prior to entering the reaction chamber, such as in the sample or in a filter, respectively, and the label can be placed on the base and/or the lid of the reaction chamber.

In another preferred embodiment, a label with a ligand analogue and an antibody1 with a tag1 are placed on the base of the reaction chamber and an antibody2 with a tag2 is placed on the lid. In this preferred embodiment, the congruency of the reaction mixture is defined with respect to the homogeneity of the reaction mixture as it relates to the relative dissolution of the reagents on the base and the lid. This control is termed the reaction chamber control. The reagents are reconstituted in the reaction chamber with sample, and the rate at which sample flows into the reaction chamber can affect the relative dissolution of the regents. For example, if the sample flows slowly into the reaction chamber, more of the reagents are dissolved by the advancing sample front than if flow into the chamber is rapid. The relative dissolution of the reagents on both lid and base should thus be optimized so that dissolution is independent of flow rate into the chamber. However, this ideal situation is not always possible to achieve in practice. Thus, the lid antibody2 tag2 binds to the ligand analogue of the label on the base and the base antibody1 tag1 binds to the tag2 of the lid antibody2 tag2. This binding sequence comes to equilibrium in the reaction mixture that is congruent with the dissolution of the lid and the base reagents. The tag1 of the base antibody1 ultimately binds to an antibody on the solid phase of the diagnostic lane resulting in the binding of the label to the solid phase. The relative signal of this IAC is thus dependent on the homogeneity of the reaction mixture in the reaction chamber. Preferred reagents for the reaction chamber control are fluorescent particles about 50 nm to 300 nm in diameter and have attached an antibody, a ligand or a ligand analogue. The complementary control reagent in solution with the label and on the lid are preferably a protein with a ligand or ligand analogue attached, or antibodies complementary to the ligand or ligand analogue. The solid phase reagent is preferably a ligand, ligand analogue or an antibody.

A preferred embodiment of the invention utilizes the IAC for defining the progress and the time of completion of the immunoassay in an assay device. The timing function has importance in that the user does not need to pay attention to the progress of the assay. In emergency rooms of hospitals, for example, a nurse can add a blood sample to a device and insert the device into the instrument, walk away to perform other duties and come back to the instrument, for example, when the instrument makes an audible sound, to get the assay results. Another example for the utility of the timing function is that an unskilled operator of the assay system may not be able to determine when the assay has been completed. In this case, the timing function provided by the IAC allows the instrument to judge when the assay process is complete.

A preferred configuration of the timing function is to use the signal intensity of one or more IAC, for example, the flow control and/or the time gate control, as a measure of assay completion. This embodiment functions when an immunoassay is started by the addition of sample to an assay device. As with all embodiments of the instant invention, the sample reconstitutes the reagents, for example, the assay reagents and the IAC reagents in the reaction chamber, they reach substantial equilibrium binding, and the reaction mixture flows through the diagnostic lane. As the IAC reagents flow in a lateral fashion through the diagnostic lane, the signal intensity on the discrete zones of the IAC increases. The IAC can also be designed to have a measurable signal prior to addition of the sample. This would be accomplished by addition of a soluble label to the IAC solutions prior to or at the time of application to the solid phase. When the reaction mixture flows through the diagnostic lane, the label in the IAC is washed out. The signal of the IAC would thus decrease as the label is removed by the reaction mixture occurs as a result of the assay process. Once all the reaction mixture has flowed through the diagnostic lane, the rate of increase of the signal of the IAC (and the analyte assays) decreases in a predictable manner.

In a particularly preferred embodiment of the timing function, the rate of change of the label bound at one or more discrete zones on the assay device, that is, the rate of change of the signal intensity, is a measure of the completion of the assay process. The absolute rate of change of the label binding to discrete zones in the diagnostic lane for defining the completion of the assay is arrived at empirically.

A particularly preferred location in the device for measuring the timing signal is at the end of the diagnostic lane. This location is particularly preferred because the end of the diagnostic lane is the last to be washed of unbound label. Therefore, when the end of the diagnostic lane is free of unbound label, the beginning of the diagnostic lane, that is, the closest to the reaction chamber, is also free of unbound label.

In yet another particularly preferred embodiment of the timing function, the negative rate of change of the total label in the diagnostic lane at one or more zones of the assay device is a measure of the completion of the assay process. The acceptance by the timing function of a negative rate of change of the label for assay completion is related to the sensitivity requirements of the assay. That is, a high rate of change of the signal implies that the assay process is still taking place, but depending on the application of the assay, the assay process may need to be only 75% complete for an acceptable answer. Conversely, a slow negative rate of change of the signal indicates that the assay process is complete or nearly complete and this condition may be desirable when very sensitive and accurate results are required. The negative rate of change of the signal approaches zero as the washout of the label approaches completion. In many applications of the invention and in practice, the negative rate of change can be a non zero number, where the non zero number relates to a condition whereby the majority of the label has been washed from the diagnostic lane. In the strictest sense, the negative rate of change becomes zero when the washout is complete.

A preferred embodiment of the timing function also measures one or more absolute signal intensities in one or more discrete zones as well as a negative rate of change of signal. This embodiment is important because the instrument must be programmed to distinguish assay devices that have had no sample added from those that have had sample added. In the case when sample is not added to the assay device, the rate of change of label, measured by the instrument during the timing function, would be zero, and the instrument could interpret this result to mean that the assay is complete although the assay was never begun. In addition, when sample has been added to the device and the signal has reached a maximum, that is, the device has not washed the label from the diagnostic lane and the immunoassay has not been completed, then the rate of change of the signal can also reach zero. Thus, the instrument should confirm that the sample has been added to the assay device, regardless of the specification of the rate of change of the label, by additionally specifying the achievement of a defined signal. The defined signal would be predictable within a range. The maximum signal in the range would be that obtained by measuring the total label and the minimum signal would be defined by the non-specific or specific binding of the label to the device. The signal utilized for defining assay completion is chosen to be greater than the signal obtained when no label has flowed in the diagnostic lane and greater than a predetermined value that would be derived from a typical non-specific binding signal when all the label has been washed from the diagnostic lane. Thus, the criteria for defining assay completion in an assay device are arrived at empirically.

A complication that has been observed in measuring the signals for triggering a measurement of the assay signals is the variation of the non-specific binding signal in a single device. The novel teachings described herein obviate this complication. The signal to background ratio can potentially be high or less defined than desired at certain zones in the diagnostic lane, for example due to sample matrix variability and imperfections in the surface of the diagnostic lane. Therefore, the analysis of an absolute signal by the timing function to trigger a measurement of the analyte assay zones should include some form of signal averaging. One skilled in the art will recognize that there are many methods for reducing noise in a slowly varying function. One of the simplest methods is to use an N point smoothing function, where each point is replaced with the average of N points surrounding it. Even with N point smoothing it may be likely that two consecutive points which meet the stability criterion is achieved before the desired rate of change has actually occurred. The probability of this potentially false trigger can be reduced to an acceptable level by requiring a certain number of smoothed points in a row to meet the stability criterion.

In a preferred embodiment stability criteria include the requirement of a negative first and positive second derivative. This will prevent a premature trigger when a local maximum is being measured rather than the minimum signal. These derivative criteria are problematic in that, if the device is measured by the instrument after all the signal has flow through the device, then both the first and second derivatives are zero, plus and minus instrument noise, so this condition become statistically improbable. This adds time to reach the stability criterion. One can recognize this condition since the signal level typically will be much less than the high threshold. In a preferred embodiment the slope criterion are bypassed when the signal is some fraction below the high threshold.

An important aspect of the IAC timing function is to recognize, and alert the user, that a device does not run properly. Timeouts are included that require sample to flow and stability to be reached within a certain times.

In a preferred embodiment a programmable duty cycle is incorporated. This reduces power requirements, prolonging battery life.

Preferred reagents for the timing control are fluorescent particles about 50 nm to 300 nm in diameter and have attached an antibody, a ligand or a ligand analogue. The solid phase reagent is preferably a ligand, ligand analogue or an antibody, respectively. A particularly preferred reagent for the timing control comprises the total fluorescent label in the assay device.

In another preferred embodiment of the invention, the IAC define the shape of an integrated signal. The definition of the shape of an integrated signal is important in that the slope of the rise and fall functions of the signal defines important parameters with which the instrument measures the analyte zones for determining the concentration of the analyte. The shape of the integrated signals is important and can define problems with the mechanism for measuring the signal, for example the optics or a means for moving an assay device by the optics, as well as problems associated with the assay device. For example, if the means for binding the label to the solid phase, for example, an antibody, is applied to the device surface in an area smaller or larger than desired, the integrated signal would have a smaller or larger value, respectively, resulting in erroneous results. The IAC would define the incorrect shape of the integrated signal of the zone and give the user an error message, defining that the assay results may not be reliable. In a system where the measurement is made over time or space one can utilize the expected behavior of the assay with the measured behavior as a method of Quality Control (QC) for the assay. Any assay that deviates substantially from the expected behavior, as defined by the profile of the signal is rejected, while an assay that matches the expected behavior is accepted. This novel QC step raises the reliability of the assay. In practice the behaviors which most critically depend on a properly functioning assay must be identified. If an assay is monitored over time, the signal response as a function of time could be measured. If the assay is measured over 1 or more dimensions, then one should look for characteristic shapes in area of interest. This type of analysis is similar to a matched filter analysis.

In a preferred embodiment, the response as a function of the position along the diagnostic lane is measured. The characteristic shape and location of each zone of interest, as well as any relationships between zones is defined by the manufacturing process of the assay device. The maximum rate of change expected at any given assay or IAC zone as the assay progresses in the device is also defined by the manufacturing process, the design of the device and the assay, so any deviation in the measured results from the expected results is interpreted by the instrument to be a glitch. One can filter the data with the usual assortment of high pass, low pass, and notch filters, as well as fit sections of the curve to specific functions, or use any type of exotic digital algorithm. These types of filters remove unwanted features such as glitches. This type of filtering is most beneficial in that it performs a local quality control check, and helps improve the precision of the result. One can verify that the filtering is applied only to signals within the maximum allowable signal to background of the assay and utilize the signal to background as an internal quality control check. Preferred compositions that define the shape of the fluorescent signal are the flow control reagents, the time gate control reagents, the reaction chamber control reagents, the assay reagents or combinations of these reagents.

In another preferred embodiment of the invention, the IAC define and verify the location of the zones of integrated fluorescence in the assay device. The location of the assay zones is critical for accurate measurement of the assay signals. For example, in the manufacture of the assay device, when the solid phase reagents for binding the label are applied to the device in discrete zones, misplacement of the reagents on the device could result in erroneous results. In another example, the gears on a motor that drives the assay device under an optical block for measurement of the assay signals could slip such that the absolute position that the instrument reads would not be coincident with the label bound to the discrete zones. This scenario would also result in erroneous results. The IAC would define these potential problems and the instrument would give an error message in response to an unexpected location of an integrated signal. The error signal would notify the user that the results should not be trusted. Preferred compositions that define and verify the location of the zones of the integrated fluorescent signal are the flow control reagents, the time gate control reagents, the reaction chamber control reagents or combinations of these reagents.

In another preferred embodiment, the IAC redefine assay signals (of the analytes) for purposes of correction of the assay signals as a function of sample matrix differences, external and internal perturbations, variation in incubation times and sample flow rates in assay devices. In the development of immunoassays that are performed directly in viscous or heterogeneous samples, for example, as found with biological samples like blood, lysed blood, plasma, serum and urine, flow rates, binding efficiencies, binding interferences and the like are encountered. The result of these encounters is that virtually each sample can be different and the differences can result in abnormalities in the assay results. For example, in performing an immunoassay in a lysed whole blood sample, the viscosity of the sample can vary depending on the hematocrit of the blood sample. An increase in the viscosity of the sample causes the sample fluid to flow more slowly in a capillary of the assay device. As the flow rate decreases in the capillary and the binding reaction occurs as the fluid flows past the binding zones, the rate of binding to a solid phase can be increased because the sample resides near the binding site for a longer period of time. This scenario yields an assay signal that is greater than would be expected and as a result, the calculation of the analyte concentration would be in error. In addition, as the viscosity of a sample increases, the rate of diffusion decreases. The decrease in the rate of diffusion increases the time needed to approach equilibrium binding. If the immunoassay is designed to be at equilibrium when the instrument measures the assay, and the assay has not come to equilibrium, then the results of the assay may be erroneous. In yet another example, if a sample contains a component that binds to or in some way affects the binding reactions of the immunoassay, such as, for example as is observed when heterophilic antibodies are present in a patient's blood, then the immunoassay process can be jeopardized and the assay results can be erroneous. The role of the IAC in this embodiment would be to correct the assay signal based on a change of the IAC. In addition, the IAC could result in reporting an error message to the user, particularly if the non-specific binding component to the solid phase is abnormal. Preferred compositions of reagents that redefine the assay signals for purposes of correction of the assay signals are the non-specific binding control reagents, the flow control reagents, the time gate control reagents, the reaction chamber control reagents or combinations of these reagents.

In yet another preferred embodiment of the invention, the deviation from a mean value of the IAC is used to correct the assay in order to improve the imprecision of assay results in different assay devices using the same or different samples. For example, variations in hematocrit of blood samples will affect the viscosity of the sample and therefore the flow characteristics in a lateral flow device. This embodiment relates to the estimation of a mean signal intensity of the IAC and the extent of deviation from that mean. It is a feature of this invention to teach how to utilize deviations from a predicted value of the IAC to reassign values to assay results.

In yet another preferred embodiment of the invention, the deviation from a mean value of the ratio of at least two identical IAC signals is used to verify that a predictable immunoassay has been performed, and that within a scope of high probably, the immunoassay results should be reliable.

In yet another preferred embodiment of the invention, the deviation from the mean value for multiple IAC are used to correct the assay in order to improve the imprecision of assay results in different assay devices using the same or different samples. In a preferred embodiment the deviation of an IAC can be influenced by the deviation of other IAC. For example, two IAC may be present on the device, one that is primarily sensitive to the flow rate of the device, and one that is primarily sensitive to the incubation time of the device. This embodiment teaches how to utilize both controls simultaneously even when the results of each IAC is influenced by the result of the other. This teaching will rely on the principles of linear algebra.

In principle, the assay system can be perturbed by many factors, such as sample heterogeneities, interfering substances and the like and it would be desirable to develop an IAC for each variable that affects the assay. In this ideal case the IAC are said to be independent or orthogonal. More generally the IAC may be dependent on one another, but since they are different it is assumed that they respond differently to variations in different parameters, and they are therefore said to be linearly independent. If this assumption is not correct the controls provide identical information. In the context of linear algebra this means that the controls form a basis for the parameters which influence the assay. For example, a change in flow rate in the diagnostic lane may affect the value of the time gate control as well as the flow control. Although the controls are dependent, the two in conjunction provide a unique description of the flow rate and time gate time, so both controls are used to normalize the result.

A particularly preferred embodiment of normalizing the assay signals by the IAC teaches that the source of the variability in the assay does not need to be identified or that an IAC exist for each variable that may arise. For example, in the description above, it was assumed that flow and time gate time are the two important variables. However, these are only labels given to controls that may in fact be sensitive to other parameters. To utilize the IAC in this preferred embodiment, it is assumed that there are n parameters that affect the assay results and n linearly independent controls for these parameters. For a given sample, the mean of many assays defines the average or expected result for the controls ($C_{ave}$) and the assay ($T_{ave}$). In the embodiment of one parameter, P, that affects the assay result, the measured control value ($C_m$) is equal to the expected control value plus a term proportional to the variation of the parameter and is described as:

$$C_m = C_{ave} + \alpha \, \delta P \qquad \text{eqn. j1}$$

It follows that the measured value of the test can be described as:

$$T_m = T_{ave} + \beta' \, \delta P \qquad \text{eqn. j2}$$

In the analysis that follows it is assumed that $\alpha$ and $\beta'$ are not functions of $\delta P$. This is a good assumption when $\delta P$ is small. $\alpha$ and $\beta'$ can have functional dependence on the value of P. The following can be applied for small variations around multiple values of P yielding the functional form with respect to P. When the variations of the parameter are small, $\alpha$ and $\beta'$ are constants that represent the derivatives of the control and test with respect to the parameter (dC/dP and dT/dP). These equations can be more simply written:

$$\delta C = \alpha \, \delta P \qquad \text{eqn. j3}$$

$$\delta T = \beta' \, \delta P \qquad \text{eqn. j4}$$

and combined to form:

$$\delta T = (\beta'/\alpha) \delta C = \beta \, \delta C \qquad \text{eqn. j5}$$

From this, $\beta$ is found, which is easily accomplished experimentally. There is no need to ever identify or solve for the parameter.

In a preferred embodiment where there are n parameters, P, and no controls, C, the following similar equation is written:

$$\delta C = \alpha \, \delta P \qquad \text{eqn. j6}$$

Note that now the variation in the controls ($\delta C$) and the variation in the parameters ($\delta P$) are both vectors while the partial derivatives ($\partial C_k / \partial P_j$) form an n by n matrix ($\alpha$). If each control is purely a function of one parameter then the $\alpha$ matrix is diagonal. If the controls are linearly independent than an inverse for $\alpha$ will exist.

In an analogous way it can be written:

$$\delta T = \beta' \, \delta P \qquad \text{eqn. j7}$$

Again the partial derivatives ($\partial T / \partial P_j$) form an n dimensional vector ($\beta'$). From linear algebra it can be written that:

$$\delta P = \alpha^{-1} \delta C \qquad \text{eqn. j8}$$

Using this it can also be written:

$$\delta T = \beta' \alpha^{-1} \delta C = \beta \, \delta C \qquad \text{eqn. j9}$$

Note the similarity to equation j5. Again it is not necessary to ever solve for $\alpha$, instead it is possible to determine $\beta$ experimentally. The inventive teachings described herein show that there is no need to identify or solve for the parameters that are varying. Equations j5 and j9 can be used for correcting assay results as well as for determining $\beta$. When used to correct an assay result ($T_m$), the variation of assay results ($\delta T$) can be expressed as the difference between the measured assay result ($T_m$) and the corrected assay result ($T_c$). For determining corrected assay results, equation j9 can be expressed as:

$$T_c = T_m - \beta \, \delta C \qquad \text{eqn. j9a}$$

While there exists many ways for determining $\beta_j$ the above method does not influence the teachings presented above. For example, one method is to guess. While this can be time consuming, one skilled in the art will recognize that many computer algorithms will efficiently search an n parameter space and find the best value for $\beta_j$. When controls are independent of each other, each $\beta_j$ can be found from the slope of $\delta T$ versus $\delta C_j$. In a complex but more general approach, each $\beta_j$ can be found by maximizing the correlation between control variation and assay variation, and minimizing the standard deviation of the percent assay variation. A straightforward and very general method is described below. Included are some important special case results that are derived from this approach.

The n elements of $\beta$ ($\beta_k$) can be determined experimentally by performing a statistically significant number of assays, which contain random fluctuations in the IACs. The results are averaged to define the expected test value ($T_{ave}$) and the expected value for each IAC ($C_{kave}$). For each assay the variation in the test ($\delta T_j$) and IACs ($\delta C_{ki}$) can readily be determined. Using equation j9 and summing over all devices, represented by i, we can write for each of the n IAC:

$$\Sigma_i (\delta T_i \delta C_{ki}) = \Sigma_i \{ \Sigma_j (\beta_j \, \delta C_{ij}) \, \delta C_{ki} \} = \Sigma_j (\beta_j \Sigma_i \{ \delta C_{ij} \, \delta C_{ki} \}) \qquad \text{eqn. j10}$$

Equation 10 defines a system of n equations (for the n IACs) with n unknowns (the elements of $\beta$). To simplify the form of equation 10, we define a symmetric matrix, K, as follows:

$$K_{jk} = \Sigma_i \{\delta C_{ij} \delta C_{ki}\} = K_{kj} \quad \text{eqn. j11}$$

Using equation j11, equation j10 can be simply expressed in the following two forms:

$$\Sigma_i (\delta T_i \delta C_i) = K \beta \quad \text{eqn. j12}$$

$$\beta = K^{-1} \Sigma_i (T_i \delta C_i) \quad \text{eqn. j13}$$

Equation j13 defines the solution to the system of equations represented by equation j12. The method for finding the inverse of a n×n matrix can be found in any text on linear algebra. See, e.g., *Matrixes and Tensors in Physics* (2$^{nd}$ edition), A. W. Joshi, page 47).

One skilled in the art will recognize that $K_{jk}$ is the covariance of the random distributions represented by the variations in the IAC. See, e.g., *Probability Distributions: An Introduction to Probability Theory with Applications*, 1972, C. P. Tsokos, page 367 for a discussion of the covariance of two random variables. If two random variables are independent then the covariance is zero. Therefore, for independent controls, $K_{jk} = k_j \delta_{jk}$ i.e. K is a diagonal matrix. For this special case, the inversion of K is trivial and equation j13 can be written as follows:

$$\beta_j = \Sigma_i (\delta C_{ij} \delta T_i) / \Sigma_i (\delta C_{ij})^2 \quad \text{eqn. j14}$$

One skilled in the art will recognize this as the equation from the least squares fit of a line with 0 intercept. In other words, when the controls are independent, the slope of $\delta T$ versus $\delta C_j$ (i.e. $\partial T / \partial C_j$) is $\beta_j$.

In the teaching above, the matrix ($\beta$) relating the variations in the controls to variations in the test (analyte assay) is found for a specific test value, but it was not assumed that $\beta$ was not a function of the test value. The functional dependence of $\beta$ on the test value (T) can be determined experimentally by finding $\beta$ as described above at different test values.

In a preferred embodiment $\beta$ is found to be proportional to the magnitude of the analyte assay, that is:

$$\beta_j = \Gamma_j T_{ave} \quad \text{eqn. j15}$$

By using equation j15, equation j9 can be rewritten as:

$$T_m = T_{ave} + \Sigma_j \beta_j \delta C_j = T_{ave}(1 + \Sigma_j \Gamma_j \delta C_j), \text{ or} \quad \text{eqn. j16}$$

$$T_{ave} = T_m / (1 + \Sigma_j \Gamma_j \delta C_j) \quad \text{eqn. j17}$$

Note that equations j17 and 17.5 (see example 17) are the same equations. Equation j17 may be used to normalize assay results when one or more IACs present (either dependent or independent) and where the relation to the control variation is proportional to the magnitude of the test or assay results.

In a preferred embodiment where there is only one control, equation j15 holds, and $\Gamma$ is equal to $1/C_{ave}$, equation j17 reduces to:

$$T_{ave} = T_m / (1 + (C_m - C_{ave})/C_{ave}) = T_m C_{ave}/C_m \quad \text{eqn. j18}$$

This is the simple case where the test (assay) value scales proportionally with the control (IAC) value. That is, a factor of two change in the control value will result in a factor of two change in the test value. This is an IAC that responds identically to variations that also affect the assays of the analytes. One skilled in the art will now recognize that when an assay and an IAC change proportionately, this type of normalization is utilized.

In the equations above, we presented an idealized case of a system with no noise. One skilled in the art will recognize that the addition of a random noise term does not influence the methods presented above. This arises from the fact that random noise ($\delta N$) is by definition an independent variable with a mean of zero. As noted above the covariance of independent variables is also zero, so all terms involving random noise and other variables are zero. The only surviving term is $\delta N^2$. Because the random noise must be the small compared to other variations, (otherwise there is no reason to apply control correction) $\delta N^2$ is negligible. In other words the techniques described above require that variations in the parameters which are the dominate variations in the test be the predominate variation in the controls. Calculating the correlation between control variation and test variation can test for this condition.

EXAMPLES

The following examples are embodiments of IACs of the invention. These examples are for illustrative purposes only and do not limit the invention in any manner.

Example 1

Preparation of Fluorescent Energy Transfer Latex With Bovine Serum Albumin (FETL-BSA) and Antibody (FETL-AB) Conjugates Fluorescent energy transfer latex was prepared as described in U.S. patent application Ser. No. 08/409,298, filed 23 Mar. 1995 using silicon phthalocyanine bis (di-methylhexylvinylsilyloxide) and silicon [di(1,6-diphenylnaphthalocyanine)]diphthalocyanine bis (di-methylhexylvinylsilyloxide) as donor and acceptor dyes, respectively, at a ratio of 4 moles of donor to 1 mole of acceptor. The latex particles are about 230 nm in diameter and were purchased from Interfacial Dynamics Corporation. The FETL particles were adsorbed with bovine serum albumin (BSA) or various antibodies using techniques that are standard to one skilled in the art. Alternatively, the BSA or the antibodies were attached covalently to the particles using heterobifunctional crosslinking reagents (SMCC and SPDP, from Pierce Chemical Co.) also using techniques that are standard to one skilled in the art. These methods are outlined in the Pierce Chemical Co. catalogue, 1994, p. T166 and T192, in Uniform Latex Particles, Seradyn Inc., p 31-40 and in Microparticle Reagent Optimization, Seradyn Inc., p. 91-97. The unbound BSA was purified from the FETL-BSA by centrifugation at top speed in an Eppendorf centrifuge, model 5415C. The resulting particle was reconstituted in a buffer solution consisting of 10 mM potassium phosphate, 2 mM potassium borate, 150 mM sodium chloride, pH 7.0 at a solids concentration of about 2% (w/v).

Antibody FETL conjugates prepared in this fashion include anti-dansyl-FETL used for the flow control IAC, the anti-troponin I, anti-CKMB, anti-myoglobin FETL, anti-human chorionic gonadotropin (HCG) FETL conjugates used in immunoassays for measuring the concentrations of troponin I, CKMB, and myoglobin, respectively. One skilled in the art recognizes that the specific analyte antibody pairs listed here do not restrict the scope of this invention and that these antibody antigen pairs are used as examples of the invention. The monoclonal and polyclonal antibodies were prepared by standard techniques, for example, as described in *Antibodies, A Laboratory Manual*, Ed Harlow and David Lane, Cold Spring Harbor Laboratory (1988), Cold Spring Harbor, N.Y.

The recombinant antibodies prepared and screened for the cardiac marker assays were prepared from genetic information derived from mice by various procedures as described in *Antibody Engineering: A Practical Approach* (Borrebaeck, C., ed), 1995, Oxford University Press, Oxford; J. Immunol. 149, 3914-3920 (1992) and as described in U.S. patent application Ser. No. 96/05476, incorporated by reference.

Example 2

Preparation of Flow Control FETL Conjugate for the Cardiac Marker Assay

To a solution of FETL-BSA, (11 ml at 1% solids, w/v, 220 nm particles), prepared according to example 1, was added with stirring, ascorbic acid and ethylenediamine tetraacetic acid to final concentrations of 20 mM and 0.1 mM, respectively. SMCC (3.8 µl of a 60 mM solution in acetonitrile) was added with stirring and the solution was incubated at room temperature for 2 h. The reaction was quenched by addition of 0.45 ml of 0.5 M solution of taurine. The solution was applied to a gel filtration column and 23.1 ml FETL-BSA-maleimide was eluted. A solution of decapeptide thiol (19 µl of 4.7 mM solution) was added and the solution was incubated at room temperature for 50 min. Decapeptide thiol was prepared by hydrolysis in as described in Example 4. The solution was applied to a gel filtration column and the eluted FETL-BSA-decapeptide was centrifuged at top speed in an Eppendorf centrifuge for 20 min. The pelleted FETL conjugate was resuspended to a final solids concentration of 2%, w/v in a phosphate buffered solution, pH 7.0.

Example 3

Preparation of Time Gate Control FETL Conjugate for the Cardiac Marker Assay

To a solution of FETL-BSA, (20 ml at 1% solids, w/v, 220 nm particles), prepared according to example 1, was added with stirring, ascorbic acid and ethylenediamine tetraacetic acid to final concentrations of 20 mM and 0.1 mM, respectively. SMCC (17 µl of a 60 mM solution in acetonitrile) was added to the solution, with stirring, and incubated at room temperature for 2 h. The reaction was quenched by addition of 0.82 ml of 0.5 M solution of taurine. The solution was applied to a gel filtration column and 16.9 ml of FETL-BSA-maleimide was eluted. Morphine-HCTL was synthesized and hydrolyzed to the corresponding thiol derivative as described in U.S. Pat. No. 5,089,391, Example 4, incorporated by reference. Morphine thiol (0.52 ml of a 16.3 mM solution) was added and the solution was incubated at room temperature for 3 h. The reaction was quenched by addition of N-ethyl maleimide to a final concentration of 2 mM. The solution was applied to a gel filtration column and the eluted FETL-BSA-morphine was centrifuged at top speed in an Eppendorf centrifuge for 20 min. The pelleted FETL conjugate was resuspended to a final solids concentration of 4%, w/v.

Example 4

Preparation of Time Gate Control Antibody Conjugate for the Cardiac Marker Assay To 1.0 ml of anti-morphine antibody, 36E10, at 10 mg/ml in 50 mM potassium phosphate, 10 mM potassium borate, 150 mM sodium chloride was added 0.022 ml of a 2 mg/ml solution of SMCC (Pierce Chemical Co.) in acetonitrile. The solution was stirred at room temperature for 3 h. The solution was then purified on a gel filtration column and the eluted protein collected was 2.4 mg/ml in 3.4 ml. To this protein fraction which consisted of antibody-maleimide was added 0.12 ml of a decapeptide thiol (see this example for the synthesis of decapeptide thiol). The solution was stirred at room temperature for 3 h and was subsequently dialyzed overnight against 50 mM potassium phosphate, 10 mM potassium borate, 150 mM sodium chloride, 0.02% sodium azide, pH 7.0. The recovered protein, which consisted of anti-morphine antibody decapeptide conjugate, was at 2.8 mg/ml in 3.2 ml.

Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetylimidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5-2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44-45° C.

Decapeptide Thiol Synthesis

The decapeptide thiolpropionamide (decapeptide thiol) was synthesized by hydrolysis of the decapeptide acetylthiopropionamide (decapeptide ATP). Decapeptide ATP was synthesized from the decapeptide, YPYDVPDYAS, (Chiron Mimotopes Peptide Systems, San Diego, Calif.) and acetylthiopropionic acid. Thus, the decapeptide was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 minutes at room temperature. This solution was added to the decapeptide solution and the reaction mixture was stirred for at least six hours at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and filtered using a fine fritted Buchner funnel. The solid was washed with an additional 20 mL of methylene chloride and the Buchner funnel was dried under vacuum.

The thioacetyl moiety of the decapeptide ATP was hydrolyzed by dissolution in 70% DMF to make a 20 mM solution. A solution of 1 N potassium hydroxide was added to a final concentration of 0.2 N while mixing vigorously. The solution was incubated at room temperature for 5 minutes prior to neutralization to pH 7 of the solution by the addition of a solution containing 0.5 M potassium phosphate, 0.1 M borate, 1 M hydrochloric acid. The thiol concentration of the decapeptide thiol derivative was determined by diluting 10 µL of the solution into 990 µL of a solution containing 0.25 mM 5,5'-dithiobis(2-nitrobenzoic acid) (DTNB, Aldrich Chemical Co., Milwaukee Wis.) and 0.2 M potassium borate, pH 8.0. The thiol concentration in mM units was equal to the $A_{412}(100/13.76)$.

Example 5

Preparation of Solid Phase Antibody, Avidin and Dansyl Latex Conjugates

The solid phase antibody latexes were prepared by adsorbing antibodies or bovine serum albumin to particles of about 130 nm in diameter. Procedures for adsorption of these proteins to latex particles are familiar to one skilled in the art and can be found in Uniform Latex Particles, Seradyn Inc., p 31-32 and in Microparticle Reagent Optimization, Seradyn Inc., p. 91-97.

The avidin latex, which was used as the IAC for the cyclosporin assay, was prepared by adsorption of avidin (Pierce Chemical Co) to latex particles as described in the references cited above.

The dansyl latex, which was used as the flow control solid phase for the cardiac assay, was prepared by reacting the bovine serum albumin latex with SMCC according to example 3. The resulting latex BSA-maleimide was reacted with dansyl thiol. The dansyl thiol was prepared by reduction of didansylcystein (Molecular Probes) with tributyl phosphine (Aldrich Chemical Co). The resulting dansyl BSA latex conjugate was purified on a gel filtration column and the eluted solids was centrifuged at top speed for 20 min in an Eppendorf centrifuge.

The solid phase latex solutions were reconstituted in phosphate buffer, pH 7.0 at a solids concentration of 1%, w/v.

The slid phases prepared in this manner were utilized for the time gate control of the cardiac assay, which comprised an anti-decapeptide antibody conjugate latex, for the flow control of the cardiac assay, a dansyl BSA conjugate latex, for the non-specific binding control of the cardiac assay, an anti-benzodiazapine antibody conjugate latex, for the troponin I assay, an anti-troponin antibody conjugate latex, for the CKMB assay, an anti-CKMB antibody conjugate latex and for the myoglobin assay, an anti-myoglobin conjugate latex. The solid phases utilized for the cyclosporin assay comprised an avidin conjugate latex for the time gate and flow controls and an anti-phencyclidine antibody conjugate latex for the cyclosporin assay.

Example 6

Preparation of FETL-Cyclosporin

FETL-BSA, (25 ml at 1% solids, w/v, 220 nm particles), prepared according to example 1, was reacted with 0.22 mg cyclosporin-N-hydroxysuccinimide (Novartis, Basel, Switzerland) after the addition of 2.5 ml dimethylformamide. The reaction stirred at room temperature for 30 min after addition of cyclosporin-H-hydroxysuccinimide. The reaction was quenched by addition of 1.1 ml of 0.5 M solution of taurine. The mixture was applied to a gel filtration column. The eluate containing the FETL-cyclosporin was centrifuged at top speed in an Eppendorf centrifuge for 20 min. The pellet was reconstituted in 10.5 ml 10 mM potassium phosphate, 2 mM potassium borate, 150 mM sodium chloride, pH 7.0 to a solids concentration of 2.2%, w/v.

Example 7

Preparation of FETL-Decapeptide Conjugate (IAC Label for Cyclosporin Assay)

To a solution of FETL-BSA, (15 ml at 1% solids, w/v, 220 nm particles), prepared according to example 1, was added with stirring, SMCC (25 µl of a 2 mg/ml solution in acetonitrile). The solution was incubated at room temperature for 2 h. The reaction was quenched by addition of 0.6 ml of 0.5 M solution of taurine. The solution was applied to a gel filtration column and 23.1 ml FETL-BSA-maleimide was eluted. A solution of decapeptide thiol (19 µl of 4.7 mM solution, see example 4 for the synthesis of decapeptide thiol) was added and the solution was incubated at room temperature for 50 min. The solution was applied to a gel filtration column and the eluted FETL-BSA-decapeptide was centrifuged at top speed in an Eppendorf centrifuge for 20 min. The pelleted FETL conjugate was resuspended to a final solids concentration of 2%, w/v in a phosphate buffered solution, pH 7.0.

Example 8

Preparation of Anti-Cyclosporin Phencyclidine Antibody and Anti-Decapeptide Biotin Antibody Conjugates Monoclonal antibodies to cyclosporin and decapeptide were used for the assay of cyclosporin and the IAC of the cyclosporin assay, respectively. These antibody conjugates were placed on the lid of the assay device and are termed lid antibodies. The anti cyclosporin antibody was reacted with phencyclidine thiol and the anti decapeptide antibody was reacted with biotin.

Thus, to a solution of anti cyclosporin antibody (1.0 ml at 10 mg/ml, Novartis) in 50 mM potassium phosphate, 10 mM potassium borate, 150 mM sodium chloride, pH 7, was added 22 µl of 2 mg/ml SMCC in acetonitrile with stirring. The solution was stirred at room temperature for 3 h. The solution was added to a gel filtration column equilibrated in 50 mM potassium phosphate, 10 mM potassium borate, 150 mM sodium chloride, pH 7. The anti cyclosporin maleimide was collected and was reacted with phencyclidine thiol. The phencyclidine thiol was prepared by hydrolysis of phencyclidine ATP. Phencyclidine ATP and phencyclidine thiol were synthesized according to examples 4 and 5, respectively, in U.S. Pat. No. 5,331,109. A solution of phencyclidine thiol (90 µl of 18 mM) was added to the anti cyclosporin maleimide with stirring. The solution was stirred at room temperature for 2.5 h. The antibody phencyclidine was applied to a gel filtration column equilibrated in 50 mM potassium phosphate, 10 mM potassium borate, 150 mM sodium chloride, pH 7. The eluted protein was collected in a 4 ml aliquot at 1.2 mg/ml.

To a solution of anti decapeptide antibody (0.5 ml at 10 mg/ml) was added 0.1 ml of 2 mg/ml biotin-N hydroxysuccinimide (Pierce Chemical Co.). The reaction stirred at room temperature for 2 h. The protein solution was added to a gel filtration column equilibrated in 50 mM potassium phosphate, 10 mM potassium borate, 150 mM sodium chloride, pH 7. The anti decapeptide biotin conjugate was eluted in 1 ml at 4.2 mg/ml.

Example 9

Preparation of Independent Assay Control for Cyclosporin Assays

The IAC for the cyclosporin assay comprised an FETL decapeptide conjugate (example 7) which was added to the base of the assay device in the reaction chamber with the FETL cyclosporin conjugate, an anti decapeptide biotin conjugate (example 8) which was added to the lid of the assay device with the anti cyclosporin biotin conjugate and an avidin conjugate latex (example 5) which was applied to the solid phase of the device in the diagnostic lane.

The solids concentration of the FETL decapeptide conjugate and the FETL cyclosporin conjugate was 0.04%, w/v in the reaction mixture. The antibody concentration of the anti decapeptide biotin antibody conjugate and the anti cyclosporin biotin antibody conjugate was 0.3 µg/ml in the reaction mixture. One skilled in the art will recognize that the absolute signal of the IAC can be adjusted higher or lower by raising or lowering, respectively, the concentrations of the IAC FETL and antibody conjugates, separately or together, in the reaction mixture.

Example 10

Preparation and Description of Assay Devices

Assay devices as described in U.S. Pat. No. 5,458,852 are utilized for this example; however, one skilled in the art recognizes that many assay devices and formats can be utilized for application of reagents and practicing the inventive teachings described herein. For example, assay devices incorporating membranes, as described in U.S. Pat. Nos. 4,200, 690, 4,391,904, 4,435,504, 4,857,453, 4,963,468, 5,073,484, 5,096,837 and 5,654,162, incorporated by reference only, also can be adapted to utilize the inventive teachings described herein.

Compositions of FETL-antibodies and FETL-ligands are added to the reaction chamber of the base so that the final assay solids concentration is between about 0.2% and 0.4% (w/v). The time gate control antibody is applied to the lid in the area of the reaction chamber to a final assay concentration of about 5 µg/ml. The solid phase antibody latexes are applied to the diagnostic lane in zones of about 2 mm×3 mm. In the case of assays utilizing a filter to remove red blood cells from plasma and debris in general from the sample, the device and filter are configured as described in U.S. patent application Ser. No. 08/704,804, filed Aug. 26, 1996, incorporated by reference. In the case of assays incorporating a lysis mesh for lysing whole blood, the device and lysis mesh are configured as described in U.S. Pat. No. 6,106,779, incorporated herein by reference in its entirety, including all figures, tables, and drawings. The time gate is applied to the device and functions as described in U.S. Pat. No. 5,458,852. The assay device lid is attached to the base by ultrasonic welding, as one skilled in the art will recognize.

One skilled in the art will also recognize that filters, lysis chambers, reaction chambers, time gates and diagnostic lanes in capillary devices are not prerequisites for practicing this invention. In addition, a reaction mixture can be formed in a test tube, incubated and applied to a membrane or a capillary such that the flow of the reaction mixture within the membrane or capillary is in a lateral fashion. The binding reactions of the label in the reaction mixture and the reagents on the solid phase of the membrane or the capillary take place after addition of the reaction mixture to the solid phase. The washing of unbound label from the binding zones can be accomplished by addition of a buffer containing detergent.

In general, assay devices used in these examples each comprise a time gate control and a flow control. In some cases, the time gate control IAC and the flow control IAC can be performed by one set of reagents. That is, a time gate control can also function as a flow control.

Immunoassay devices for cardiac markers, as described herein, each comprise a separate time gate control and a flow control and these IAC are independent of each other. The IAC antibody for the time gate control (anti morphine antibody decapeptide conjugate) is applied to the lid at concentrations that are adjusted relative to the dynamic range of the assay and range from about 0.1 µg/ml to 50 µg/ml and preferably 5 µg/ml in the reaction mixture. The labeled conjugates are applied to the reaction chamber and the solid phase capture reagents are applied to the diagnostic lane of the assay device. The concentrations of the IAC FETL conjugates were 0.06% solids, w/v, for the flow control and 0.12%, w/v, for the time gate control. One skilled in the art will recognize that the absolute signal of the IAC can be adjusted higher or lower by raising or lowering, respectively, the concentrations of the IAC FETL and antibody conjugates, separately or together, in the reaction mixture.

During the assay process when sample reconstitutes the reagents in the reaction chamber to form a reaction mixture, the anti-morphine antibody decapeptide conjugate binds to the FETL morphine conjugate. The time gate allows for an incubation, after which the reaction mixture flows through the diagnostic lane, during which the time gate control antibody binds to the time gate control label and analytes bind to their respective FETL antibody conjugates. The labels in the reaction mixture bind to the solid phase in the respective zones. Thus, the FETL morphine antimorphine antibody decapeptide conjugate complex binds to the immobilized anti decapeptide antibody, which defines the time gate control IAC, the FETL dansyl conjugate binds to the immobilized anti dansyl antibody, which defines a flow control IAC, the total FETL conjugates bind to the immobilized anti benzodiazapine, which defines non-specific binding to an antibody zone, the FETL anti CKMB antibody conjugate binds to the immobilized anti CKMB antibody in the presence of CKMB, the FETL anti troponin I antibody conjugate binds to the immobilized anti troponin I antibody in the presence of troponin I and the FETL anti myoglobin antibody conjugate binds to the immobilized anti myoglobin antibody in the presence of myoglobin. The IAC function to communicate with the instrument concerning the status of completion of the immunoassay and relevant information concerning non-specific binding to the solid phase in the diagnostic lane.

Immunoassay devices for cyclosporin comprise an IAC that functions similarly to the competitive immunoassay format which is performed for the measurement of cyclosporin. The cyclosporin assay device can also comprise a separate flow control, as described for the cardiac marker device. The IAC antibody (anti-decapeptide biotin) is applied to the lid with the anti-cyclosporin antibody at concentrations that are adjusted relative to the dynamic range of the assay. The labeled conjugates are applied to the reaction chamber and the solid phase capture reagents are applied to the diagnostic lane of the assay device. During the assay process when sample reconstitutes the reagents in the reaction chamber to form a reaction mixture, both anti-cyclosporin PCP conjugate and anti-decapeptide biotin conjugate bind to the FETL cyclosporin conjugate and FETL decapeptide conjugate, respectively. A ligand, for example in this case, decapeptide can also be added to the mesh in the lysis chamber so that it is reconstituted with the sample prior to the sample entering the reaction chamber. The ligand functions as an analyte so that the IAC behaves like the competitive immunoassay for cyclosporin. The time gate allows for an incubation, after which the reaction mixture flows through the diagnostic lane. The FETL cyclosporin anti cyclosporin antibody phencyclidine conjugate binds to the immobilized anti phencyclidine antibody, which defines the cyclosporin assay and the FETL decapeptide anti decapeptide biotin conjugate binds to the immobilized avidin, which defines the IAC. The IAC function to communicate with the instrument concerning the status of completion of the immunoassay and relevant information concerning non-specific binding to the solid phase in the diagnostic lane.

Example 11

Performing an Immunoassay

Several drops of sample (about 70 μl for whole blood into a device for lysing the sample, for example in the cyclosporin assay and about 180 μl whole blood or plasma for the device incorporating a filter) are added to assay devices, assembled as described in Example 6. The assay devices are placed in the instrument, immediately or any time up to about 30 min after sample addition. See, e.g., U.S. patent application Ser. No. 09/003,090, entitled "Immunoassay Fluorometer," Buechler et al., filed Jan. 5, 1998, now U.S. Pat. No. 6,830,731, and U.S. patent application Ser. No. 09/003,066, entitled "Media Carrier for an Assay Device," Buechler et al., filed Jan. 5, 1998, now U.S. Pat. No. 6,074,616. Several simple commands are prompted by the instrument, which one skilled in the art would be capable of performing and the instrument moves the assay device under the optical block for analysis of the capture zones and zones utilized for the timing function. After the instrument determines that the immunoassay in the device is completed, a result appears on the screen showing the concentration of the assayed analytes.

Example 12

Method for Defining Specific Capture Zone Locations in a Diagnostic Lane Using the IAC The diagnostic lane can be separated into three types of regions, the baseline zones, the capture zones, and the capture zone edges. FIG. 10 illustrates these regions. The identification of these regions will allow a different filter to be applied to each region, as described in example 13. The size and location of each of these regions will be utilized as a method of validating the trace, as described in example 14.

Two spots with known high signal to noise ratio are used as locating zones. In this assay these are two controls zones, as shown in FIG. 10. FIG. 10 represents the fluorescent scan of a cardiac panel device on which blood spiked with CKMB, troponin I and myoglobin was assayed. If the edges of each locating zone can be found and there is proper spacing between locating zones, then the expected location of the other zones is determined since the spacing between all the zones is a constant that is fixed by the solid phase application process. Therefore, the edges of the locating zones are used to define the expected locations of all the other zones. This procedure removes any positioning uncertainties by the measurement system or by the solid phase application system.

The capture zone edges are identified by their sharp rise out of the background signal. The approximate average signal height of the zone is utilized to define threshold heights that are 25, 50, and 75% of the average signal height. See FIG. 11. The point where the signal crosses the threshold defines the location of the threshold crossing. One skilled in the art will recognize that for a 50% threshold the left and right hand crossings define the full width at half maximum. This is commonly used as the width of the curve. The presence of noise can cause an error in the determination of the threshold crossing. To minimize the effect of noise on the determinations, the location of each threshold crossing is found by searching the edge in both directions, high to low and low to high. If the location of the threshold crossing is independent of the search direction then it has high reliability and is preferred over crossings that are dependent on the search direction. For a well-defined edge that is not affected by noise, the location of each threshold crossing is independent of the search direction and is within the expected range of positions of the transition. Reliability of the threshold crossing is rank by the following criteria.

1) The threshold crossing does not exist.
2) The threshold crossing exists.
3) The threshold crossing is direction independent.
4) The threshold crossing is within the expected range of positions of the transition.
5) The threshold crossing is within the expected range of positions of the transition and is direction independent.

The threshold crossing with the highest reliability defines the quality of the edge. The quality of the capture zone is defined by the edge with the poorest quality.

The location of the threshold crossing with the highest reliability is used to define a point on the capture zone edge, and the remainder of the capture zone edge is defined as the monotonic region around this point. Because noise in the signal can prematurely end the monotonic region, one non-monotonic point is allowed to be included in the capture zone edge provided that the next two points are again monotonic.

When the edges of each capture zone have thus been found, the trace can be divided into the three types of regions. Each of these regions will be treated differently by the custom digital filter. By definition the edges are rapidly changing monotonic regions. There is no need to filter these regions, so they are left unchanged. Example 13 details the filtering applied to the baseline zones and capture zones.

In FIG. 10, the capture zones (CZ) are the regions where signal is expected. In this example, the first two capture zones have well defined signals. Theses zones are control zones, and are used as locating zones. Capture zones on this device are the same width and equally spaced. The baseline zones (BL) are the regions between the capture zone. The capture zone edge is the transition from the baseline signal to the elevated capture zone signal.

In FIG. 11, the approximate 75%, 50%, and 25% thresholds are shown for six zones. The heights of these zones are scaled so they can all be plotted on the same graph. The third capture zone is noisy and the locations of all the threshold crossings depend on the direction searched. Furthermore, the 25% threshold will not be found on the left-hand side of the capture zone. The fourth capture zone has a spike on the right-hand edge. The 25% and 50% crossings will be dependent on the direction searched. The other capture zones have well defined edges and the locations of all threshold crossings are independent of the direction searched.

Example 13

Method for Smoothing the Fluorescence Measurement of the Diagnostic Lane and Defining the Capture Zone Signal Using the IAC This example illustrates the use of filter algorithms in conjunction with the three types of zones discussed in example 12. Each zone has unique characteristics, so the filtering applied to each zone is distinct. As noted in example 12, the capture zone edges are rapidly changing monotonic regions, so no filtering is applied to these zones.

The baseline zones are expected to be flat, so a low pass filter is applied to these regions. Normally a filter acts on a signal as a function of time, but the fluorescence signal is a function of position along the diagnostic lane. The low pass filter can be applied in both directions along the diagnostic lane. Using this symmetry each zone was filtered in both directions and the two results combined. This combination can take many forms including maximum, minimum, and average. The combined low pass filter results form the filtered baseline. It is observed that noise in the signal is dominated by spikes on the baseline. Therefore, it is assumed that the minima observed within the baseline zone represent the baseline. This dictates the use of the minimum of the left and right handed filters for the combined filter. FIG. 12 illustrates the results of this bi-directional filtering. The filter can also have separate time constants for increasing and decreasing signals. Selecting (down=0) will allow the filter to return to the baseline quickly. FIG. 13 illustrates the effects of different time constants. The filter can also include a maximum allowed rate of change. This limits the response to large glitches resulting in increased attenuation of glitches. FIG. 15 illustrates this effect.

The capture zone signal has a characteristic shape, which is fit to a function that approximates this shape. A parabola is a close approximation to the true, but unknown functional form of the capture zone. The parabola is found by a least squares fit. FIG. 14 shows examples of some characteristic capture zones and the resulting parabolic fit.

The base line zones surrounding the capture zone are used to define the baseline signal in the capture zone. This is accomplished via linear interpolation. The difference between the capture zone signal and the baseline is the signal from specific binding. This signal is summed over the capture zone and is the capture zone result. For details concerning capture zone derivations, see, e.g., U.S. application Ser. No. 08/065,528, Buechler, "Diagnostic Devices and Apparatus for the Controlled Movement of Reagents without Membranes," filed May 19, 1993; U.S. application Ser. No. 08/828, 041, Buechler, "Diagnostic Devices and Apparatus for the Controlled Movement of Reagents without Membranes," filed Mar. 27, 1997; and U.S. application Ser. No. 08/902,775, Buechler, "Diagnostic Devices and Apparatus for the Controlled Movement of Reagents without Membranes," filed Jul. 30, 1997; all of which are incorporated herein by reference including all figures, tables, and drawings.

The RMS deviations between the original signal and the filtered signals are used to define the noise in both the baseline zones and the capture zones. The signal to noise of a zone is defined as the ratio of the capture zone result to the noise of the zone.

One skilled in the art will recognize that glitches or other features that can be distinguished from the signals of interest can be eliminated prior to filtering. One method of finding these features is to use criteria such as width, and aspect ratio to define the range of allowed shapes, then check for the shapes by performing a correlation with candidates in the trace. Another method is to search for characteristic signatures in the derivatives of the trace. As shown in FIG. 15, these pre-filters can effectively eliminate a characteristic source of noise.

In FIG. 12, a section of a trace is plotted three times, each with a different filter applied. The LH Filter is the result when a filter is applied moving left to right. The RH Filter is the result when a filter is applied moving right to left. The filter applied is a low pass filter when the signal is increasing (up=1 mm) and does not filter decreasing signals (down=0 mm). The Combined trace is the minimum of the RH and LH filters.

In FIG. 13, a section of a trace is plotted twice with different filters applied. The first filter shows the effect of (down=0, up=1 mm). The second filter shows the effect of (up=down=1 mm). A predominate source of noise is spikes on top of a baseline signal. The use of the asymmetric filter preferentially selects for the lowest points.

In FIG. 14, characteristic shapes of capture zones with their corresponding parabolic fits are shown. The heights of these zones are scaled so they can all be plotted on the same graph.

In FIG. 15, the example shows a glitch with three different filters applied. The first filter is the combined filter of FIG. 12, with no limit on rate of change allowed. The second filter is also the combined filter, but now there is a maximum allowed rate of change. The third trace shows the effect of a glitch filter.

Example 14

Methods for Rejecting Assay Data Based on Faulty Devices or Samples Using the IAC The trace QC algorithm must decide if the assay results are valid. Validating each capture zone is accomplished by utilizing several criteria, including capture zone width and location, capture zone edge width and quality, and capture zone S/N and baseline S/N. While it is easy to define what constitutes acceptable and unacceptable criteria, there often remains a gray area between the acceptation and rejection cutoffs. A series of complex rules or fuzzy logic is required to decide the fate of a questionable assay. The digital filter treated capture zones differently than the baseline. This filter relied on an accurate determination of the capture zone edge. Therefore, if a capture zone fails the trace QC, it is assumed that the edges were incorrectly identified and the capture zone is filtered the same as the baseline zones.

The trace is validated by first rejecting bad capture zones, then accepting good capture zones, and then resolving any questionable capture zones. These three steps are performed in the following manner. The width of the capture zone, the location of the capture zone, the S/N of the capture zone, and the S/N the baseline zones are all compared to rejection criteria. If any of these four tests fail the capture zone is unacceptable, i.e. it failed trace QC. For remaining capture zones, the S/N of the capture zone and the edge quality are compared to acceptance criteria. A capture zone passes trace QC if it passes these two tests. A spot is questionable if it passes the rejection criteria but fails the acceptance criteria. Secondary criteria are used to resolve questionable capture zones. The secondary criteria require that both the capture zone width and the capture zone edge widths be within acceptable limits. The capture zone edge width is important because when the signal is small, a spike is often erroneously identified as an edge. The width of this edge is typically narrower than the width of a true capture zone edge.

A capture zone that fails trace QC does not exhibit the qualities expected from a clean signal, and therefore must be treated the same as baseline zones. The edges of the rejected capture zone are ignored and the baseline filter is applied to the capture zone and the two surrounding baseline zones. This newly filtered signal is re-integrated, yielding a new capture zone result. Any result above a noise threshold, set by the system noise, should have yielded an acceptable capture zone. A result from a capture zone that failed trace QC, which is above the noise threshold, can not be explained and must be rejected. Thus the capture zone fails quality control and the result from the zone is not reported. If the result from a capture zone that failed trace QC is below the noise threshold, it is assumed signal is limited by system noise, and the result is reported. FIG. 16 illustrates rejected zones that have been filtered by the baseline filter. One capture zone is above and one is below the noise threshold.

The baseline zones are an important part of the device quality control. Insufficient sample volume will result in a high or sloping baseline. Furthermore, as described in example 12, the baseline is subtracted from the capture zone signal prior to calculating the result. Therefore, accurate results require that the baseline signal behave as expected.

The baseline is validated by checking that the level is below a threshold level, or small compared to the amplitude of the adjacent capture zones. It is also validated by checking that the slope of the baseline zones is below a threshold level or small compared to the amplitude of the adjacent capture zones. The final validation check is that the second derivative (kinks) of the baseline zone is below a threshold level or small compared to the amplitude of the adjacent capture zones. FIG. 17 illustrates these tests. The amplitude ($BL_0$), slope ($BL_1$) and second derivative ($BL_2$) of the baseline at the capture zone are calculated. Each of these values is compared to the sum of the corresponding threshold level ($Th_x$) and the slope value ($m_x$) times the capture zone result (CZR) as shown in equation 14.1.

$$Bl_x > Th_x + m_x CZR \qquad \text{Eqn. 14.1}$$

The threshold level, set by the system noise, represents the maximum acceptable value when there is no capture zone signal. The slope value ($m_x$) sets the acceptable S/N for large capture zone signals. If a baseline zone fails quality control, i.e. equation 14.1 is true for any x, then the results from the corresponding capture zone is not reported. Some of the capture zones are control zones and control zone results must fall within an acceptable range. Each control zone result is compared to its minimum and maximum allowed values. If any control zone result falls outside of the acceptable range the entire test is rejected.

In FIG. 16, two capture zones are illustrated. The first zone is noisy and does not have well defined edges. The second zone is very wide, so its edges did not fall within the allowed region. These edges of these zones could not be accepted by the trace QC algorithm. Without edges, these zones are filtered the same as the baseline. The wide zone has a result that is above the noise threshold so the zone result is not reported. The noisy spot has a result that falls below the noise threshold, and is not rejected.

In FIG. 17, three traces are plotted, each with baseline problems. Good baselines are around 500 and are flat (see FIG. 10). The High Baseline trace is above 10,000, and exhibits a slope problem. The Sloping Baseline is higher than desired, but within acceptable limits. However, the slope makes it difficult to resolve the small signals, and these results are rejected. The High 2nd Derivative signal as a distinct kink. The result from a small signal near this kink is not reliable and therefore rejected.

Example 15

Methods for Detecting the Completion of an Immunoassay Using IACs

In this example several methods using IACs are demonstrated for the detection of immunoassay completion by an instrument. A preferred method is illustrated with a spike and recovery experiment using several immunoassay devices and an instrument controlled by a timing algorithm. All of the schemes discussed can be used to detect assay completion regardless of when the immunoassay device is inserted in the instrument. In most cases, assay completion is defined to be when the assay signals have reached steady state. In some cases (see Example 16), assay completion can occur before the assay signals have reached steady state. Steady state is defined as an absolute value of rate of change of signal that is less than a defined limit. In a preferred embodiment, steady state of a timing signal is defined as a negative rate of change whose absolute value is less than a defined limit.

Time Profiles of Assay and IAC Signals

The time-profiles of fluorescence signals from assay and IAC detection zones on the diagnostic lane of assay devices were determined in order to define the criteria used in timing algorithms to detect assay completion. The timing algorithm is a set of software instructions utilizing mathematical functions to define the completion of the assay. Immunoassay devices (example 10) were configured with detection zones for CKMB, troponin I, Myoglobin, a flow control, a timegate control and a non-specific binding control (cardiac panel devices). Human heparinized whole blood spiked with CKMB (Genzyme; 10 ng/ml), troponin I (Bio-tech International, Seattle, Wash.; 4 ng/ml) and myoglobin (Scripps Laboratories, San Diego, Calif.; 40 ng/ml) was added (example 11) to a cardiac panel device, and the device was inserted into an instrument within 1 minute. The instrument was programmed to scan the diagnostic lane (measure fluorescence as a function of position on the lane) every minute. The resultant data were transferred to a computer for analysis. The assay and control results were quantified by integrating the fluorescence over the detection zones with the background signal (measured between detection zones) subtracted (examples 12-14). The resultant integrated signals from the CKMB, troponin I and myoglobin detection zones were used to calculate concentrations of these respective analytes from previously determined calibration curves. In addition, the fluorescence signal (the timing signal) from a zone (the timing zone) downstream of the last detection zone was quantified. As there were no binding proteins immobilized in the timing zone, the timing signal was the sum of the fluorescence from unbound (unwashed) FETLs and non-specifically bound FETLS.

The time profiles of the integrated assay signals, control signals and the timing signal are shown in FIGS. 1 through 7. In general, the time profiles indicate that all the signals reach steady-state at about the same time (between 10 and 15 minutes). The data of FIG. 4 are used below to illustrate several embodiments of the use of IACs to determine assay completion.

Assay Completion Detected by Measurement of IAC Signal Values

In this embodiment, assay completion is defined to occur when some or all of the IAC signals are within defined acceptance windows. In many cases, the acceptance window will bracket the steady state values of the IAC signals. For example, in the case illustrated in FIGS. 1 through 7, the acceptance windows could be defined as follows: integrated flow control signal between 26 and 27, integrated timegate control signal between 340 and 350 and timing signal between 1 and 3. The only time all of the IACs were within these acceptance windows were after the assays (CKMB, troponin I and myoglobin) were at steady state. Therefore, the method of acceptance windows can be used to detect steady state (assay completion) with only a single measurement (at only one time) of the assay device as long as the assay signals reach steady state at the same time or before the IAC signals do. A device in which the immunoassay is complete when it is inserted into the instrument can be both checked for assay completion and read with only a single scan of the diagnostic lane. Therefore, measurement of said device is done as quickly as possible after insertion into the instrument. The disadvantage of the method of acceptance windows is that the windows must be wide enough to accommodate the normal variation (standard deviation) in signals among different devices and/or different blood samples. The acceptance window must be several (more than 2) standard deviations wide for at least 95% of the devices to eventually satisfy the acceptance criteria. Too wide of an acceptance window can lead to premature measurement of the assay signals (before steady state is reached). Therefore, this method is practical when the coefficients of variation (C.V.) of the IAC signals are small enough or when the variations (C.V.s) in IAC signals are well correlated with the variations in the assay signals and when the control signals are used to normalize the assay signals (Examples 16, 18, 19, 20 and 21). The method of acceptance windows can also be applied to cases in which assay completion is defined to occur before the IAC and assay signals reach steady state, for example when assay completion is defined to occur at a fixed time in the time-profile of the assay signal. When the assay is to be read before steady state is reached, and when the IAC and assay signals are correlated in time, the method of acceptance windows could lead to a better precision in the assay results than could be obtained by reading the assay signal at a fixed time. The better precision could result if the time-profiles of the assay and IAC signals were correlated with each other but varied among different assay devices.

Assay Completion Detected by Determination of Rate of Change of IAC Signals

In this embodiment some or all of the control, assay and/or timing signals are measured at least twice to determine if steady state has been reached within a defined limit for the maximum allowed rate of change of the signal. The data of FIG. 4 show that the assays are at steady state when the controls and timing signal are at steady state. Assay completion is defined to be when some or all of the control, assay and/or timing signals are at steady state. For many assay configurations, including that of the assay device described in this example, measurement of the negative rate of change of the timing signal provides an accurate and precise means of detection of assay completion. Measurement of the timing signal alone has the advantage that the instrument does not need to scan the entire diagnostic lane during the timing cycle, thus saving on power consumption and mechanical wear of the instrument. For some assay configurations, the timing signal alone may not provide adequate information or be large enough to determine if the assays have reached steady state. In these cases, in addition to measuring the timing signal, determination of the rate of change of some or all of the control and/or assay signals may be necessary to obtain accurate detection of assay completion.

Use of the Timing Signal to Detect Assay Completion of Immunoassay Devices

To illustrate the use of the timing signal to determine assay completion (steady state), six cardiac panel devices were run with human whole blood spiked with CKMB (8 ng/ml), troponin I (1.3 ng/ml) and myoglobin (110 ng/ml). The devices were inserted into instruments within one minute of adding the blood and the instrument software was started (example 11), placing all further control of the assay measurement under the instrument software.

The instrument positioned the assay devices such that the timing signal zone was under the optical block in position to be measured. The instrument measured the timing signal every ten seconds (each timing signal measurement is called a time-point). To smooth the timing signal time-profile (reduce the influence of random noise), the timing algorithm software averaged all the time-points in a window consisting of three consecutive time-points to obtain a time-point average. By advancing the window one time-point at a time, a series of overlapping time-point averages was computed. Steady state was defined to be when three consecutive time-point averages agreed with one another to within 3%. One skilled in the art will recognize that this criterion for steady state can be met at three distinct places (times) in the time-profile of the timing signal (FIG. 7). The first time the criterion can be met is immediately after the device is inserted into the meter before the timegate has broken when there is no fluorescence in the timing zone. The second time the criterion can be met is when the timing signal has reached its maximum value and is transitioning from rising to falling. The third time the criterion is met is when the timing signal comprises a negative rate of change and has dropped to its final steady state value. Only at this third time are the assays at steady state and ready to be measured. In the best mode, in order to avoid a premature reading of the device at the first two times, the timing algorithm required several additional criteria to be met before the assay device was read. They are: (i) the value of the timing signal had to be above the level expected for a device with no fluorescent label in the timing zone but below the maximum value expected in the timing signal time-profile (the acceptance window was a timing signal between 0.7 and 200 timing signal fluorescence units (FIG. 7); (ii) the first derivative of the timing signal had to be negative and (iii) the second derivative of the timing signal had to be positive. One skilled in the art will recognize that these criteria define a value and curvature (shape) for the timing signal time-profiles that in the instant case will occur only after steady state has truly been reached. Therefore, one skilled in the art will recognize that detection of steady state by these criteria does not require the instrument or the person using the instrument to know when the sample was added to the device or when the device was inserted into the instrument, and, in particular, does not require the person to insert the device into the instrument at any particular time.

Once all of the timing criteria discussed in the previous paragraph were met, the instrument read the assay signals (Example 11), processed the data and used stored calibration information to determine the concentrations of CKMB, troponin I and Myoglobin in the blood sample. The measured concentrations were then displayed on the LCD display of the instrument. In order to show that the assays had reached steady state when they were read by the instrument, the devices were re-inserted into the instrument about eleven minutes after they were first read (twenty six minutes after the blood was added) and read a second time.

The results are shown in Table 15.1. The total assay time is defined as the time between addition of the blood sample to the device and the display of the measured analyte concentrations on the LCD display the first time the device was read. The display of the concentrations occurred about one minute after the instrument concluded steady state was reached; the minute was required to scan the devices, calculate concentrations and display the results. The second time the devices were inserted into the meter (at twenty-six minutes), about two minutes elapsed between insertion of the devices and the display of the concentrations. The instrument, therefore, required about one minute of timing data acquisition to conclude that steady state had been reached. The mean and coefficient of variation (C.V.) of the CKMB, troponin I and myoglobin concentrations measured on the six assay devices are shown in Table 15.2. The mean concentrations and the concentration C.V.s were the same at the first (at approximately 15 minutes) and second (at approximately 26 minutes) reading of the devices. These results show that steady state had been reached at the time of the first reading of the devices.

TABLE 15.1

| Device | Total Assay Time When the Measurement Was Controlled by the Timing Algorithm | Measured CKMB Concentration (ng/ml) | | Measured Troponin I Concentration (ng/ml) | | Measured Myoglobin Concentration (ng/ml) | |
|---|---|---|---|---|---|---|---|
| | | Read at Time Determined by the Timing Algorithm | Read At 26 minutes | Read at Time Determined by the Timing Algorithm | Read At 26 minutes | Read at Time Determined by the Timing Algorithm | Read At 26 minutes |
| 1 | 13.8 | 6.7 | 6.4 | 1.15 | 1.11 | 98 | 99 |
| 2 | 15.3 | 8.5 | 8.5 | 1.35 | 1.31 | 104 | 108 |
| 3 | 15.2 | 6.8 | 6.9 | 1.30 | 1.21 | 103 | 103 |
| 4 | 15.2 | 7.8 | 7.9 | 1.20 | 1.20 | 111 | 111 |
| 5 | 14.7 | 9.1 | 9.3 | 1.55 | 1.54 | 110 | 111 |
| 6 | 15.5 | 9.2 | 9.2 | 1.34 | 1.26 | 107 | 109 |

TABLE 15.2

| Time Devices Read | Average measured concentration (ng/ml) | | | Coefficient of Variation (%) | | |
|---|---|---|---|---|---|---|
| | CKMB | Troponin I | Myoglobin | CKMB | Troponin I | Myoglobin |
| At steady state determined by timing algorithm | 8.0 | 1.3 | 106 | 14 | 11 | 5 |
| At 26 minutes | 8.0 | 1.3 | 107 | 15 | 11 | 5 |

Example 16

Use of IACs to Decrease the Time to Assay Completion

This example illustrates the use of IACs to normalize an immunoassay signal such that the normalized signal reaches steady state before the original signal. The normalized signal, therefore, provides a means of attaining assay completion and quantifying analyte concentrations more rapidly than with the unnormalized signal.

The immunoassay devices were configured with detection zones for Human Chorionic Gonadotropin (hCG), two flow controls (one with a high signal and one with a low signal) and an non-specific binding control. Human serum spiked with 100 mIU of hCG was added to the devices. The fluorescence from each of the detection zones was measured as a function of time using a fluorometer of local design. The fluorometer had essentially the same optical components as the instrument used for the measurements discussed in example 15.

The absolute fluorescence signal from the IAC and hCG detection zones is shown in FIG. 8. The IAC and hCG assay signals all reached steady state about 15 minutes after the serum sample was added to the device. In most cases, assay completion is defined to be when the assay signals reach steady state. Therefore, in this example, the assay signal measured after 15 minutes would be compared with a predetermined calibration curve to obtain the concentration of hCG in the serum sample. The entire assay from addition of the serum sample to the device to the display of the hCG concentration would take slightly longer than 15 minutes.

Normalization (the method is given in the next paragraph) of the assay signal with any of the IAC signals dramatically shortened the time for the normalized signal to reach steady state. The normalized signal (FIG. 9) reached steady state in about 8 minutes. The steady state value of the normalized signal was the same as the steady state value of the unnormalized signal. Therefore, the method of normalization resulted in an assay that would take only slightly longer than 8 minutes to obtain the final concentration values and that would not change the calibration curve.

The assay signal was normalized to each of the IACs using equation 17.5 (example 17). The function f (equation 17.4) was determined by plotting the deviations of the assay signal at each time from the final steady state value (equation 17.2; Ave(Assay)t=(was determined from the single device of this example) as a function of the deviations of the IAC signals at each time from the final steady state values (equation 17.1; Ave(IAC)t=(was determined from the single device of this example). The resulting curves were fit with parabolic functions using the curve fitting routine of Sigma Plot (Jandel Scientific version 2.01). Therefore, the function f was a second order power series with coefficients given by the fit.

Example 17

Equations for the Normalization of Assay Signals With One IAC

This example shows the equations used to normalize an assay signal using a single IAC. These equations apply both to assay and IAC signals at steady state and to assay and IAC signals that are changing with time. The concepts developed here can be extended to apply to the linear combination of two or more IACs to normalize the assay signals to multiple IACs that, for example, monitor both flow rate and incubation time.

The method of normalization utilizes the deviations of the IACs and the assay signals from their respective mean steady state values. The mean steady state values are measured empirically using assay methods and assay devices identical to those in which normalization will take place. One skilled in the art will recognize that this is best accomplished using a variety of samples, for example, blood from about 5 to 100 individuals. Additionally, diversity in samples can be achieved by pooling samples from individuals, for example, by making plasma, serum or urine pools. Diversity in the samples or sample pool used for defining the mean of the IAC and assay signals improves the probability that the normalization routine will apply to all samples to be tested. Thus, measurements should be made to obtain an accurate value for the mean steady state signals. The deviations are defined as follows:

$$\Delta(IAC)_{i,t} = \{(IAC)_{i,t} - Ave(IAC)_{t=\infty}\}/Ave(IAC)_{t=\infty} \quad \text{Eqn. 17.1}$$

$$\Delta(Assay)_{i,t} = \{(Assay)_{i,t} - Ave(Assay)_{t=\infty}\}/Ave(Assay)_{t=\infty} \quad \text{Eqn. 17.2}$$

where $\Delta(IAC)_{i,t}$ and $(Assay)_{i,t}$ are the deviations of the IAC and assay signals, respectively, for the i'th immunoassay device at time t, $(IAC)_{i,t}$ and $(Assay)_{i,t}$ are the IAC and assay signals, respectively, for the i'th immunoassay device at time t and $Ave(IAC)_{t=\infty}$ and $Ave(Assay)_{t=\infty}$ are the mean IAC and assay signals at steady state, respectively, determined by averaging the respective steady state ($t=\infty$) signals over a sufficient number of devices. The number of devices included in the average can be as low as 1 and depends on the accuracy needed and the precision of the measurement. One of ordinary skill will recognize how to determine the number of devices required in the average.

Algebraic rearrangement of equation 17.2 leads to the equation:

$$Ave(Assay)_{t=\infty} = \{(Assay)_{i,t}\}/\{1+\Delta(Assay)_{i,t}\} \quad \text{Eqn. 17.3}$$

In general, the goal in any normalization scheme is to normalize the assay signal of the i'th device at any time t (i.e., $(Assay)_{i,t}$) to obtain the average steady state signal (i.e., $Ave(Assay)_{t=\infty}$), since the average steady state signal is used to derive the calibration information for the assay. The deviation $\Delta(Assay)_{i,t}$ will in general not be known, since the concentration of the analyte in the sample and therefore, the expected average steady state assay signal, will not be known. However, the deviation $\Delta(Assay)_{i,t}$ can be calculated from the deviation $\Delta(IAC)_{i,t}$. Since the IAC signal is independent of the analyte concentration, the expected value for the IAC signal is the same as the average steady state value. Therefore, for each of the i assay devices, $\Delta(IAC)_{i,t}$ can be calculated from the IAC signal, $(IAC)_{i,t}$, and the previously determined average steady state IAC signal, $Ave(IAC)_{t=\infty}$, using equation 1. The IACs and the assays are set up such that their signals are correlated in time and/or over all the i devices. If the IACs and assays are correlated, a relationship will by definition exist between their deviations, i.e., $\Delta(Assay)_{i,t}$ will be a function f of $\Delta(IAC)_{i,t}$:

$$\Delta(Assay)_{i,t} = f(\Delta(IAC)_{i,t}) \quad \text{Eqn. 17.4}$$

Substitution of equation 17.4 into equation 17.3 and equating the normalized assay signal norm(assay)$_i$ from the i'th device with $Ave(Assay)_{t=\infty}$ leads to:

$$Norm(assay)_{i,t} = \{(Assay)_{i,t}\}/\{1+f(\Delta(IAC)_{i,t})\} \quad \text{Eqn. 17.5}$$

Once the function f that relates the deviations of the assay and the IAC is known, equation 17.5 can be used to normalize assay signals to be the same as the mean steady state values averaged over many devices. Examples are given herein (Examples 16, 18-21) in which f is either a first order or second order power series and in which Eqn. 17.5 (or Eqn. 17.7) is used to decrease the time to assay completion (example 16), to normalize out the effect of variable timegate times (example 19) and to improve the accuracy and precision of the measurement of various analytes (examples 18, 20 and 21). One skilled in the art will recognize that f can be many functions. In particular, f can be a Taylor series expansion such that any functional relationship between the deviations of the IAC and assay signals that obeys the criteria for defining a Taylor series can be exploited.

A special case of equation 17.4 is when the deviations of the assay and IAC signals are equal:

$$\Delta(Assay)_{i,t} = \Delta(IAC)_{i,t} \quad \text{Eqn. 17.6}$$

In this special case, equation 17.5 reduces to the simple ratio:

$$Norm(assay)_{i,t} = \{(Assay)_{i,t}/(IAC)_{i,t}\} \cdot Ave(IAC)_{t=\infty} \quad \text{Eqn. 17.7}$$

Example 18

Use of IAC to Improve Reproducibility of Analyte Measurement Among Plasma Samples From Several Different Individuals Immunoassay of analytes in plasma, serum or whole blood samples can be problematic because of the matrix effect, in which the result of the immunoassay varies among samples from different individuals even though all the samples contain the same concentration of analyte. The causes of the matrix effect are many and depend on the exact nature of the immunoassay. In general, the differences in the physical (viscosity, optical density, etc) and chemical (substances that interfere with the assays) properties of the samples contribute to the matrix effect. One method of reducing the influence of the matrix effect is to use an IAC to normalize the immunoassay. In order to work properly, the changes in the IAC and the analyte assay associated with the matrix effect must be correlated, i.e., the deviations of the analyte assay must be related to the deviations of the IAC by a function (Eqn. 17.4 of example 17). In this example, the timegate control IAC is used to normalize and improve the reproducibility of the measurement of CKMB on cardiac panel devices (Example 15) among plasma samples from several different individuals.

Cardiac panel devices (Example 15) were run with plasma from different individuals spiked with 20 ng/ml CKMB. Each sample was run on eight devices and the results were averaged. The results from nine individuals chosen at random were used to define the functional relationship between the timegate control IAC and the CKMB Assay. The deviations $\Delta(IAC)_i$ and $\Delta(Assay)_i$ were calculated from equations 17.1 and 17.2 respectively. The subscript t=time has been dropped because all of the measurements were made at steady state (t=∞). The subscript i refers to the i'th plasma sample, i.e., from the i'th individual (i=1 to 9). The values of Ave(IAC) and Ave(Assay) were defined to be the mean IAC and Assay signals, respectively, averaged over the nine plasma samples. Therefore, each value, $\Delta(IAC)_i$ or $\Delta(Assay)_i$, represents the deviation for the i'th plasma sample of the timegate control or CKMB assay signal, respectively, from the mean timegate control or CKMB assay signal averaged over all nine plasma samples. The resultant data pairs ($\Delta(IAC)_i$, $\Delta(Assay)_i$) were plotted and fitted with a line using the curve fitting routine of Sigma Plot (Jandel Scientific). The functional relationship thus obtained between the two deviations was:

$$\Delta(Assay)_i = 0.30 \cdot \Delta(IAC)_i \quad \text{Eqn. 18.1}$$

Therefore, the normalization equation (Eqn. 17.5) is:

$$Norm(assay)_i = \{(Assay)_i\}/\{1+0.30 \cdot \Delta(IAC)_i\} \quad \text{Eqn. 18.2}$$

To demonstrate the effect of normalization on reproducibility of analyte measurement, plasma samples from four individuals were spiked with 20 ng/ml CKMB an run on cardiac panel devices (the results from eight devices per plasma sample were averaged). The resultant non-normalized timegate control signal and measured CKMB signals are shown in Table 18.1. The measured CKMB signals were normalized using Eqn. 18.2. The timegate control signal deviation $\Delta(IAC)_i$ was calculated using equation 17.1 where the value of Ave(IAC) was determined by averaging the timegate control signals over the four plasma samples. The normalized CKMB signals are shown in Table 18.1. The mean non-normalized and normalized CKMB signals averaged over the four plasma samples are the same. However, the C.V. calculated among the four plasma samples is dramatically lower for the normalized CKMB signals. Therefore, the use of the timegate control IAC to normalize the CKMB signals dramatically improved reproducibility among different plasma donors by normalizing out the matrix effects.

TABLE 18.1

| Plasma Sample (Donor) | Timegate Control Signal | Unnormalized CKMB Signal | Normalized CKMB Signal |
|---|---|---|---|
| 1 | 157 | 133 | 119 |
| 2 | 105 | 121 | 123 |
| 3 | 93.8 | 117 | 123 |
| 4 | 93.7 | 106 | 112 |
| Average of 1-4 | 112 | 119 | 119 |
| C.V. of 1-4 | 27% | 9.4% | 4.4% |

Example 19

Use of an IAC to Correct an Immunoassay for Variations in the Incubation Time of the Sample With the Antibody Reagents One potential source of imprecision or error in an immunoassay is the failure to incubate the sample with the antibody reagents for the right amount of time (usually until binding equilibrium is obtained). On the other hand, it may be desirable in some cases to purposely shorten the incubation time in order to shorten the time to assay completion. In either case, an IAC whose signal varies with the incubation time in a way that is correlated with the variation in the assay signal with the incubation time can be used to normalize the assay signal. The normalized assay signal will be essentially independent of the incubation time of the sample with the antibody reagents. The normalization could, therefore, lead to improved assay precision and accuracy and to shorter assay times.

To illustrate the use of an IAC to correct the assay signals for variations in the time of incubation of the sample with the antibody reagents, cardiac panel devices were constructed with timegates whose hold-time (timegate time) could be varied from 0 to 4 minutes. Human whole blood spiked with CKMB (5 ng/ml final), troponin I (5 ng/ml final) and myoglobin (50 ng/ml final) was run on the devices. The timegate time was adjusted to be 0.0 minutes, 1 minute or 4 minutes. Thirty devices were run with each timegate time. The averaged timegate control and assay signals that were obtained for devices run with each timegate time are shown in Table 19.1.

The timegate control and assay signals are all correlated with the timegate time, i.e., are lower for a timegate time of 0.0 minutes than for the longer timegate times. The timegate control involves the binding of an anti-morphine antibody to FETL-morphine in the reaction chamber to form a signal generating complex. The kinetics of this reaction are slow enough that the reaction is not complete when the timegate time is less than 1 minute. Similarly, the kinetics of the binding of the CKMB, troponin I and myoglobin to their respective antibodies on the FETLs to form a signal generating complex are slow enough that these reactions are not complete when the timegate time is less than 1 minute. In order to obtain the best normalization of the analyte assay signals with the IAC signals over all timegate times, the binding kinetics associated with forming the IAC signal generating complex should be as similar as possible to the binding kinetics associated with forming the analyte assay signal generating complex.

The analyte assay signals in Table 19.1 were normalized with the IAC signal using the methods of example 17. The normalization equation was:

$$\text{Norm}(\text{assay})_t = \{(\text{Assay})_t\}/\{1 + m \cdot \Delta(IAC)_t\} \qquad \text{Eqn. 19.1}$$

The subscript t refers to the timegate time in this example. Since individual devices were not analyzed, the subscript i has been dropped. The deviations $\Delta(IAC)_t$ and $\Delta(\text{assay})_t$ were determined using equations 17.1 and 17.2, respectively, where $\text{Ave}(IAC)_{t=\infty}$ and $\text{Ave}(\text{assay})_{t=\infty}$ were calculated from the average of the values for timegate times of 1 minute and 4 minutes. The slopes m in Eqn. 12 were determined by plotting the data pairs ($\Delta(IAC)_t$, $\Delta(\text{assay})_t$) and fitting the resultant lines using the curve fitting routine in Sigma Plot. The slopes are:
CKMB: m=1.0
Troponin I: m=0.43
Myoglobin: m=0.34

The normalized assay signals are shown in Table 19.1. The normalization significantly corrects the signals obtained for the 0 minute timegate to be similar to the final equilibrium values obtained for 1 minute or 4 minute timegates. Therefore, the normalization could result in better assay precision in cases where the imprecision in the timegate time is a factor and could also result in faster assay times by eliminating the need for a timegate.

TABLE 19.1

| Timegate Time | Timegate Control Signal | CKMB Signal | Normalized CKMB Signal | Troponin I Signal | Normalized Troponin I Signal | Myoglobin Signal | Normalized Myoglobin Signal |
|---|---|---|---|---|---|---|---|
| 0 min | 49 | 69 | 108 | 77 | 91 | 541 | 616 |
| 1 min | 82 | 107 | 101 | 89 | 87 | 621 | 609 |
| 4 min | 72 | 122 | 130 | 98 | 101 | 620 | 620 |
| Average of All Times | 68 | 99 | 113 | 88 | 93 | 594 | 615 |
| C.V.s of All Times | 25% | 28% | 13% | 12% | 7.8% | 7.7% | 0.9% |

Example 20

Use of an IAC to Improve Assay Precision and Accuracy in a Cyclosporin Assay This example illustrates the use of an IAC to normalize the assay signals from a cyclosporin immunoassay device run with whole blood to improve the precision (C.V.) and accuracy of the assay. Three issues are addressed: (i) the precision of the cyclosporin measurement within samples from single blood donors; (ii) the accuracy of the cyclosporin measurement in blood from four different blood donors and (iii) the accuracy and precision of the cyclosporin measurement in blood of different hematocrit values from the same blood donor.

Whole blood from four different blood donors was spiked with cyclosporin (CS) to final total concentrations of 0 ng/ml CS, 50 ng/ml CS, 100 ng/ml CS and 800 ng/ml CS. Each spiked blood sample was run on approximately 18 immunoassay devices (examples 10 and 11) with detection zones for cyclosporin and an IAC. The assay devices were inserted into an instrument and read about 20 minutes after addition of the blood.

The integrated assay and IAC signals from each device run with the blood donor samples spiked to 50 ng/ml CS are shown in Table 20.1 The normalized assay signals are also shown in the table and were calculated from the assay signal and IAC signal using the following equation:

normalized assay signal=(assay signal/IAC signal)×1000     Eqn. 20.1.

The C.V.s of the normalized assay signals are significantly lower than the C.V.s of the non-normalized assay signals.

The cyclosporin measurements at all the spiked cyclosporin concentrations are summarized in Table 20.2. For each individual sample (i.e., each cyclosporin concentration in blood from each individual donor), the table shows the mean and C.V. of the assay, IAC and normalized assay signals averaged over the 18 devices run with the sample. In addition, the table shows the mean and C.V. of the assay, IAC and normalized assay signals averaged over the blood samples from all four donors (inter-donor C.V.s). The data show that the C.V. of the normalized assay signal is less than that of the non-normalized signal for every donor and every cyclosporin concentration tested. Furthermore, the inter-donor C.V.s of the normalized signals are significantly lower than those of the non-normalized signals. Therefore, the data show that the normalization of the assay signals with the IAC signals significantly improves the precision of the cyclosporin measurement within one sample (blood donor) and that the normalization reduces or eliminates the effect of the matrix (different blood donor samples) on the cyclosporin measurement.

The effect of normalization on the accuracy and precision of the cyclosporin measurement was also investigated in blood samples of varied hematocrit values. The hematocrit of the blood from a single blood donor was adjusted to three levels by centrifuging the blood and removing or adding plasma from the same donor as appropriate. Three hematocrits were tested (low=29%, medium=37% and high=45%) at three cyclosporin concentrations: 0 ng/ml CS, 100 ng/ml CS and 400 ng/ml CS. The results are shown in Table 20.3. For each individual sample (i.e., each cyclosporin concentration in blood at each hematocrit value), the table shows the mean and C.V. of the assay, IAC and normalized assay signals averaged over the 18 devices run with the sample. In addition, the table shows the mean and C.V. of the assay, IAC and normalized assay signals averaged over the low, medium and high hematocrit samples. The data show that the C.V. of the normalized assay signal is less than that of the non-normalized signal for every hematocrit and every cyclosporin concentration tested. Furthermore, the C.V. computed by averaging the signals from the low, medium and high hematocrit samples is significantly lowered by normalization of the assay signal. The data therefore show that the normalization of the assay signals with the IAC signals significantly improves the precision of the cyclosporin measurement within one sample (hematocrit) and that the normalization essentially eliminates the effect of hematocrit on the cyclosporin measurement over the range of hematocrits tested.

In summary, all of the data presented in this example show that normalization of the assay signals with the IAC signals significantly improves the precision and accuracy of the cyclosporin measurement.

TABLE 20.1

| Device # | Donor 1 Assay Signal | Donor 1 IAC Signal | Donor 1 Norm.* Signal | Donor 2 Assay Signal | Donor 2 IAC Signal | Donor 2 Norm. | Donor 3 Assay Signal | Donor 3 IAC Signal | Donor 3 Norm. Signal | Donor 4 Assay Signal | Donor 4 IAC Signal | Donor 4 Norm. |
|---|---|---|---|---|---|---|---|---|---|---|---|---|
| 1 | 375 | 884 | 424 | 463 | 1048 | 442 | 385 | 943 | 409 | 394 | 989 | 398 |
| 2 | 514 | 1080 | 476 | 431 | 972 | 443 | 329 | 819 | 402 | 514 | 1189 | 432 |
| 3 | 423 | 1011 | 418 | 557 | 1158 | 481 | 483 | 1176 | 410 | 530 | 1211 | 438 |
| 4 | 477 | 1075 | 444 | 453 | 1005 | 451 | 351 | 922 | 380 | 550 | 1240 | 443 |
| 5 | 638 | 1310 | 487 | 483 | 1042 | 464 | 495 | 1151 | 430 | 615 | 1355 | 454 |
| 6 | 475 | 1119 | 425 | 473 | 1106 | 428 | 467 | 1145 | 408 | 631 | 1436 | 439 |
| 7 | 521 | 1085 | 480 | 489 | 1075 | 455 | 540 | 1282 | 422 | 584 | 1303 | 448 |
| 8 | 442 | 936 | 472 | 344 | 800 | 430 | 565 | 1238 | 457 | 540 | 1097 | 492 |
| 9 | 437 | 992 | 440 | 400 | 898 | 446 | 448 | 1034 | 434 | 423 | 945 | 448 |
| 10 | 427 | 979 | 436 | 443 | 1012 | 438 | 409 | 1023 | 399 | 600 | 1258 | 477 |
| 11 | 414 | 932 | 444 | 381 | 933 | 409 | 425 | 1031 | 412 | 467 | 1134 | 412 |
| 12 | 336 | 800 | 419 | 456 | 1018 | 448 | 687 | 1370 | 501 | 623 | 1294 | 481 |
| 13 | 481 | 1010 | 476 | 445 | 1006 | 442 | 470 | 1147 | 410 | 433 | 1011 | 428 |
| 14 | 497 | 1134 | 439 | 412 | 950 | 434 | 501 | 1187 | 422 | 608 | 1254 | 485 |
| 15 | 345 | 837 | 412 | 539 | 1187 | 454 | 620 | 1378 | 450 | 468 | 1148 | 408 |
| 16 | 430 | 998 | 431 | 503 | 1136 | 442 | 400 | 980 | 409 | 538 | 1229 | 438 |
| 17 | 406 | 897 | 453 | 439 | 1033 | 425 | 688 | 1290 | 533 | 448 | 1027 | 436 |
| 18 | 506 | 1044 | 484 | 458 | 937 | 488 | | | | | | |
| Mean | 452 | 1007 | 448 | 454 | 1018 | 446 | 486 | 1125 | 429 | 527 | 1183 | 445 |
| C.V. | 16 | 12 | 6 | 11 | 9 | 4 | 22 | 14 | 9 | 15 | 12 | 6 |

*"Norm." refers to a normalized assay signal, or a corrected assay signal.

The cyclosporin measurements at all the spiked cyclosporin concentrations are summarized in Table 20.2. For each individual sample (i.e., each cyclosporin concentration in blood from each individual donor), the table shows the mean and C.V. of the assay, IAC and normalized assay signals averaged over the 18 devices run with the sample. In addition, the table shows the mean and C.V. of the assay, IAC and normalized assay signals averaged over the blood samples from all four donors (inter-donor C.V.s). The data show that the C.V. of the normalized assay signal is less than that of the non-normalized signal for every donor and every cyclosporin concentration tested. Furthermore, the inter-donor C.V.s of the normalized signals are significantly lower than those of the non-normalized signals. Therefore, the data show that the normalization of the assay signals with the IAC signals significantly improves the precision of the cyclosporin measurement within one sample (blood donor) and that the normalization reduces or eliminates the effect of the matrix (different blood donor samples) on the cyclosporin measurement.

TABLE 20.2

| | Assay Signal | Assay Signal CV | IAC Signal | IAC Signal C.V. | Normalized Assay Signal | Normalized Assay Signal C.V. |
|---|---|---|---|---|---|---|
| | | | 0 ng/ml CS | | | |
| Donor 1 | 682 | 15 | 1113 | 9 | 610 | 7 |
| Donor 2 | 653 | 18 | 1062 | 14 | 614 | 8 |
| Donor 3 | 684 | 19 | 1154 | 14 | .589 | 7 |
| Donor 4 | 753 | 21 | 1219 | 16 | 615 | 10 |
| Average | 693 | | 1137 | | 607 | |
| CV | 6 | | 6 | | 2 | |
| | | | 50 ng/ml CS | | | |
| Donor 1 | 452 | 16 | 1007 | 12 | 448 | 6 |
| Donor 2 | 454 | 11 | 1018 | 9 | 446 | 4 |
| Donor 3 | 486 | 22 | 1125 | 14 | 429 | 9 |
| Donor 4 | 527 | 15 | 1183 | 12 | 445 | 6 |
| Average | 480 | | 1083 | | 442 | |
| CV | 7 | | 8 | | 2 | |
| | | | 100 ng/ml CS | | | |
| Donor 1 | 245 | 13 | 1012 | 10 | 242 | 7 |
| Donor 2 | 228 | 15 | 955 | 13 | 239 | 6 |
| Donor 3 | 236 | 16 | 1083 | 13 | 218 | 7 |
| Donor 4 | 238 | 17 | 1049 | 14 | 227 | 6 |
| Average | 237 | | 1025 | | 231 | |
| CV | 3 | | 5 | | 5 | |
| | | | 800 ng/ml CS | | | |
| Donor 1 | 101 | 13 | 1090 | 11 | 93 | 7 |
| Donor 2 | 74 | 14 | 927 | 15 | 80 | 8 |
| Donor 3 | 82 | 16 | 1097 | 13 | 74 | 5 |
| Donor 4 | 80 | 14 | 1054 | 14 | 76 | 5 |
| Average | 84 | | 1042 | | 81 | |
| CV | 14 | | 8 | | 10 | |

The effect of normalization on the accuracy and precision of the cyclosporin measurement was also investigated in blood samples of varied hematocrit values. The hematocrit of the blood from a single blood donor was adjusted to three levels by centrifuging the blood and removing or adding plasma from the same donor as appropriate. Three hematocrits were tested (low=29%, medium=37% and high=45%) at three cyclosporin concentrations: 0 ng/ml CS, 100 ng/ml CS and 400 ng/ml CS. The results are shown in Table 20.3. For each individual sample (i.e., each cyclosporin concentration in blood at each hematocrit value), the table shows the mean and C.V. of the assay, IAC and normalized assay signals averaged over the 18 devices run with the sample. In addition, the table shows the mean and C.V. of the assay, IAC and normalized assay signals averaged over the low, medium and high hematocrit samples. The data show that the C.V. of the normalized assay signal is less than that of the non-normalized signal for every hematocrit and every cyclosporin concentration tested. Furthermore, the C.V. computed by averaging the signals from the low, medium and high hematocrit samples is significantly lowered by normalization of the assay signal. The data therefore show that the normalization of the assay signals with the IAC signals significantly improves the precision of the cyclosporin measurement within one sample (hematocrit) and that the normalization essentially eliminates the effect of hematocrit on the cyclosporin measurement over the range of hematocrits tested.

In summary, all of the data presented in this example show that normalization of the assay signals with the IAC signals significantly improves the precision and accuracy of the cyclosporin measurement.

TABLE 20.3

| | Assay Signal | Assay Signal CV | IAC Signal | IAC Signal CV | Normalized Assay Signal | Normalized Assay Signal C.V. |
|---|---|---|---|---|---|---|
| | | | 0 ng/ml CS | | | |
| Low | 421 | 10 | 509 | 11 | 829 | 3 |
| Med | 520 | 12 | 645 | 10 | 806 | 5 |
| High | 741 | 10 | 848 | 10 | 877 | 7 |
| Average | 561 | | 667 | | 837 | |
| CV | 29 | | 26 | | 4 | |
| | | | 100 ng/ml CS | | | |
| Low | 235 | 9 | 507 | 9 | 464 | 6 |
| Med | 289 | 11 | 637 | 9 | 453 | 4 |
| High | 342 | 13 | 705 | 11 | 486 | 6 |
| Average | 288 | | 616 | | 468 | |
| CV | 19 | | 16 | | 4 | |
| | | | 400 ng/ml CS | | | |
| Low | 93 | 10 | 457 | 10 | 203 | 6 |
| Med | 103 | 8 | 565 | 12 | 184 | 8 |
| High | 143 | 14 | 800 | 11 | 179 | 12 |
| Average | 113 | | 607 | | 189 | |
| CV | 23 | | 29 | | 7 | |

Example 21

Use of an IAC to Improve the Precision of an Assay for CKMB, Troponin I and Myoglobin Human plasma spiked with CKMB (5 ng/ml), troponin I (2 ng/ml) and myoglobin (70 ng/ml) was assayed for these analytes on cardiac panel immunoassay devices (23 devices) which were read in an instrument as described in previous examples. The assay signals for CKMB, troponin I and myoglobin measured in each immunoassay device are shown in Table 21.1. The normalized assay signals are also shown in the table and were calculated from the flow control signal and the assay signals using equation 17.7 (example 17). The C.V.s of the normalized signals are significantly lower than those of the non-normalized signals. Therefore, the data show that normalization of the assay signals with the IAC flow control improves the precision the CKMB, troponin I and myoglobin assays.

TABLE 21.1

| Device # | Flow Control Signal | CKMB | | Troponin I | | Myoglobin | |
|---|---|---|---|---|---|---|---|
| | | Assay Signal | Normalized Assay Signal | Assay Signal | Normalized Assay Signal | Assay Signal | Normalized Assay Signal |
| 1 | 70.9 | 14.3 | 13.6 | 15.2 | 14.5 | 94.0 | 89.4 |
| 2 | 75.2 | 13.9 | 12.5 | 15.7 | 14.0 | 97.4 | 87.2 |
| 3 | 71.7 | 14.4 | 13.6 | 14.8 | 13.9 | 97.2 | 91.4 |
| 4 | 63.1 | 13.0 | 13.8 | 11.4 | 12.2 | 88.2 | 94.3 |
| 5 | 62.0 | 11.4 | 12.3 | 13.9 | 15.2 | 80.1 | 87.1 |
| 6 | 71.1 | 12.7 | 12.0 | 14.2 | 13.4 | 82.9 | 78.7 |
| 7 | 65.1 | 11.9 | 12.3 | 12.8 | 13.3 | 82.4 | 85.2 |
| 8 | 79.1 | 15.8 | 13.5 | 15.0 | 12.7 | 95.3 | 81.2 |
| 9 | 65.8 | 12.4 | 12.7 | 13.7 | 14.1 | 95.9 | 98.2 |
| 10 | 62.9 | 12.9 | 13.8 | 14.8 | 15.9 | 86.2 | 92.3 |
| 11 | 67.5 | 15.7 | 15.7 | 14.2 | 14.2 | 96.2 | 96.0 |
| 12 | 59.4 | 10.4 | 11.8 | 11.0 | 12.4 | 75.6 | 85.9 |
| 13 | 67.6 | 9.8 | 9.8 | 11.4 | 11.4 | 80.8 | 80.5 |
| 14 | 69.4 | 12.0 | 11.6 | 14.5 | 14.1 | 89.2 | 86.6 |
| 15 | 72.8 | 14.8 | 13.7 | 15.3 | 14.1 | 104.2 | 96.5 |
| 16 | 71.0 | 13.3 | 12.6 | 14.4 | 13.7 | 91.6 | 86.9 |
| 17 | 61.4 | 11.4 | 12.5 | 12.0 | 13.2 | 79.1 | 86.9 |
| 18 | 59.5 | 9.6 | 10.9 | 11.2 | 12.6 | 70.4 | 79.7 |
| 19 | 64.7 | 12.2 | 12.7 | 13.6 | 14.2 | 88.5 | 92.3 |
| 20 | 73.3 | 13.7 | 12.6 | 13.4 | 12.3 | 91.4 | 84.0 |
| 21 | 64.3 | 11.4 | 11.9 | 12.3 | 12.9 | 84.1 | 88.2 |
| 22 | 64.3 | 12.1 | 12.7 | 10.8 | 11.3 | 72.6 | 76.1 |
| 23 | 68.3 | 10.6 | 10.5 | 12.9 | 12.8 | 78.7 | 77.6 |
| Average | 67.4 | 12.6 | 12.6 | 13.4 | 13.4 | 87.0 | 87.1 |
| C.V. | 7.7 | 13.7 | 9.9 | 11.4 | 8.3 | 10.1 | 7.1 |

The various embodiments of the invention described above may be implemented using hardware, software or a combination thereof and may be implemented in a computer system or other processing system. In fact, in one embodiment, these elements are implemented using a computer system capable of carrying out the functionality described with respect thereto. An example computer system 702 is shown in FIG. 18. The computer system 702 includes one or more processors, such as processor 704. The processor 704 is connected to a communication bus 706. Various software embodiments are described in terms of this example computer system. After reading this description, it will become apparent to a person skilled in the relevant art how to implement the invention using other computer systems and/or computer architectures.

Computer system 702 also includes a main memory 708, preferably random access memory (RAM), and can also include a secondary memory 710. The secondary memory 710 can include, for example, a hard disk drive 712 and/or a removable storage drive 714, representing a floppy disk drive, a magnetic tape drive, an optical disk drive, etc. The removable storage drive 714 reads from and/or writes to a removable storage medium 718 in a well known manner. Removable storage media 718, represents a floppy disk, magnetic tape, optical disk, etc. which is read by and written to by removable storage drive 714. As will be appreciated, the removable storage media 718 includes a computer usable storage medium having stored therein computer software and/or data.

In alternative embodiments, secondary memory 710 may include other similar means for allowing computer programs or other instructions to be loaded into computer system 702. Such means can include, for example, a removable storage unit 722 and an interface 720. Examples of such can include a program cartridge and cartridge interface (such as that found in video game devices), a removable memory chip (such as an EPROM, or PROM) and associated socket, and other removable storage units 722 and interfaces 720 which allow software and data to be transferred from the removable storage unit 718 to computer system 702.

Computer system 702 can also include a communications interface 724. Communications interface 724 allows software and data to be transferred between computer system 702 and external devices. Examples of communications interface 724 can include a modem, a network interface (such as an Ethernet card), a communications port, a PCMCIA slot and card, etc. Software and data transferred via communications interface 724 are in the form of signals which can be electronic, electromagnetic, optical or other signals capable of being received by communications interface 724. These signals are provided to communications interface via a channel 728. This channel 728 carries signals and can be implemented using a wireless medium, wire or cable, fiber optics, or other communications medium. Some examples of a channel can include a phone line, a cellular phone link, an RF link, a network interface, and other communications channels.

In this document, the terms "computer program medium" and "computer usable medium" are used to generally refer to media such as removable storage device 718, a hard disk installed in hard disk drive 712, and signals on channel 728. These computer program products are means for providing software to computer system 702.

Computer programs (also called computer control logic) are stored in main memory and/or secondary memory 710. Computer programs can also be received via communications interface 724. Such computer programs, when executed, enable the computer system 702 to perform the features of the present invention as discussed herein. In particular, the computer programs, when executed, enable the processor 704 to perform the features of the present invention. Accordingly, such computer programs represent controllers of the computer system 702.

In an embodiment where the elements are implemented using software, the software may be stored in a computer program product and loaded into computer system 702 using removable storage drive 714, hard drive 712 or communications interface 724. The control logic (software), when executed by the processor 704, causes the processor 704 to perform the functions of the invention as described herein.

In another embodiment, the elements are implemented primarily in hardware using, for example, hardware components such as application specific integrated circuits (ASICs). Implementation of the hardware state machine so as to perform the functions described herein will be apparent to persons skilled in the relevant art(s). In yet another embodiment, elements are implemented using a combination of both hardware and software.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The methods, apparatus, computer programmable media, assay devices, and kits of the invention are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. An apparatus for measuring progress and time of completion of an assay in an assay device, comprising:
    (a) said assay device comprising
        a reaction chamber and
        at least one diagnostic lane, wherein a label is provided in said reaction chamber;
    (b) an optical component for detecting a signal generated from said label in at least one discrete zone of said diagnostic lane; and
    (c) a signal processor for determining said progress and time of completion of said assay in said assay device from at least one parameter selected from the group consisting of a rate of change of the amount of said signal and an absolute amount of said signal;
    wherein the label does not appreciably bind to assay reagents in said assay device.

2. A kit for measuring progress and time of completion of an assay in an assay device, comprising:
    (a) instructions comprising text or diagrams about the apparatus and/or kit; and
    (b) an apparatus, comprising:
        (i) said assay device comprising
            a reaction chamber and
            at least one diagnostic lane, wherein a label is provided in said reaction chamber;
        (ii) an optical component for detecting a signal generated from said label in at least one discrete zone of said diagnostic lane; and
        (iii) a signal processor for determining said progress and time of completion of said assay in said assay device from at least one parameter selected from the group consisting of a rate of change of the amount of said signal and an absolute amount of said signal;
    wherein the label does not appreciably bind to assay reagents in said assay device.

3. An apparatus for measuring progress and time of completion of an assay in an assay device, comprising:
    (a) said assay device comprising
        a reaction chamber, and
        at least one diagnostic lane, wherein said diagnostic lane is in fluid communication with said reaction chamber when fluid and a detectable label are added to said reaction chamber;
    (b) an optical component for detecting a signal generated from said label in at least one discrete zone of said diagnostic lane; and
    (c) a signal processor for determining said progress and time of completion of said assay in said assay device from at least one parameter selected from the group consisting of a rate of change of the amount of said signal and an absolute amount of said signal;
    wherein the label does not appreciably bind to assay reagents in said assay device.

4. The apparatus of claim 1, wherein said label is linked to a member of a binding pair.

5. The apparatus of claim 4, wherein the member of a binding pair is selected from the group consisting of binding protein, antibody, antibody fragment, protein, peptide, and organic molecule.

6. The apparatus of claim 1, wherein said assay reagents are selected from the group consisting of binding protein, antibody, antibody fragment, protein, peptide, and organic molecule.

7. The apparatus of claim 1, wherein said label is selected from the group of molecules consisting of dye, fluorescence emitting dye, chemiluminescence emitting dye, infrared emitting dye, colloidal sol, molecule that generates an electrical and/or magnetic signal, and enzyme.

8. The kit of claim 2, wherein said label is linked to a member of a binding pair.

9. The kit of claim 8, wherein the member of a binding pair is selected from the group consisting of binding protein, antibody, antibody fragment, protein, peptide, and organic molecule.

10. The kit of claim 2, wherein said label is selected from the group of molecules consisting of dye, fluorescence emitting dye, chemiluminescence emitting dye, infrared emitting dye, colloidal sol, molecule that generates an electrical and/or magnetic signal, and enzyme.

11. The kit of claim 2, wherein said assay reagents are selected from the group consisting of binding protein, antibody, antibody fragment, protein, peptide, and organic molecule.

12. The apparatus of claim 3, wherein said label is linked to a member of a binding pair.

13. The apparatus of claim 12, wherein the member of a binding pair is selected from the group consisting of binding protein, antibody, antibody fragment, protein, peptide, and organic molecule.

14. The apparatus of claim 3, wherein said label is selected from the group of molecules consisting of dye, fluorescence emitting dye, chemiluminescence emitting dye, infrared emitting dye, colloidal sol, molecule that generates an electrical and/or magnetic signal, and enzyme.

15. The apparatus of claim 3, wherein said assay reagents are selected from the group consisting of binding protein, antibody, antibody fragment, protein, peptide, and organic molecule.

\* \* \* \* \*